(12) United States Patent
Zamierowski

(10) Patent No.: US 7,645,269 B2
(45) Date of Patent: Jan. 12, 2010

(54) GRADIENT WOUND TREATMENT SYSTEM AND METHOD

(75) Inventor: David S. Zamierowski, Overland Park, KS (US)

(73) Assignee: KCI Licensing, Inc., San Antonio, TX (US)

( * ) Notice: Subject to any disclaimer, the term of this patent is extended or adjusted under 35 U.S.C. 154(b) by 375 days.

(21) Appl. No.: 11/523,672

(22) Filed: Sep. 19, 2006

(65) Prior Publication Data
US 2007/0038172 A1 Feb. 15, 2007

Related U.S. Application Data

(63) Continuation-in-part of application No. 10/135,741, filed on Apr. 30, 2002, now Pat. No. 7,108,683.

(60) Provisional application No. 60/287,323, filed on Apr. 30, 2001.

(51) Int. Cl.
*A61F 13/00* (2006.01)
(52) U.S. Cl. ........... 604/305; 604/543
(58) Field of Classification Search ......... 604/304–308, 604/313, 317–327, 540–544, 378, 24, 40
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,648,692 A | 3/1972 | Wheeler | |
| 3,682,180 A | 8/1972 | McFarlane | |
| 3,826,254 A | 7/1974 | Mellor | |
| 3,880,164 A * | 4/1975 | Stepno | 604/131 |
| 4,080,970 A | 3/1978 | Miller | |
| 4,096,853 A | 6/1978 | Weigand | |

(Continued)

FOREIGN PATENT DOCUMENTS

AU 550575 A1 8/1982

(Continued)

OTHER PUBLICATIONS

Louis C. Argenta, MD and Michael J. Morykwas, PhD; "Vacuum-Assisted Closure; A New Method for Wound Control and Treatment: Clinical Experience"; Annals of Plastic Surgery, vol. 38, No. 6, Jun. 1997; pp. 563-576.

(Continued)

*Primary Examiner*—Michele Kidwell

(57) ABSTRACT

A wound therapy and tissue management system utilizes fluid differentiation. Fluid is differentiated by establishing a gradient within the system. A gradient can be established with matter or energy. Patient interfaces for establishing, maintaining and varying one or more gradients include transfer elements with first and second zones having different flow coefficients. The transfer elements exchange fluid with a patient, generally through a wound site, and with external components of the system. Osmotic solution gradients are controlled by a methodology involving the present invention for extracting solutions, which can include toxins, from patients and for introducing fluids and sumping air to wound sites.

20 Claims, 45 Drawing Sheets

U.S. PATENT DOCUMENTS

| | | |
|---|---|---|
| 4,139,004 A | 2/1979 | Gonzalez, Jr. |
| 4,165,748 A | 8/1979 | Johnson |
| 4,233,969 A | 11/1980 | Lock et al. |
| 4,245,630 A | 1/1981 | Lloyd et al. |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,152,757 A * | 10/1992 | Eriksson ............... 604/305 |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,678,564 A * | 10/1997 | Lawrence et al. ........... 600/574 |
| 6,071,267 A | 6/2000 | Zamierowski |
| 6,135,116 A | 10/2000 | Vogel et al. |
| 6,234,990 B1 * | 5/2001 | Rowe et al. .................... 604/22 |
| 6,241,747 B1 | 6/2001 | Ruff |
| 6,258,075 B1 * | 7/2001 | Taylor et al. ........... 604/385.18 |
| 6,287,316 B1 | 9/2001 | Agarwal et al. |
| 6,345,623 B1 | 2/2002 | Heaton et al. |
| 6,398,767 B1 | 6/2002 | Fleischmann |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2001/0011169 A1 * | 8/2001 | Taylor et al. ........... 604/385.18 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0191443 A1 * | 10/2003 | Taylor et al. ........... 604/385.18 |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 198 44 355 A1 | 4/2000 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 90/11795 | 10/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 01/85248 A1 | 11/2001 |
| WO | WO 01/89431 A1 | 11/2001 |
| WO | WO 03/092620 A3 * | 11/2003 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD. et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elseiver Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion, PCT International Application PCT/GB98/02713; Jun. 8, 1999.

PCT International Examinatin and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip, P., Jr., et al: "Medical Textiles: Application of an Absorbale Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A, et al; "Vacuum Therapy in the Treatment of Purulent Lactation Mastitis"; Vestnik Khirurgi, May 14, 1986, pp. 66-70, and 9 page English translation thereof.

Yusupov, Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy", Vestnik Khirurgi, Jul. 7, 1980, pp. 132-136, and 8 page English translation thereof.

Johnson, F.E. "An Improved Technique For Skin Graft Placement Using A Suction Drain, Surgery, Gynecology and Obstetrics", 1984; 159 (6), 584-5.

* cited by examiner

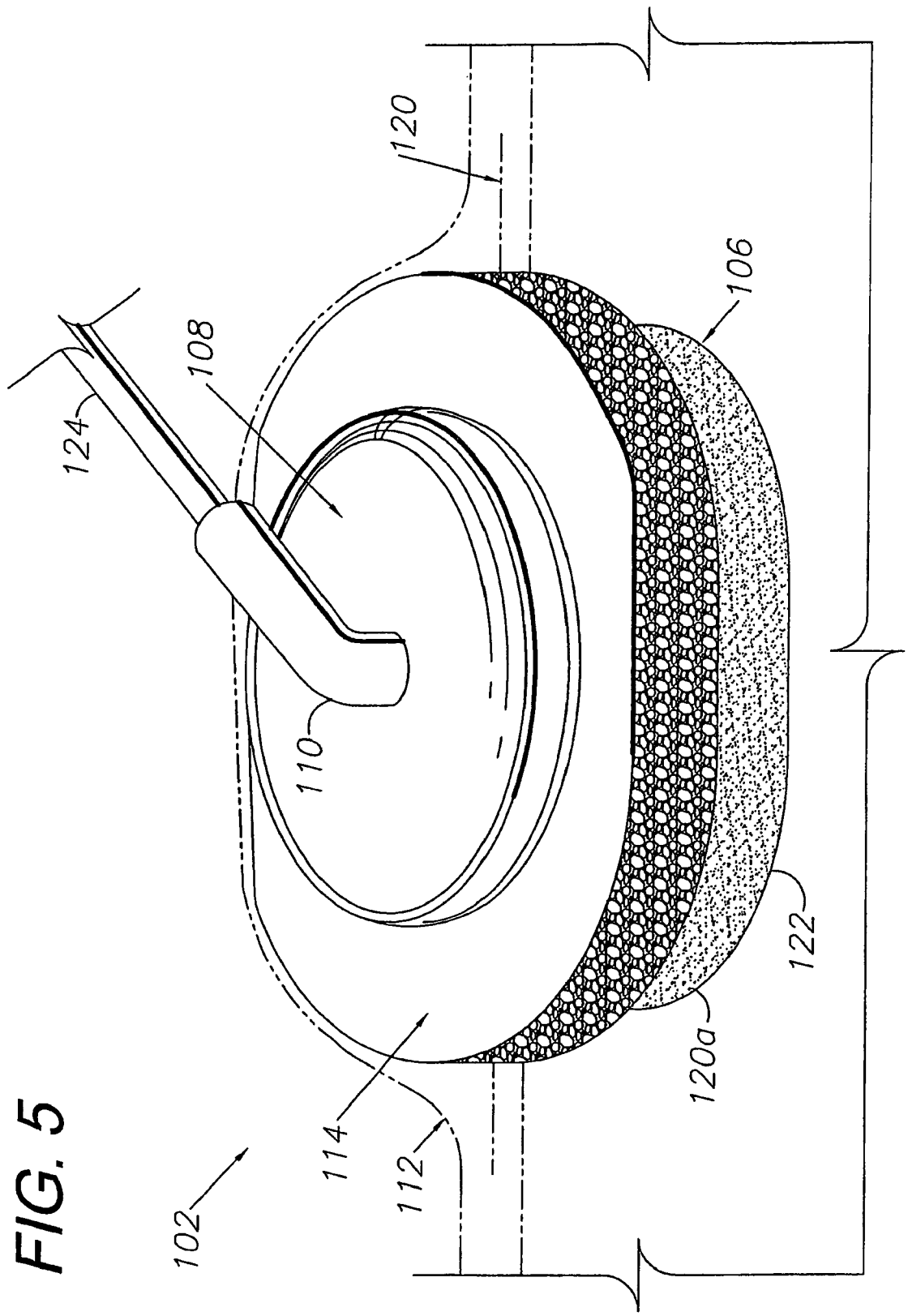

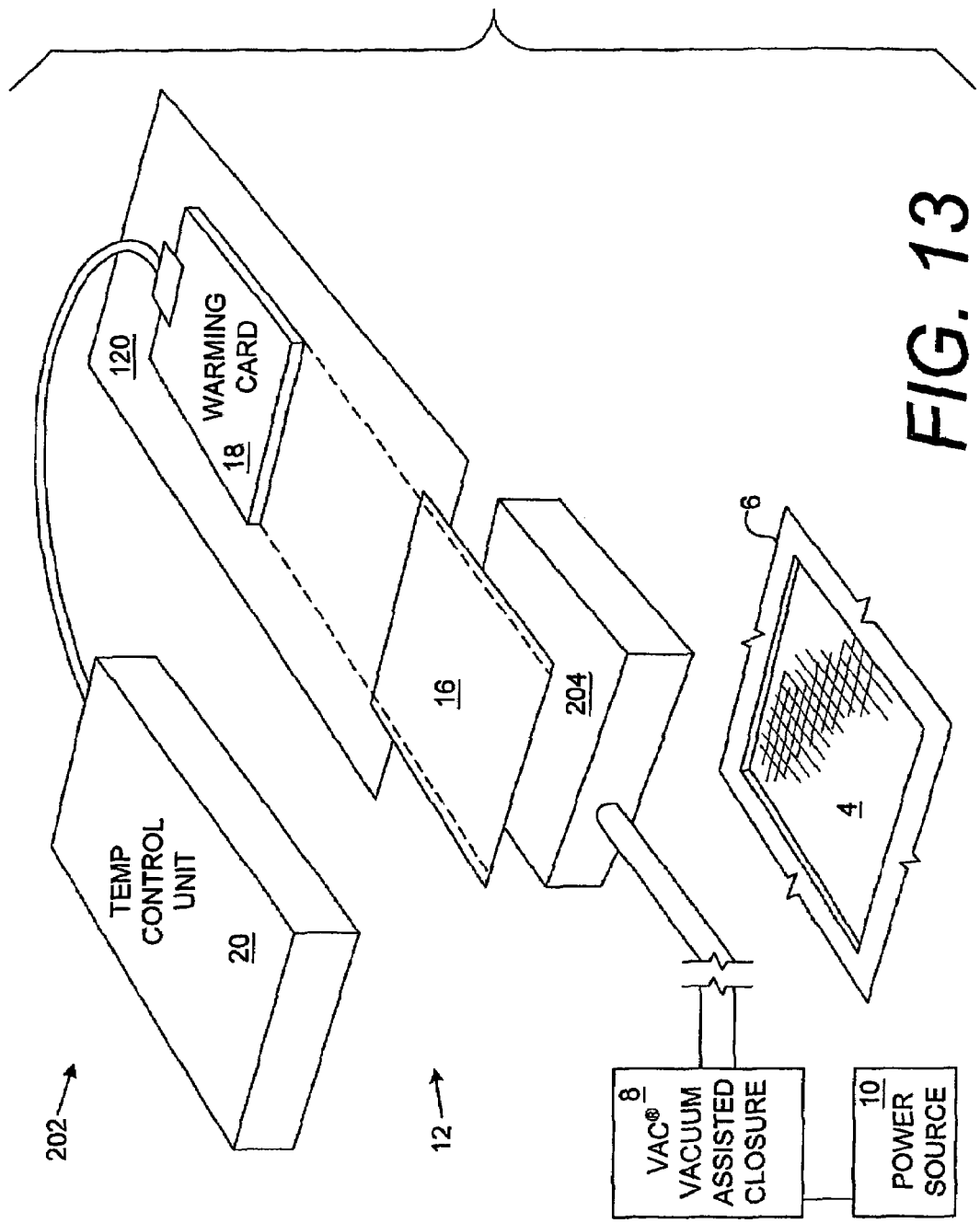

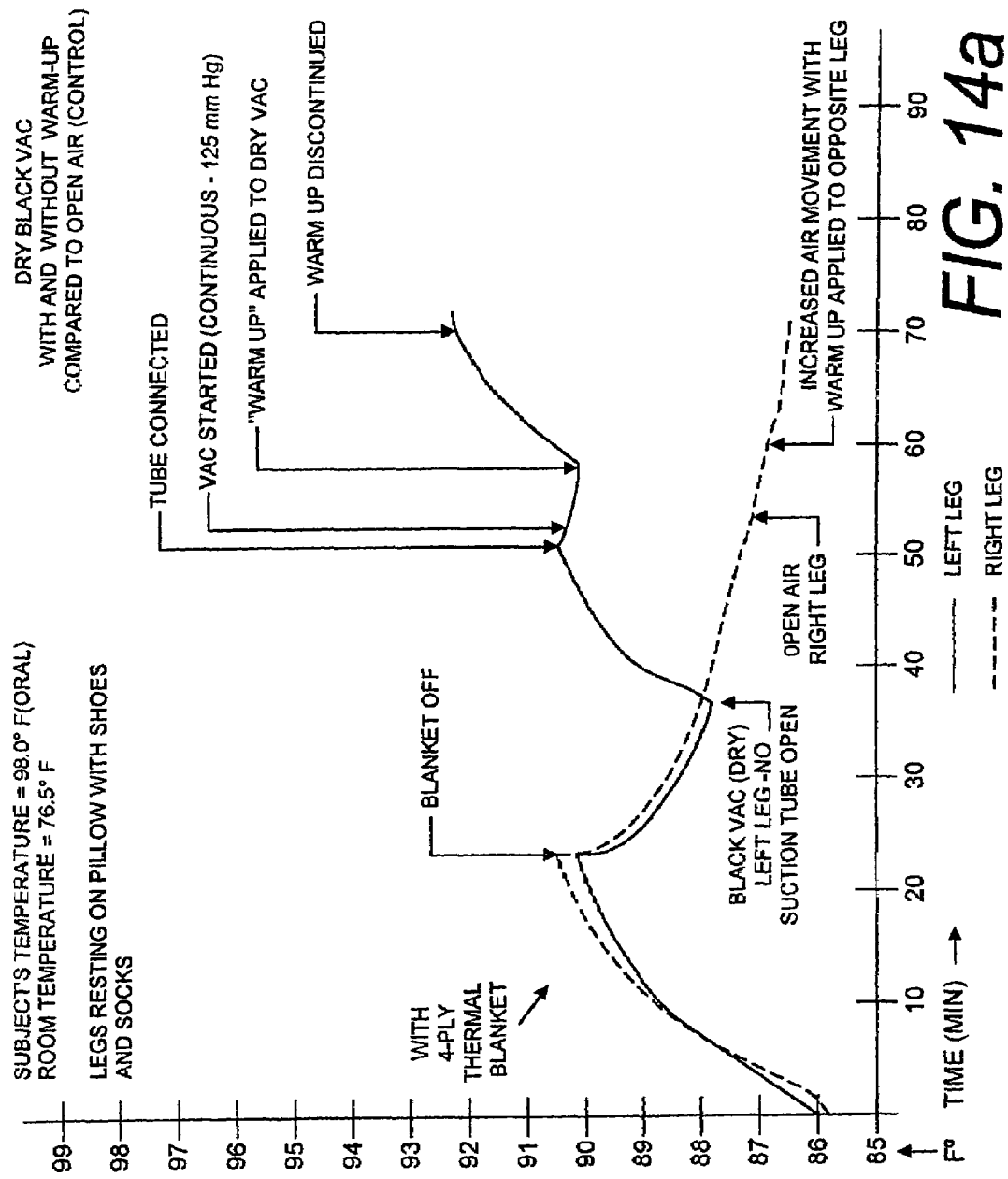

FIG. 21

HYPO-OSMOLAR OR HEAVY DRAPE SYSTEM

| PHASE: | 1 | 2 | 3 | 4 |
|---|---|---|---|---|
| TRANSFER ELEMENT | (empty) | HYPO-OSMOLAR | ←FLUID  FLUID→ | (empty) |
| WOUND | FLUID  TOXIN A | FLUID  TOXIN A | FLUID  TOXIN A | FLUID ←TOXIN A |
| CAPILLARY | (arrows) | (empty) | (empty) | LYMPHATICS |

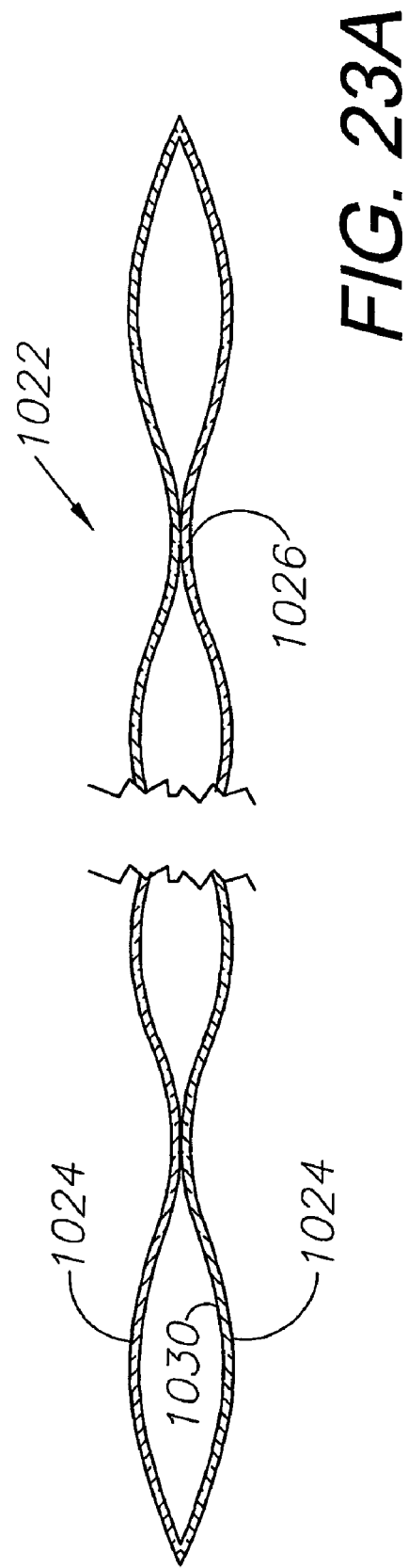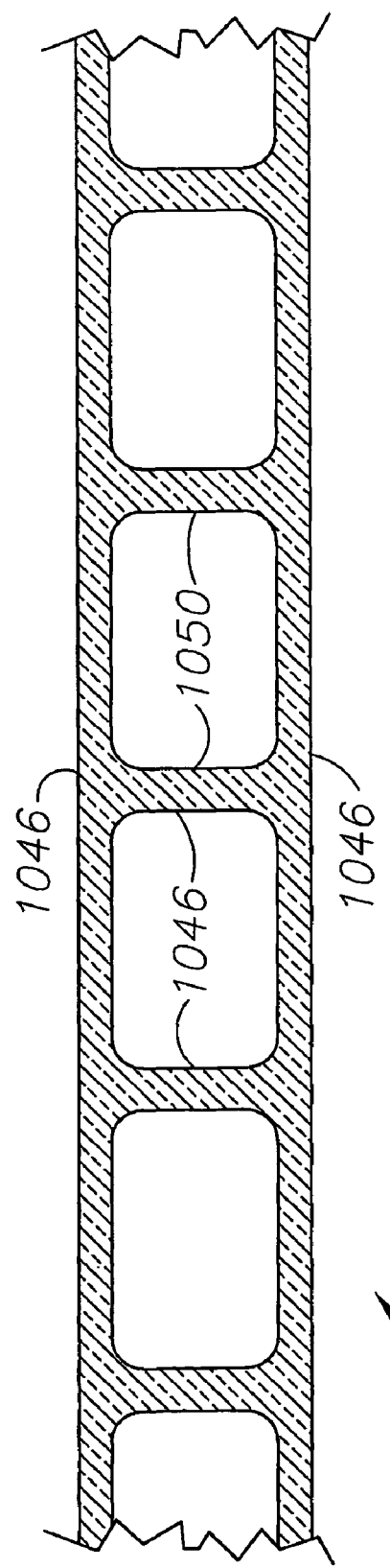

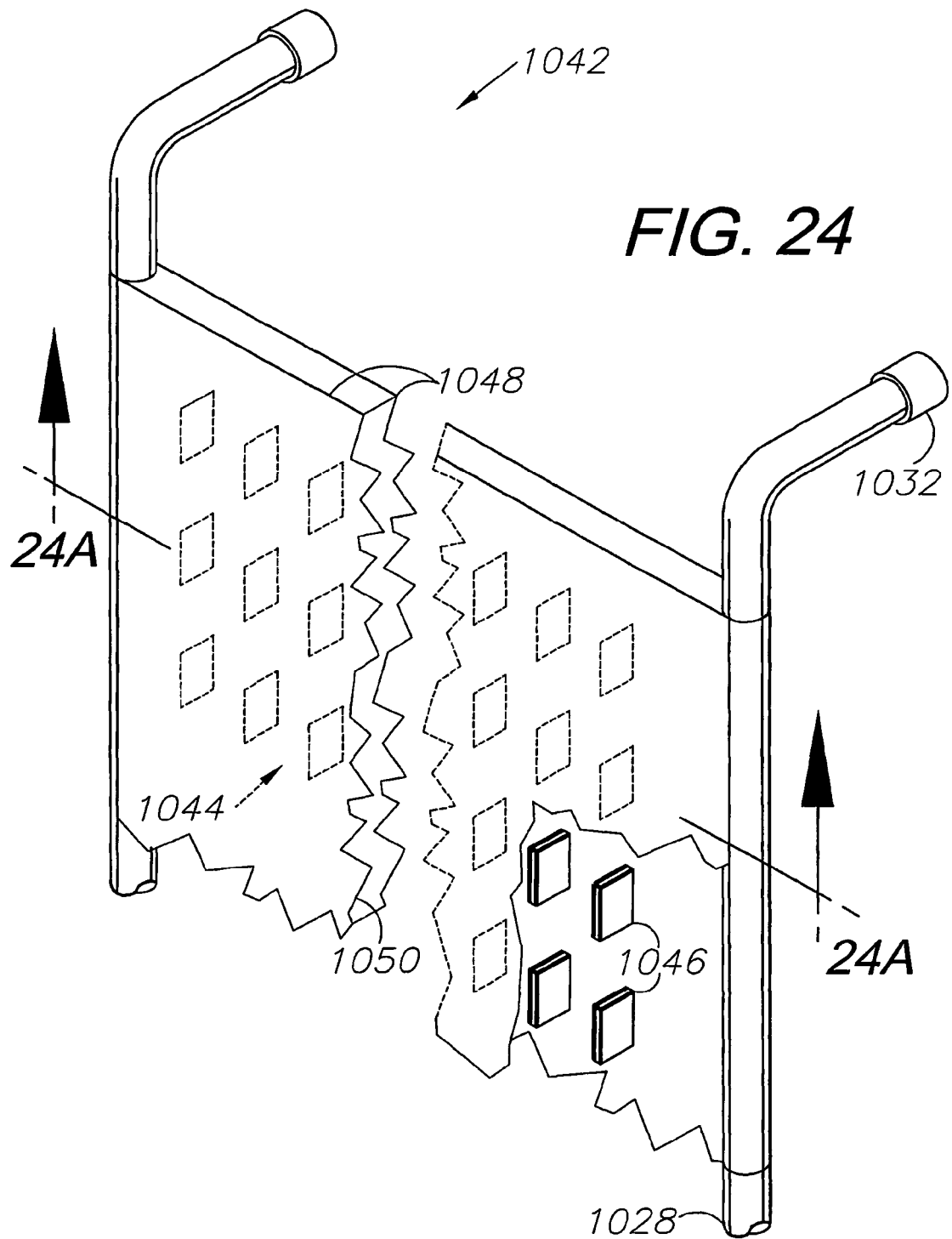

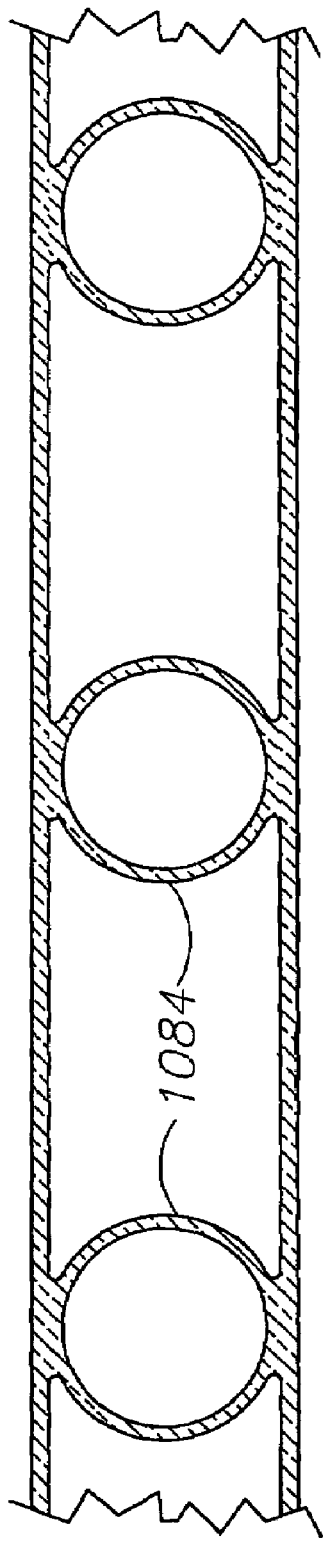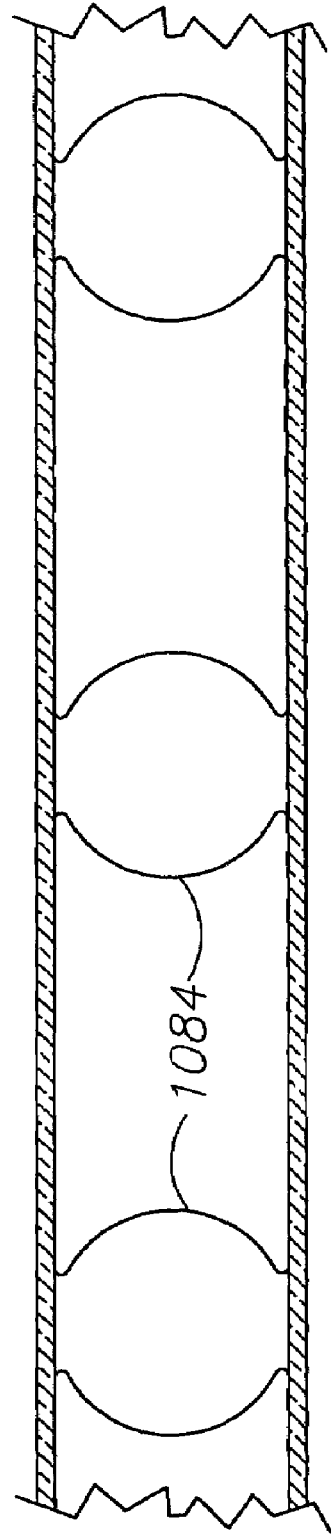

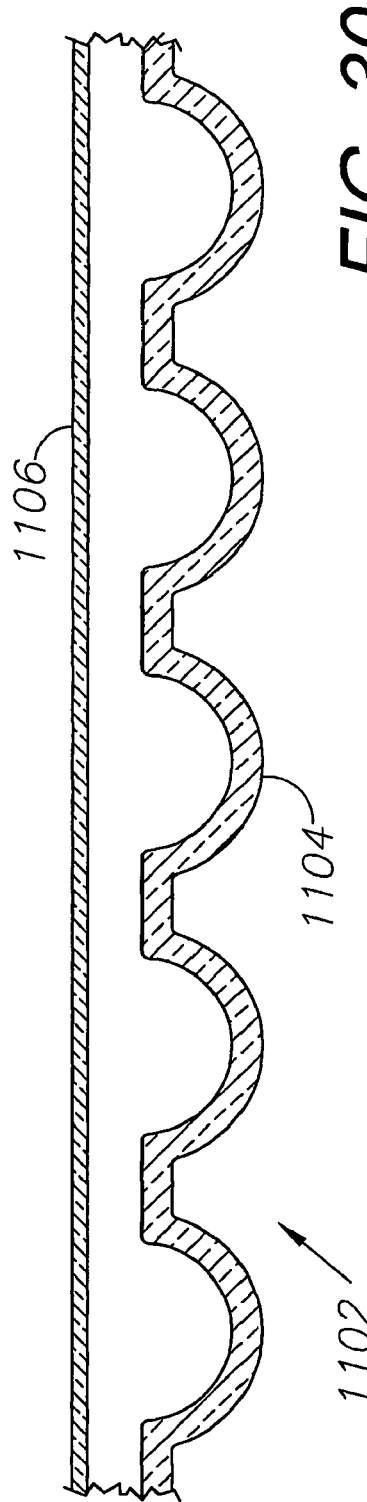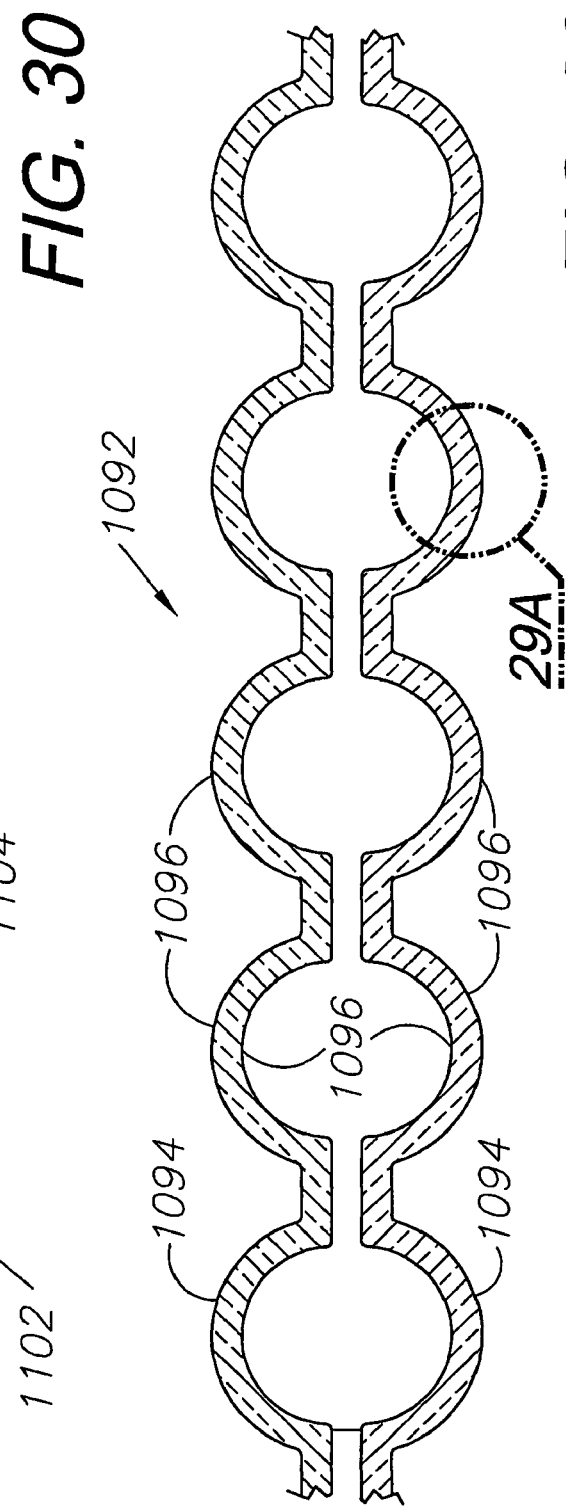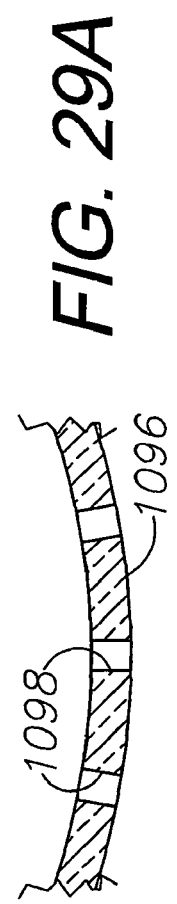

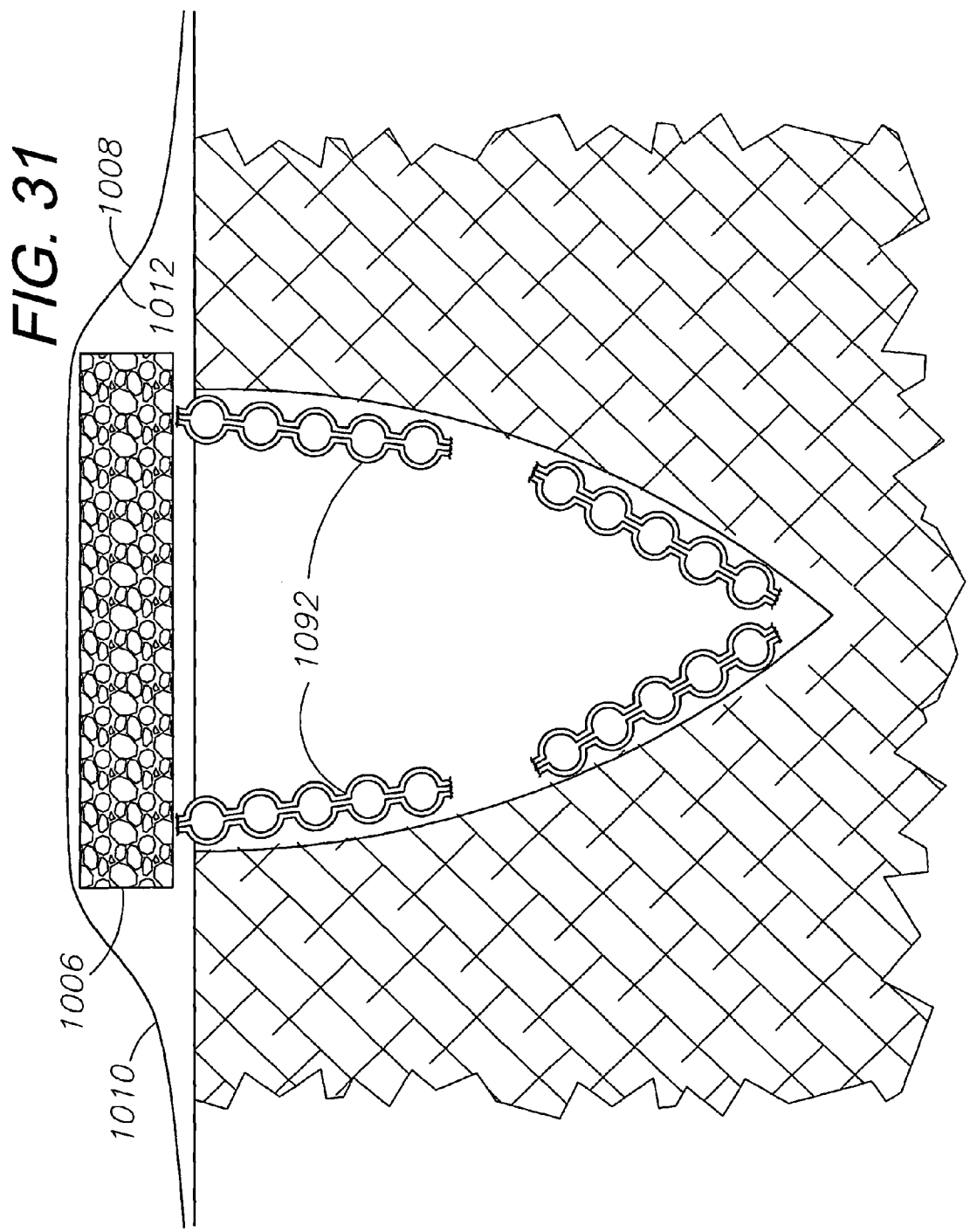

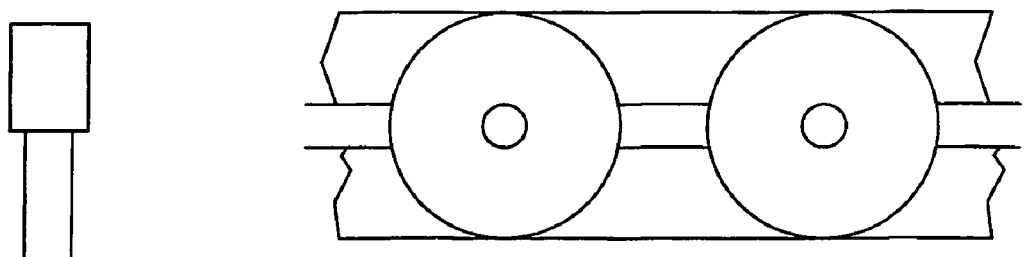
*FIG. 33A*
*FIG. 33*
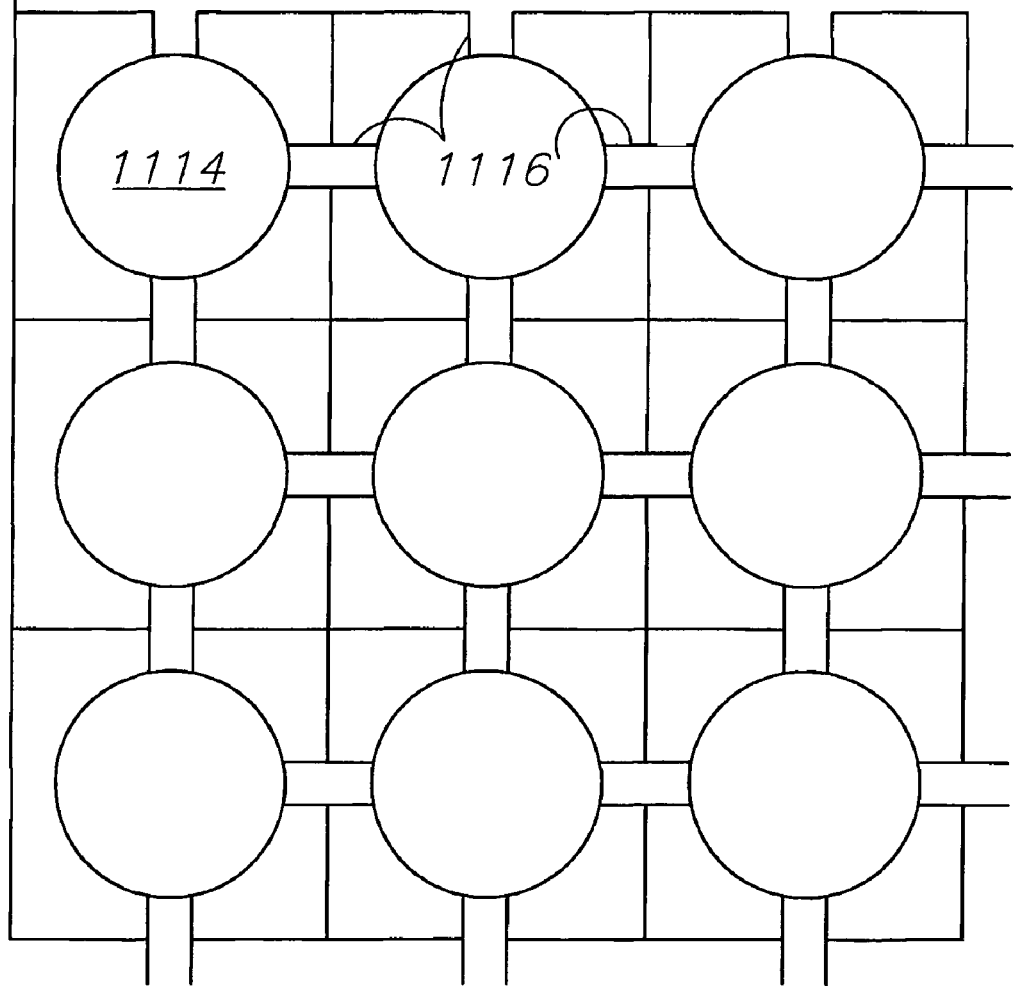

GRADIENT WOUND TREATMENT SYSTEM AND METHOD

CROSS-REFERENCE TO RELATED APPLICATION AND PRIORITY CLAIM

The present application is a continuation-in-part of U.S. patent application Ser. No. 10/135,741, filed Apr. 30, 2002, now U.S. Pat. No. 7,108,683, which is based on and claims priority in U.S. Provisional Patent Application Ser. No. 60/287,323, filed Apr. 30, 2001.

BACKGROUND OF THE INVENTION

1. Field of the Invention

The present invention relates generally to medical care, and in particular to wound therapy and tissue management systems and methodologies with fluid differentiation.

2. Description of the Prior Art

Heretofore, many wound therapy and tissue management devices and protocols have tended to focus on the addition or control of individual mechanical forces and their respective effects on wound healing. For example, the use of suction to secure skin graft dressings in place is disclosed in Johnson, F. E., *An Improved Technique for Skin Graft Placement Using a Suction Drain*; Surgery, Gynecology and Obstetrics 1984; 159 (6): 584-5. Other prior art devices have focused on the application of compressive (i.e. positive or greater-than-atmospheric) pressure to a wound site, the application of heat and the delivery of pharmacologic agents.

Standard methods in the current practice of wound care require changing the dressing in order to topically add pharmacological agents, which require interval reapplication. Reapplications of pharmacological agents can be minimized or eliminated by using slow-release delivery systems. However, such systems must generally be changed in their entireties in order to change the agents or dosages.

Another wound treatment protocol option involves dosing the entire patient. Agents are thereby delivered systemically, i.e. from within the patient, in order to arrive at the wound site, as opposed to other protocols which deliver respective agents externally or topically. However, systemic medications are generally administered in relatively high doses in order to provide sufficient concentrations in affected areas and treatment sites. Non-affected tissues and organs remote from the treatment sites thus tend to receive concentrations of medications from which they may not benefit.

Fluid management significantly affects many aspects of health care and is involved in many medical procedures. For example, wound care typically involves absorbing and/or draining wound exudates, blood, serum and other body fluids from the patient. Surgical procedures often create wounds requiring tissue management and fluid drainage. For example, skin grafts have exudates and bleeding that require management at both the donor and graft sites. However, current tissue management and fluid drainage procedures are often ineffective in maintaining optimum moisture content for promoting wound healing. Excessive drying, on the one hand, can lead to desiccation, eschar formation and slowing of cell migration. Excessive moisture, on the other hand, can lead to maceration, bacterial overgrowth, tissue breakdown and necrosis.

Various types of porous, absorbent dressing materials have been used for dressing wounds to accumulate body fluids. The dressing materials facilitate drainage and also the collection and disposal of fluids. A disadvantage with many conventional dressings is that they require changing in order to reduce the risk of infection and to maintain effectiveness. However, dressing changes can add significantly to treatment costs and are associated with patient discomfort and medical risks such as infection and damage to reepithelialized tissues. Accordingly, vacuum sources have been employed to drain wounds. For example, Zamierowski U.S. Pat. No. 4,969,880; No. 5,100,396; No. 5,261,893; No. 5,527,293 and No. 6,071,267 pertain to wound dressings, fluid connections, fastening systems and medical procedures utilizing same in connection with vacuum-assisted wound drainage, and are incorporated herein by reference.

A wound drainage device using a hand-operated suction bulb is shown in the George et al. U.S. Pat. No. 4,392,858. Motorized suction pumps can be employed to provide consistent, sub-atmospheric vacuum pressure for maintaining an effective drainage flow. The Richmond et al. U.S. Pat. No. 4,655,754 and No. 4,826,494 disclose vacuum wound drainage systems which can be connected to motorized vacuum pumps.

Another important objective in designing an effective wound drainage system is to provide an effective interface with the patient. Ideally, the patient interface should accommodate various types of wounds in different stages of recovery for as broad a range of applications as possible. As noted above, optimum wound healing generally involves maintaining a sufficient moisture level to avoid desiccation without causing the wound to macerate from excessive moisture. Sufficient moisture levels are required for epithelial cell migration, but excessive moisture can inhibit drying and maturation of the epithelial layer. Pressures should be sufficient for effective drainage without creating excessive negative forces, which could cause pressure necrosis or separate freshly-applied skin grafts.

Wound treatment procedures can also include infusing wound sites with liquids to flush contaminants, counter infection, promote healing growth and anesthetize the wound. Prior art fluid delivery systems include a device for treating tissues disclosed in the Svedman U.S. Pat. No. 4,382,441; a product and process for establishing a sterile area of skin disclosed in the Gross U.S. Pat. No. 3,367,332; and the transdermal infusion device disclosed in the Westin U.S. Pat. No. 4,605,399. Equipment has also been available which flushes and collects contaminants from wounds.

Heretofore, there has not been available a system or methodology that allowed the manipulation of multiple mechanical forces affecting wound surfaces. Moreover, there has not previously been available a system or methodology that manipulated the gradients of gases, solids, liquids and medications in such a way as to provide the medical practitioner with various options for delivering various agents either systemically from the patient side or topically from the external side of a wound. Further, there has not been available a system or methodology which affected the removal of toxins and undesirable byproducts by an external egress with the advantages and features of the present invention. Such advantages include minimizing or eliminating dressing changes whereby patient discomfort and infection risks are correspondingly reduced.

Effective control of fixation, temperature, pressure (and its associated gradients for vital gases such as oxygen), osmotic, and oncotic forces, electrical and electromagnetic fields and forces and the addition and/or removal of various nutrients and pharmacological agents have not been achievable with the previous systems and methodologies. Still further, there has not been available a wound treatment system and methodology utilizing a transfer element for the manipulation of gas and liquid pathways under the control of pre-programmed, coordinated influx and efflux cycles. Such cycles are designed to maintain the desired integrity and stability of the system while still allowing variations in multiple forces, flows and concentrations within tolerated ranges. The previous wound treatments also tended to lack the dynamic and interactive features of the present invention whereby various gradients can be adjusted in response to patient wound site conditions. Such gradient adjustments can be accomplished with the present invention through the use of biofeedback loops and patient-responsive sensors.

Osmotic and concentration gradients provide an important mechanism for transferring various elements within the scope of the present invention. Such gradients occur naturally in living organisms and involve the movement of solutes from solutions with greater concentrations to solutions with lesser concentrations through semi-permeable membranes. Osmosis is the tendency of solids to pass through semi-permeable membranes into solutions of higher concentrations in order to achieve osmotic equilibrium. Diffusion occurs from an area of higher concentration or partial pressure to an area of lower concentration even without membrane separation. Examples include the diffusion transfer of oxygen from alveoli to capillaries within the lung and the osmotic transfer of toxins and waste within the kidneys from capillaries to tubules and on to the bladder. The systems and methods of the present invention utilize and control osmotic and diffusion gradients to advantage in treating wounds, particularly in connection with the removal of toxins and solution from wound sites by controlling fluids. The control of fluids originates both internally and externally. For example, wound exudates originate internally. External control fluids include sumped air, irrigation, etc.

Previous wound treatment systems and methodologies did not provide medical practitioners with the range of options available with the present invention for treating various patient circumstances and conditions.

SUMMARY OF THE INVENTION

In the practice of the present invention, a wound therapy and tissue management system is provided, which includes a collector assembly for attachment to a patient, a transfer assembly connected to the collector assembly and a gradient (e.g., negative pressure/vacuum, positive pressure, temperature, oxygen, etc.) source connected by tubing to the transfer assembly. The system is adaptable for use with various dressing assemblies, including multiple layers and components comprising hydrophobia and hydrophilic foam and sponge materials, semi-permeable and impermeable membranes applied as drapes, transfer system conduits and buffers, and tubular connections to pumps. Alternative embodiments of the system utilize osmotic gradients for controlling transfers and provide various optional configurations with internal and external inputs, installation ports and other components. In the practice of the method of the present invention, a fluid differentiation wound therapy and tissue management method is disclosed, which includes steps of shaping and applying a first sponge comprising a first sponge material to a wound area, applying a first drape, shaping and applying a second sponge comprising a second sponge material on top of the first drape and the first sponge, forming a fluid conduit and connecting same to the second sponge and to a buffer for ultimate connection to a vacuum pump. The conduit and the buffer are also draped. Osmotic wound therapy and tissue management methodologies are also disclosed in connection with the present invention. The transfer of fluids and substances such as toxins can be controlled through the application of such methodologies. In the practice of other aspects of the present invention, osmotic transducers are provided for treating wounds by manipulating the gaseous, liquid and solid components in such a way as to create pressure gradients in fluid elements that produce useful fluid flow.

BRIEF DESCRIPTION OF THE DRAWINGS

FIG. 5 is a perspective view of a composite dressing comprising a second modified embodiment of the present invention.

FIG. 13 is an exploded view of yet another wound treatment system with vacuum, heat and fluid assistance.

FIGS. 14a-d comprise graphs showing the temperature-elevating performance of the wound treatment systems shown in FIGS. 11-13.

FIG. 21 is a diagram showing a hypo-osmolar or heavy drape system embodying the present invention.

FIG. 23A is a cross-sectional view thereof, taken generally along line 23A-23A in FIG. 23.

FIG. 24 is a perspective view of another alternative embodiment composite sheet panel system.

FIG. 24A is a cross-sectional view thereof, taken generally along line 24A-24A in FIG. 24.

FIG. 28A is a cross-sectional view thereof, taken generally along line 28A in FIG. 28.

FIG. 28B is another cross-sectional view thereof, taken generally along line 28B in FIG. 28.

FIG. 29 is a cross-sectional view of another alternative embodiment composite sheet panel system.

FIG. 29A is an enlarged, cross-sectional view thereof, taken generally within circle 29A in FIG. 29.

FIG. 30 is a cross-sectional view of another alternative embodiment composite sheet panel system.

FIG. 31 is a cross-sectional view thereof, shown in a wound for closing same.

FIG. 33 is a plan view of another alternative embodiment composite sheet panel system.

FIG. 33A is a cross-sectional view thereof.

FIG. 34A is a cross-sectional view thereof.

DETAILED DESCRIPTION OF THE PREFERRED EMBODIMENTS

I. Introduction and Environment

Figure 1:
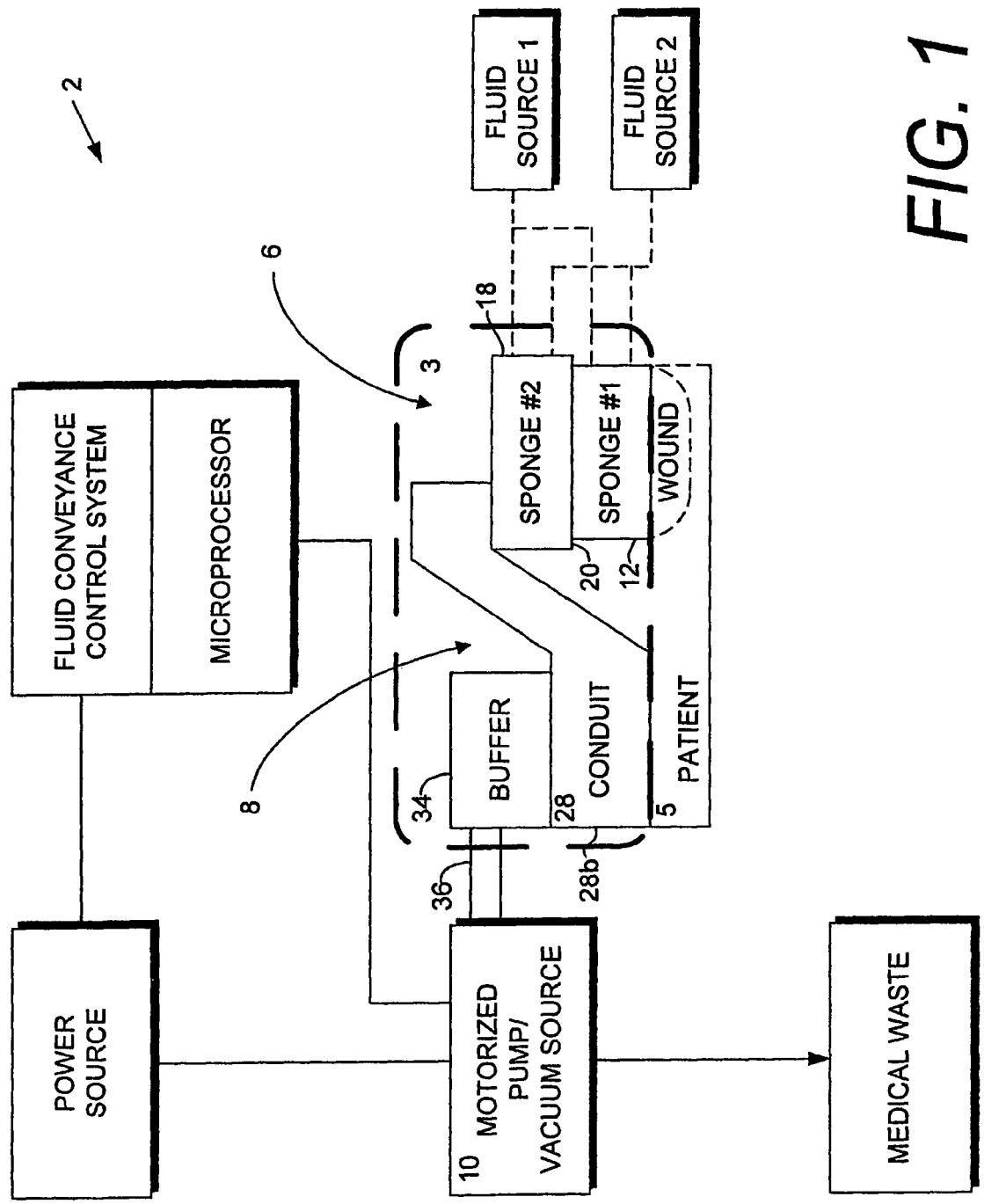
FIG. 1 is a block diagram of a vacuum-fixed wound therapy system embodying the present invention.
Figure 2:
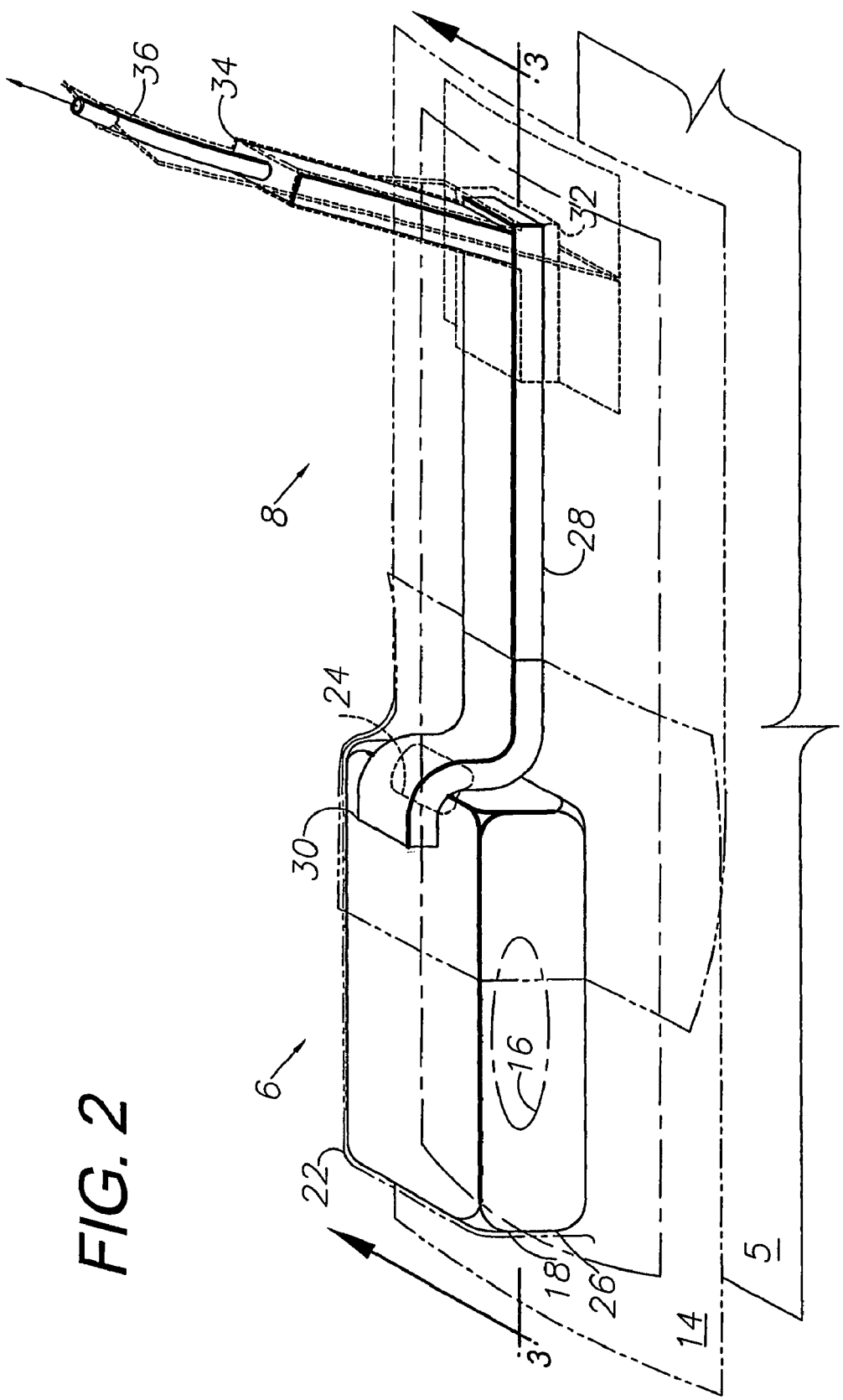
FIG. 2 is a perspective view of a composite dressing assembly.
Figure 3:
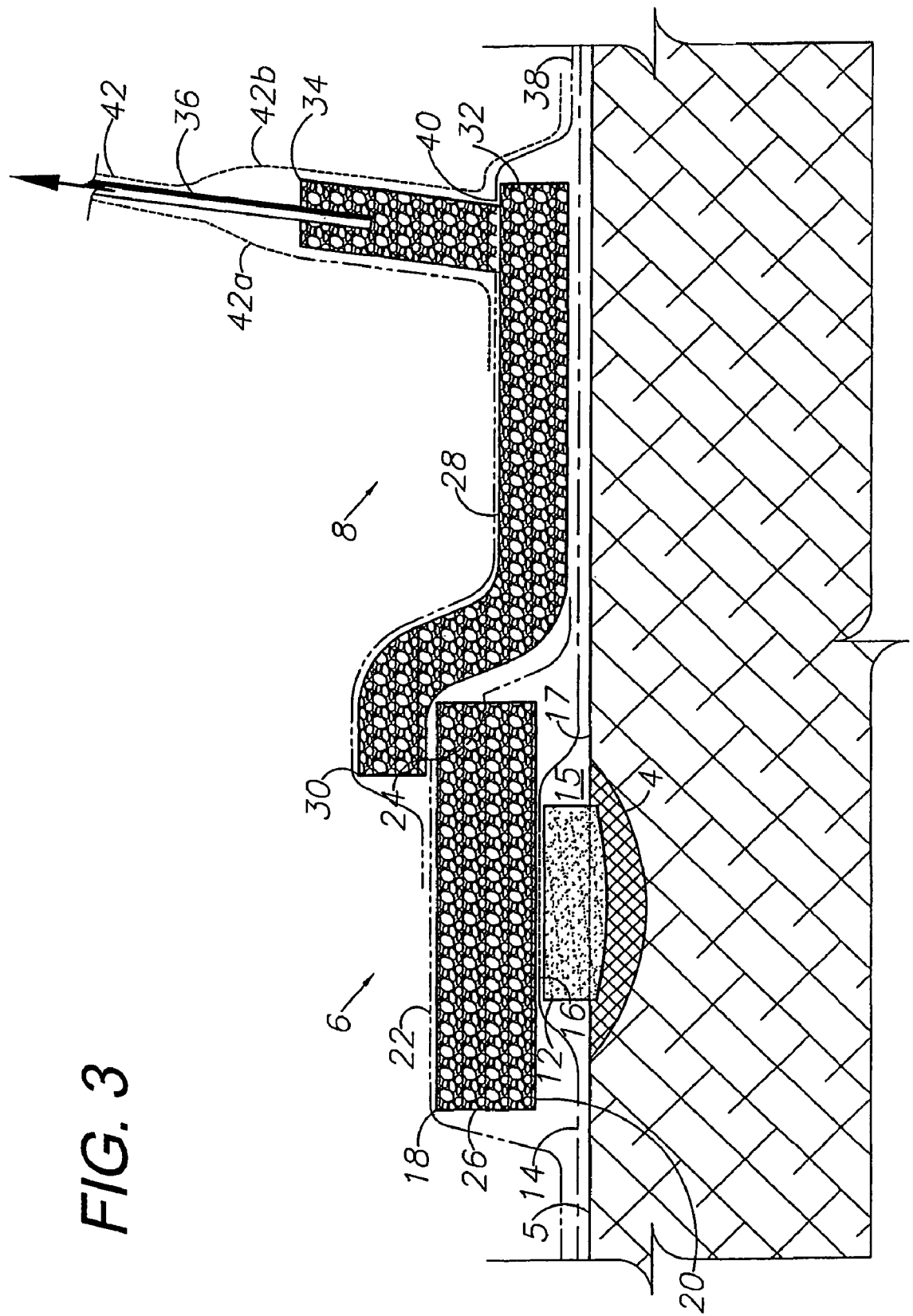
FIG. 3 is a vertical cross-sectional view of the dressing assembly taken generally along line 3-3 in FIG. 2.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Vacuum-fixed Wound Therapy Dressing 3

Referring to the drawings in more detail, the reference numeral 2 generally designates a vacuum-fixed wound therapy system for application to a wound 4 on or in a patient 5. The system 2 includes an improved dressing 3. Other components of the system 2 are described in my U.S. Pat. No. 6,071,267, which is incorporated herein by reference.

The dressing 3 generally includes a collector assembly 6 and a transfer assembly 8 connected to a vacuum source 10. The collector assembly 6 includes a first sponge 12 comprising a hydrophilic material, such as polyvinyl alcohol (PVA). The first sponge 12 is cut to generally conform to the size of the wound 4. A first sponge drape 14 is placed over the first sponge 12 and an opening 16 is formed in the drape 14 and is preferably sized smaller than the first sponge 12. The drape 14 encloses a compression chamber 15 containing the first sponge 12. A dry skin, moisture-control zone 17 is formed around the first sponge 12 due to air circulation within the compression chamber 15 and promotes healing.

A second sponge 18, preferably comprising a hydrophobic polyurethane ether (PUE) material is sized larger than the first sponge 12, whereby a second sponge overhang 20 extends beyond the perimeter of the first sponge 12. A second sponge drape 22 is placed over the second sponge 18 and includes an opening 24 located along an outer edge 26 of the second sponge 18 for directing the outflow of fluid effluent from the collector assembly 6.

The transfer assembly 8 includes a conduit 28, which can comprise the same hydrophobic material as the second sponge 18. The conduit 28 includes an inlet end 30 which is offset in order to overlie the second sponge drape opening 24 along the second sponge outer edge 26. A conduit outlet end 32 mounts a buffer 34, which also preferably comprises the hydrophobic foam and projects outwardly from the conduit 28 and receives a suction tube 36 which is also connected to the vacuum source (e.g., pump) 10. A conduit drape 38 overlies the conduit 28 and includes an opening 40, which receives the buffer 34. A buffer drape 42 includes a first panel 42a and a second panel 42b, which are secured together over the buffer 34 and the suction tube 36 to enclose same. The buffer drape first and second panels 42a,b are mounted on the conduit drape 38 around the opening 40 therein.

In operation, the hydrophilic first sponge 12 tends to collapse under negative pressure. Therefore, the size of the first sponge 12 is limited and it is preferably mounted in proximity to an edge 26 of the second sponge 18. The second sponge 18 cooperates with the transfer assembly to distribute the negative pressure throughout the hydrophobic second sponge 18 and in turn throughout the first sponge 12. The PVA material comprising the first sponge 12 permits it to compress under a negative pressure gradient. Moreover, because the fluid travel distance in the first sponge 12 tends to be relatively short due to its composition, the overlying second sponge 18 tends to distribute the negative pressure gradient relatively evenly across substantially the entire area of the first sponge 12.

The PUE composition of the second sponge 18 provides a reticulated latticework or weave which resists compression and includes relatively open passages to facilitate fluid flow. Although such open-lattice construction has operational advantages, the passages formed thereby in the second sponge 18 tend to receive "spicule" penetrations from the wound, which is undesirable in many applications. Therefore, the collector assembly 6 is constructed by first forming the first sponge 12 to generally conform to the wound 4, whereafter the second sponge 18 is formed to provide the overhang 20. The first sponge 12 is covered with the first sponge drape 14, the opening 16 of which is normally sized smaller than the overall area of the first sponge 12.

The functional advantages of the collector assembly 6 construction include optimizing compression and fixation and edema control at the wound edge while maximizing the air-induced drying of the intact skin in the dry skin zone 17. Moreover, collector assemblies and transfer assemblies can be mixed and configured in a wide variety of arrangements to accommodate various patient conditions. For example, multiple transfer assemblies 8 can be connected to a single collector assembly 6 and vice versa.

III. First Modified Embodiment Fluid Differentiating Wound

Dressing 53

Figure 4:
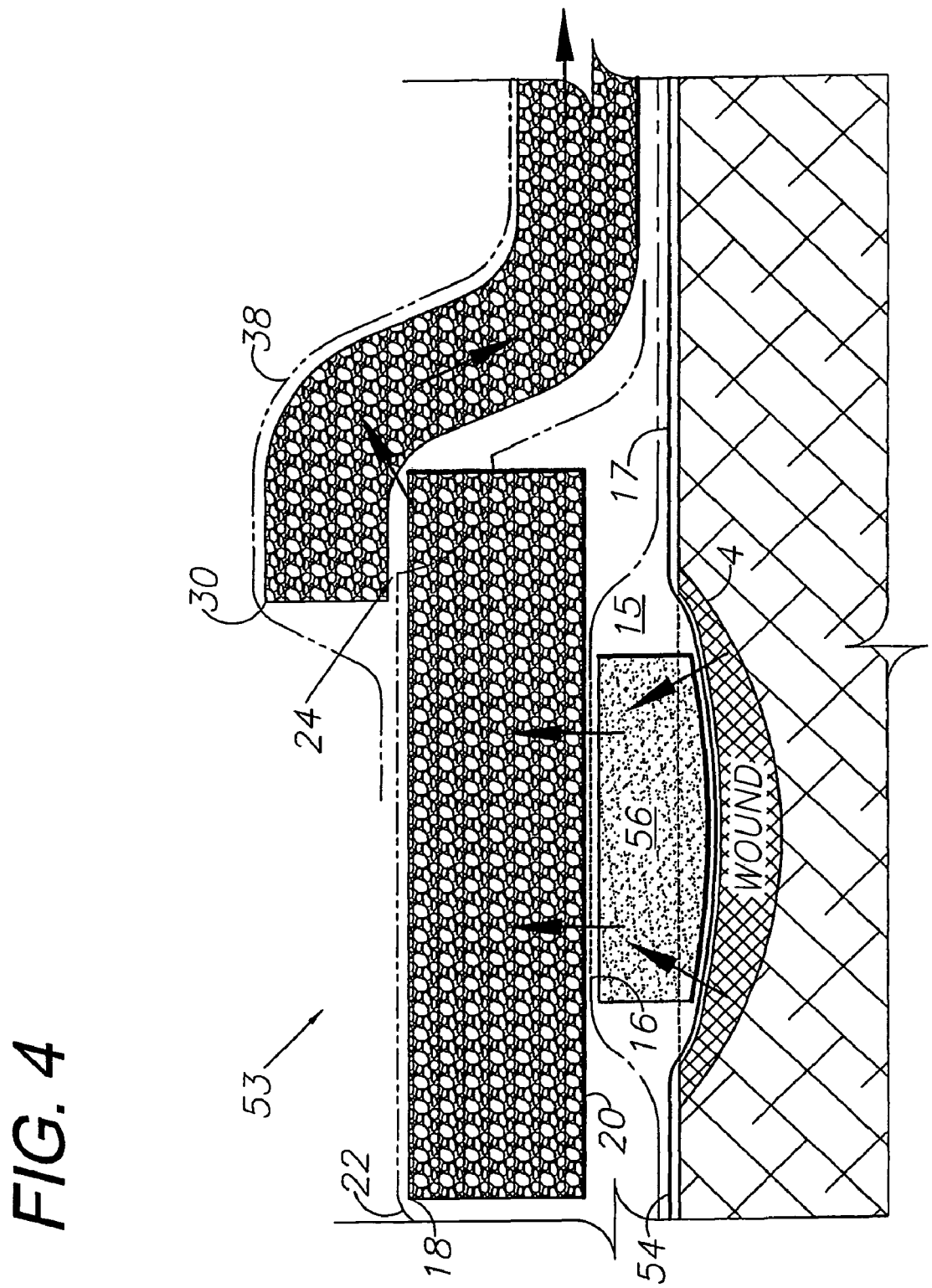
FIG. 4 is an enlarged, fragmentary, cross-sectional view of a composite dressing comprising a first modified embodiment of the present invention.

A wound dressing 53 comprising a first modified embodiment of the present invention is shown in FIG. 4 and includes a liner 54 between the wound 4 and a first sponge 56, which can comprise a hydrophilic or hydrophobic material. The liner 54 passes fluid, but partially isolates and shields the wound tissue from the first sponge 56 to prevent the formation of spicules penetrating the open-passage first sponge 56. The liner 54 thus permits the first sponge 56 to comprise hydrophobic (e.g., PUE) material, even when spicule penetration is not desired.

IV. Second Modified Embodiment Fluid Differentiating Wound

Dressing 102

A wound dressing comprising a second modified embodiment of the present invention is shown in FIG. 5 and generally comprises a collector assembly 106 and a transfer assembly 108. The collector assembly 106 can be similar to the collector assembly 6 with a suitable composite construction. The transfer assembly 108 comprises an elbow connector 110 placed on top of a second sponge drape 112 covering the second sponge 114. The elbow connector 110 mounts the distal end 116 of a suction tube 118, which is also connected to a vacuum source 10. A first sponge drape 120 is placed over a first, hydrophilic sponge 122 and includes a central opening 123 communicating with the second sponge 114.

Figure 5A:
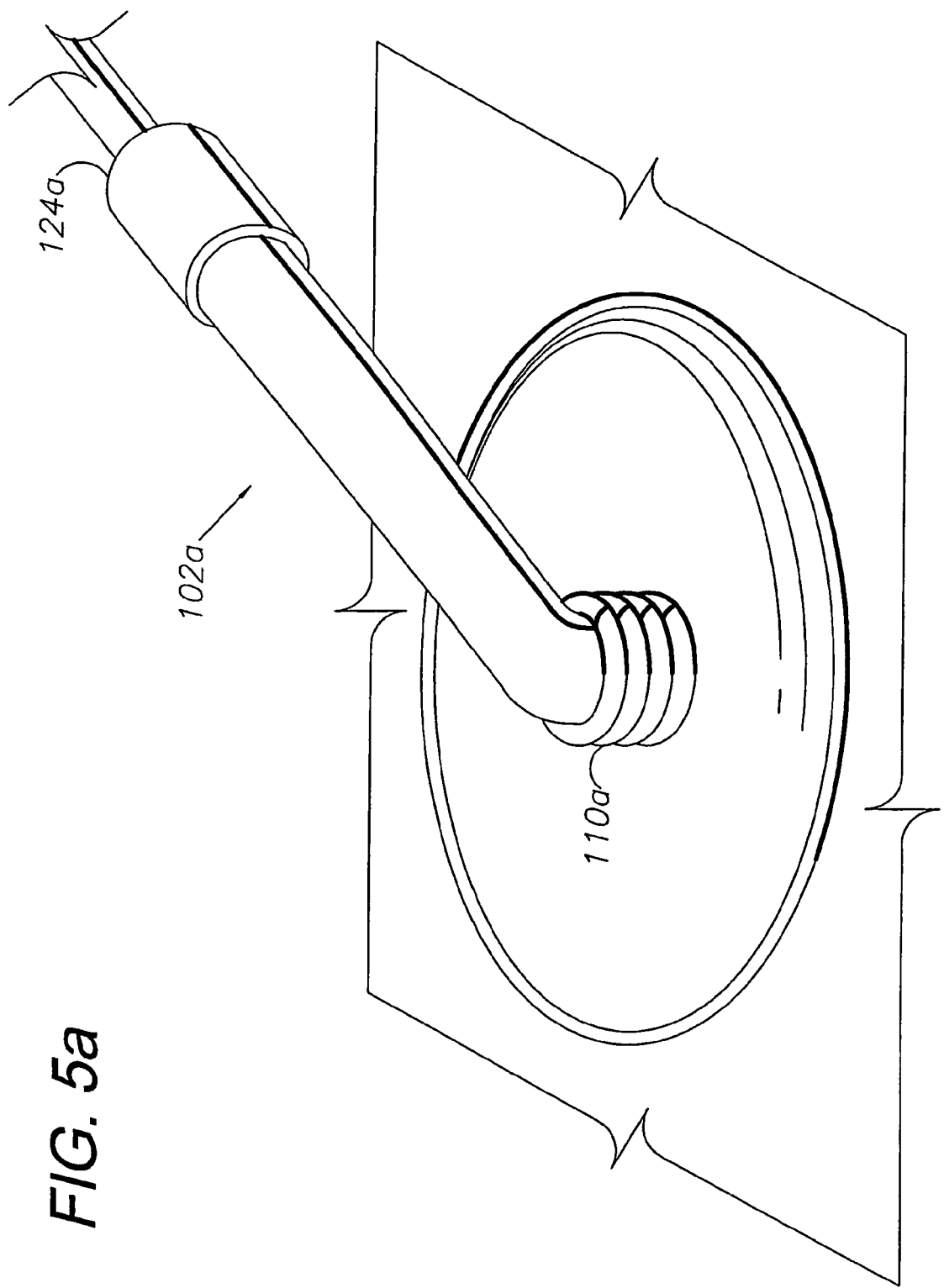
FIG. 5a is a perspective view of a variation of the embodiment shown in FIG. 5.

FIG. 5a shows an interface device 102a comprising a variation of the construction of the wound dressing 102. The device 102a utilizes a flexible, bellows-type tubing section 110a in place of the elbow connector 110 described above. A needle-free, leur lock hub 124a is mounted on the end of the tubing section 110a and functions as an injection port. It will be appreciated that the sponge 122 can be omitted from the dressing 102a whereby same can be used as a fluid inlet or outlet in various applications and on many different configurations of dressings.

V. Third Modified Embodiment Fluid Differentiating Wound Dressing 202

Figure 6:
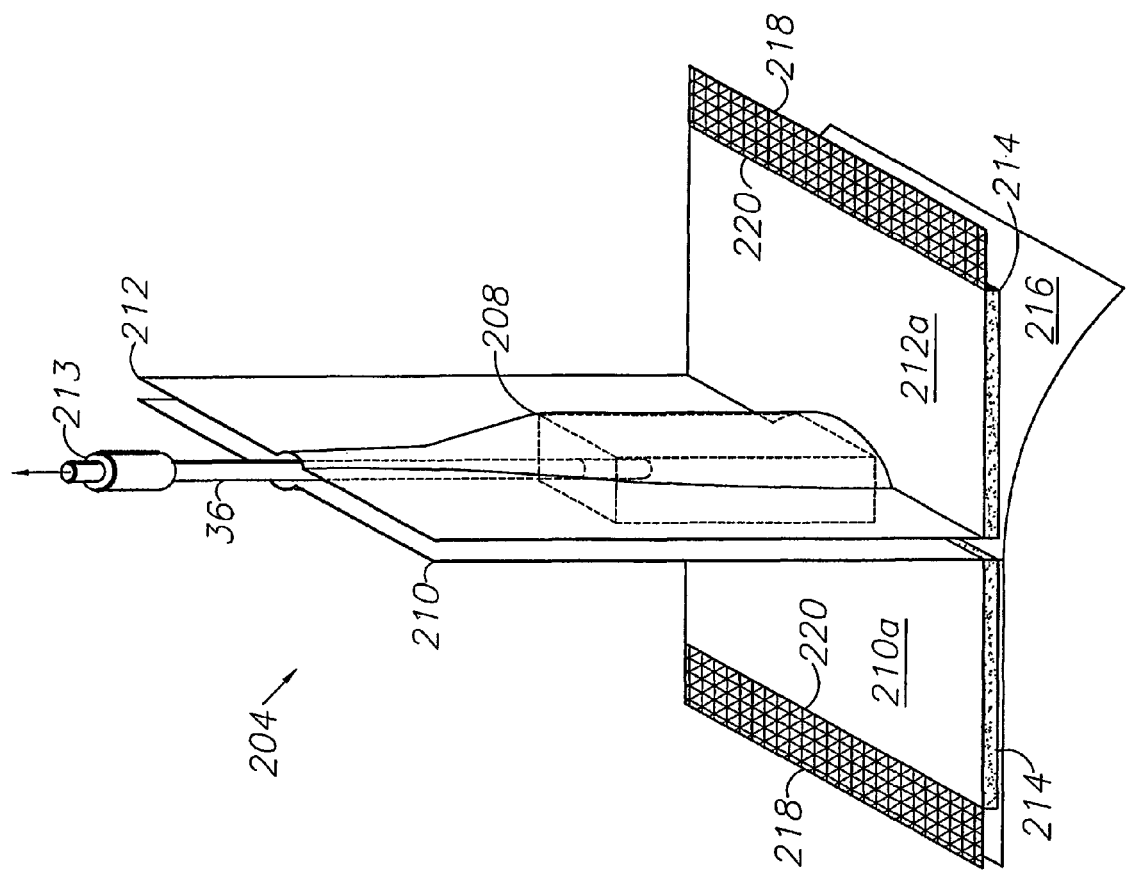
FIG. 6 is a perspective view of a transfer assembly for a composite dressing comprising a third modified embodiment of the present invention.
Figure 7:
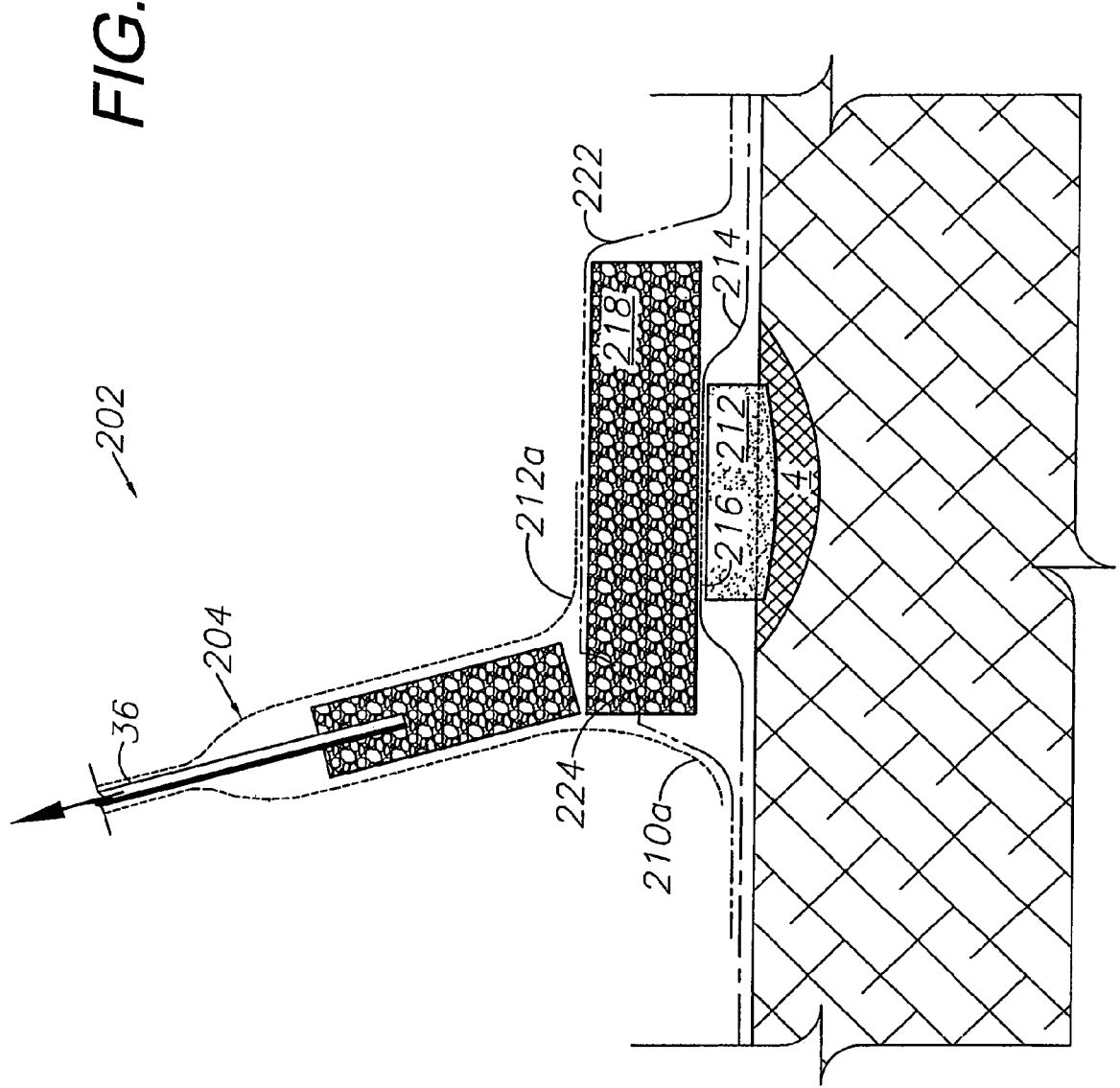
FIG. 7 is a cross-sectional view of a third modified embodiment composite dressing.
Figure 8:
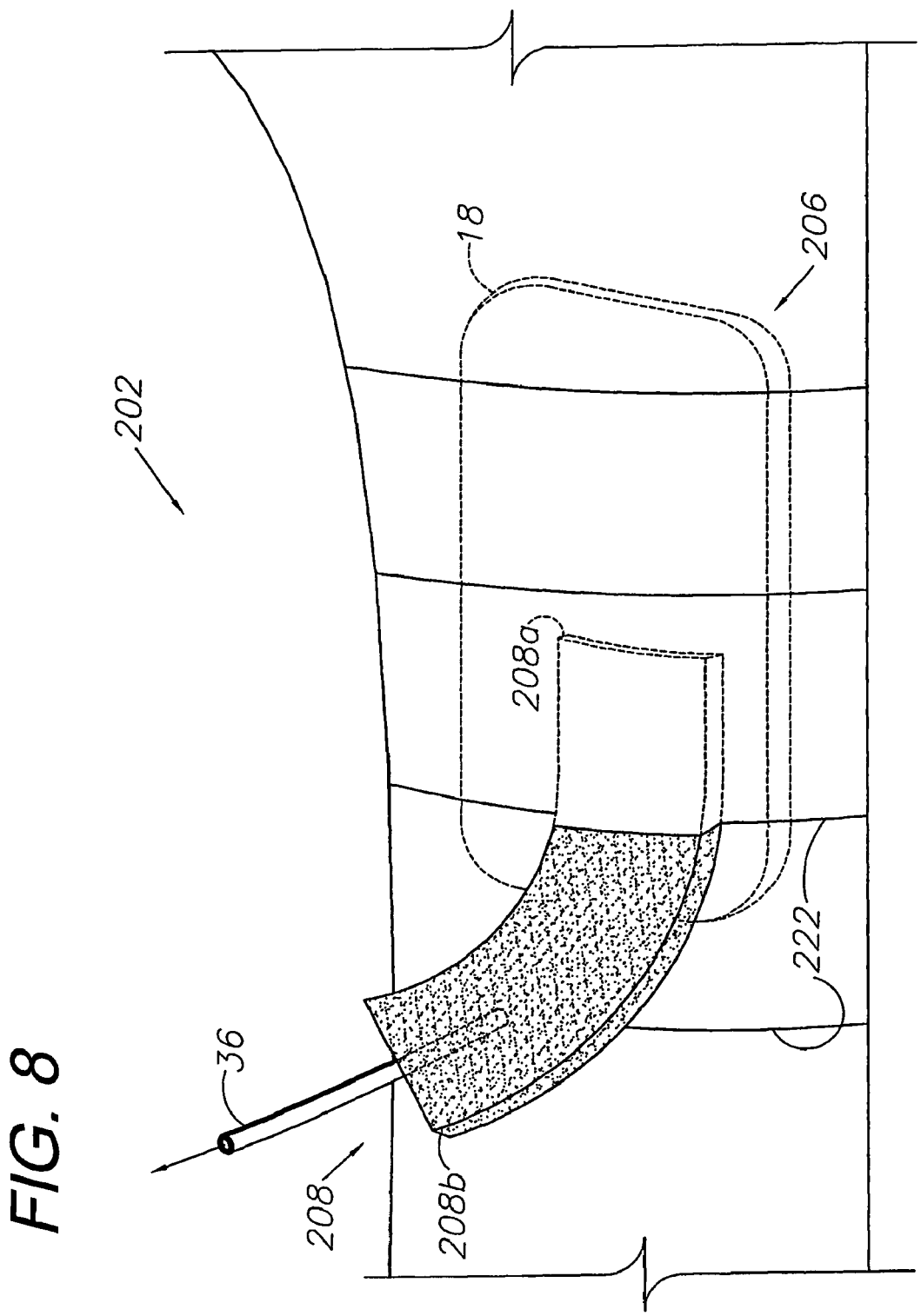
FIG. 8 is a perspective view of the third modified embodiment composite dressing.

A fluid differentiating wound dressing 202 comprising a third modified embodiment of the present invention is shown in FIGS. 6-8 and generally comprises a transfer assembly 204 (FIG. 6) adapted for mounting on a collector assembly 206 as shown in FIG. 7.

The transfer assembly 204 comprises a sponge material buffer 208 which can comprise, for example, polyurethane ether (PUE). The buffer 208 is encased in first and second drape panels 210, 212 with wings 210a, 212a respectively extending in opposite directions from the buffer 208. The wings 210a, 212a have an adhesive layer 214, which is covered by a removable backing sheet 216 prior to installation. Tab strips 218 are provided at the ends of the drape wings 210a, 212a. The tab strips 218 are attached by perforated lines 220 for easy removal upon installation. The suction tube 36 is embedded in the buffer 8 and extends outwardly from the transfer assembly 204 from between the first and second drape panels 210, 212. An optional leur-lock hub to 13 is mounted on the end of the tube 36 for injection port applications.

The transfer assembly 204 is adapted for mounting on a collector assembly 206 (FIG. 7), which is similar to the collector assembly 6 described above. An opening 224 is formed in a second drape 222 which overlies a second sponge 218. With the backing sheet 216 peeled away, the adhesive layer 214 on the drape panel wings 210a, 212a secures the transfer assembly 204 in place whereby the buffer 208 is in communication with the second sponge 218 through the opening 224. An optional first sponge 212 can be placed on the wound 4 and covered with drape 214 with an opening 216 formed therein. The dressing 202 can also be utilized with a single sponge for the collector assembly 206.

FIG. 8 shows an application of the dressing 202 wherein the transfer assembly 204 is mounted over a medial or interior portion 218a of the second sponge 218. A first end 208a of the buffer 208 can be folded substantially flat on top of the second drape which overlies the second sponge 18. A second end 208b of the buffer 208 extends outwardly from the collector assembly 206. The buffer 208 can flex in response to pulling forces tugging on the suction tube 236. The dressing 202 as shown in FIG. 8 is wrapped with drape strips 222, which are adapted for encircling an extremity of a patient. Thus, the buffer first end 208a is secured by a drape strip 222 as shown. The drape strips 222 can be utilized for applying a compressive force to the dressing 202. In operation, evacuating the dressing 202 causes portions of it to shrink, compress and collapse under the pressure gradient, thus providing a visual indication of its performance.

VI. Fourth Modified Embodiment Fluid Differentiating Wound

Dressing 302

Figure 9:
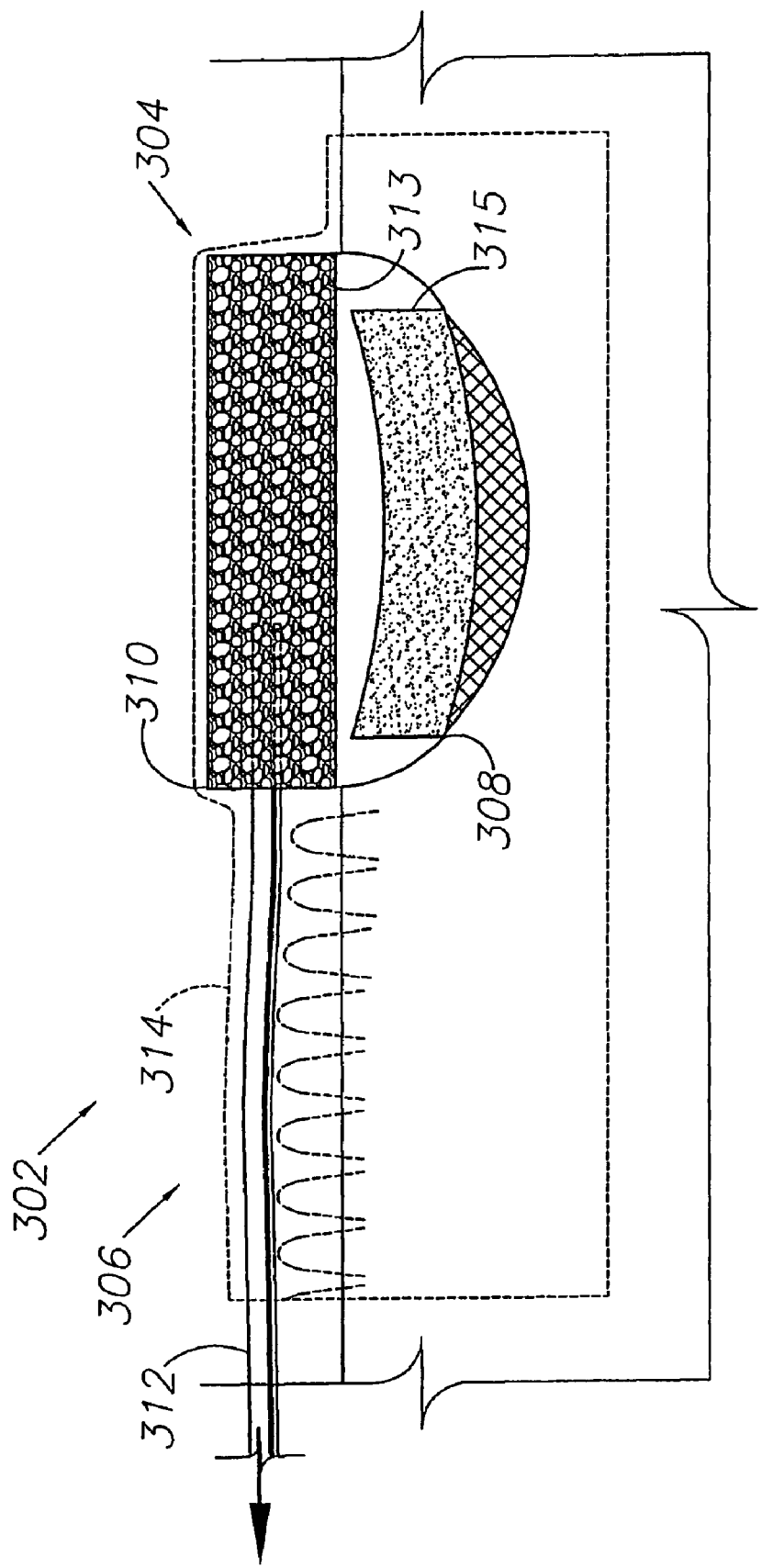
FIG. 9 is a perspective view of a composite dressing comprising a fourth modified embodiment of the present invention.

FIG. 9 shows a fluid differentiating wound dressing 302 comprising a fourth modified embodiment of the present invention. The dressing 302 includes a collector assembly 304 and a transfer assembly 306. The collector assembly 304 includes first and second sponges 308, 310. The first sponge 308 is mounted on the wound and can comprise, for example, a hydrophilic foam material as described above. The second sponge 310 can be mounted directly on the first sponge 308 (optionally separated by a drape) and can receive a tube 312 connected to a vacuum source. The second sponge 310 can include an overhang 313 extending beyond the first sponge 308 for providing a compression chamber 315 as described above. A drape 314 is placed over the collector assembly 304 and the tube 312. The drape 314 is folded over the tube 312 whereby same is spaced outwardly from the skin, thus providing an effective, fluid-tight seal around the tube 312.

VII. Vacuum-Fixed Wound Therapy Method

Figure 10:
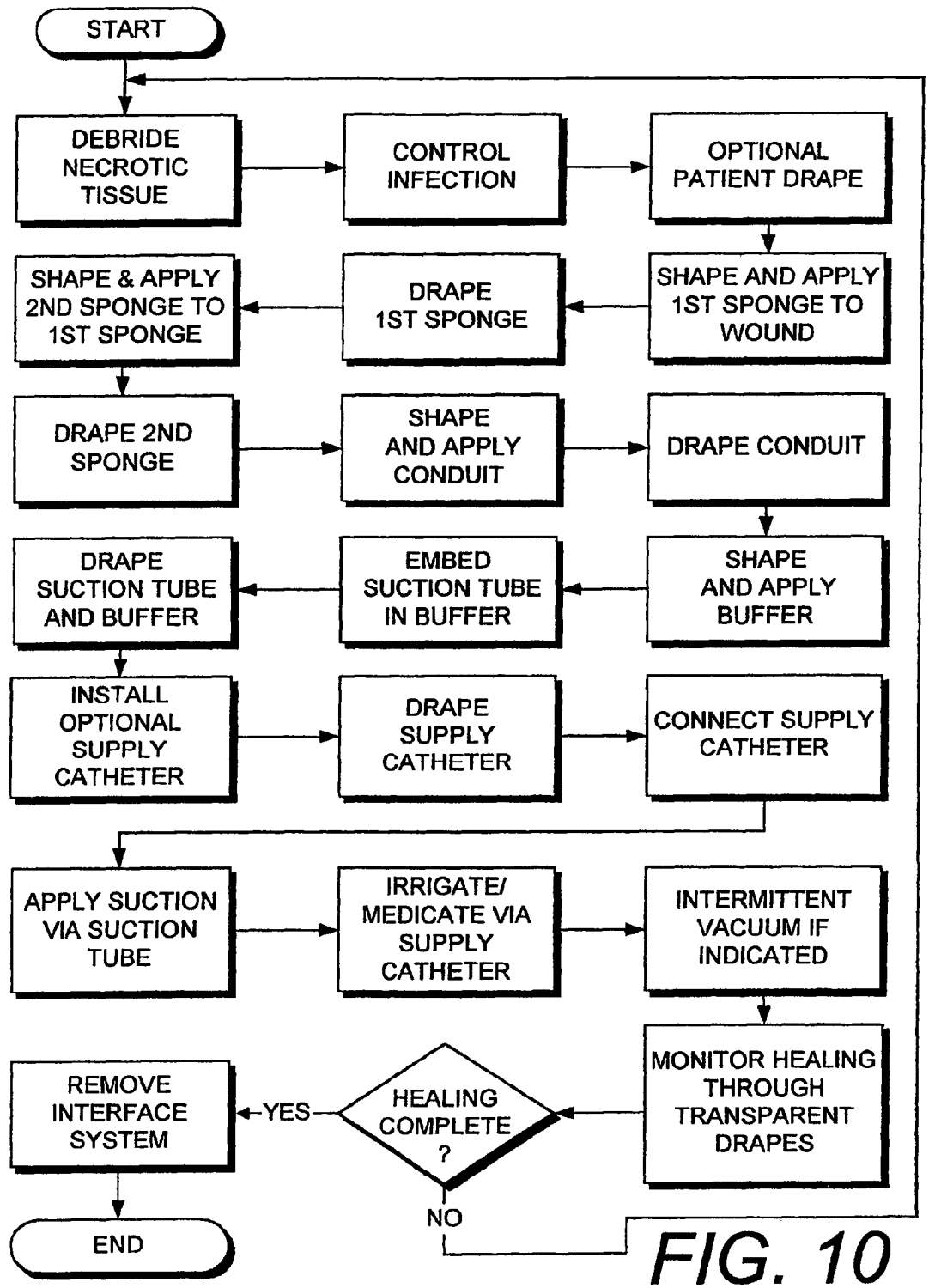
FIG. 10 is a flow diagram of a vacuum-fixed wound therapy method embodying the present invention.

FIG. 10 shows a wound therapy method embodying the present invention. The method can be performed with one or more of the systems discussed above, including the vacuum-fixed dressings 3, 53, 102, 202 and 302. The method can also be performed with a wide variety of variations on the systems and dressings disclosed above.

VIII. Fifth Modified Embodiment Wound Therapy And Tissue Management System 402

Figure 11:
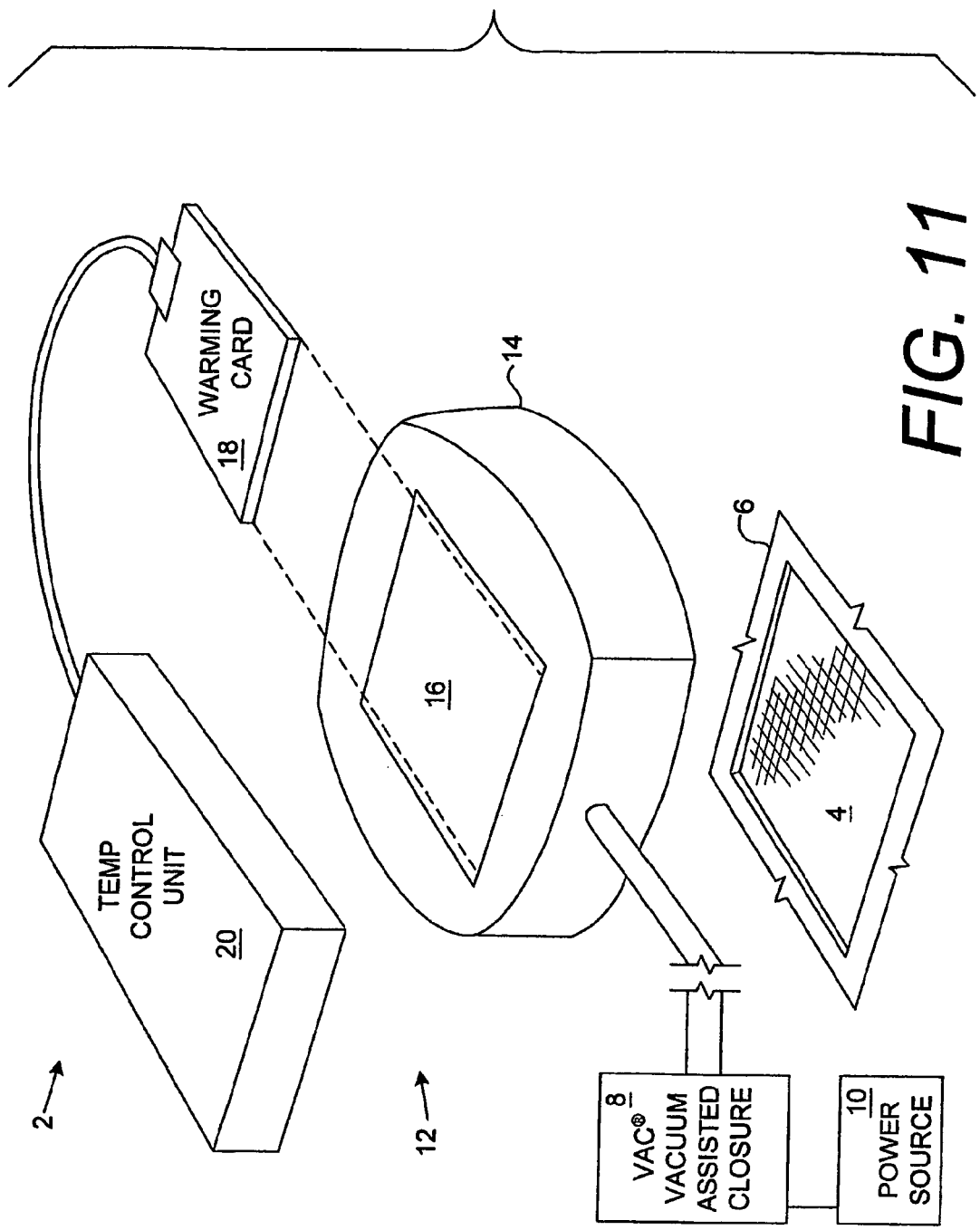
FIG. 11 is an exploded view of a wound treatment system with vacuum, heat and fluid assistance.

FIG. 11 shows a wound therapy and tissue management system 402 comprising a fifth modified embodiment of the present invention. The system 402 includes a dressing 404 placed on a wound 406. Any of the dressing systems discussed above can be utilized. The enclosure 414 is placed over the wound site 406 and includes an opening 416 extending therethrough and adapted for receiving a warming card 418 in covering relation thereover. The warming card 418 is operationally connected to a temperature control unit 420. A vacuum assisted closure unit 408 is fluidically connected to the enclosure 414 by a suitable suction tube and in turn is connected to a power source 410.

In operation, the warming card 418 is heated and raises the temperature within the enclosure 414 to promote healing. The vacuum assisted closure 408 functions as described above to remove effluent and to promote healing in cooperation with the warming card 418. Warming cards and other components for use in connection with this embodiment of the invention are available from Augustine Medical Products, Inc.

IX. Sixth Modified Embodiment Wound Therapy and Tissue Management System 502

Figure 12:
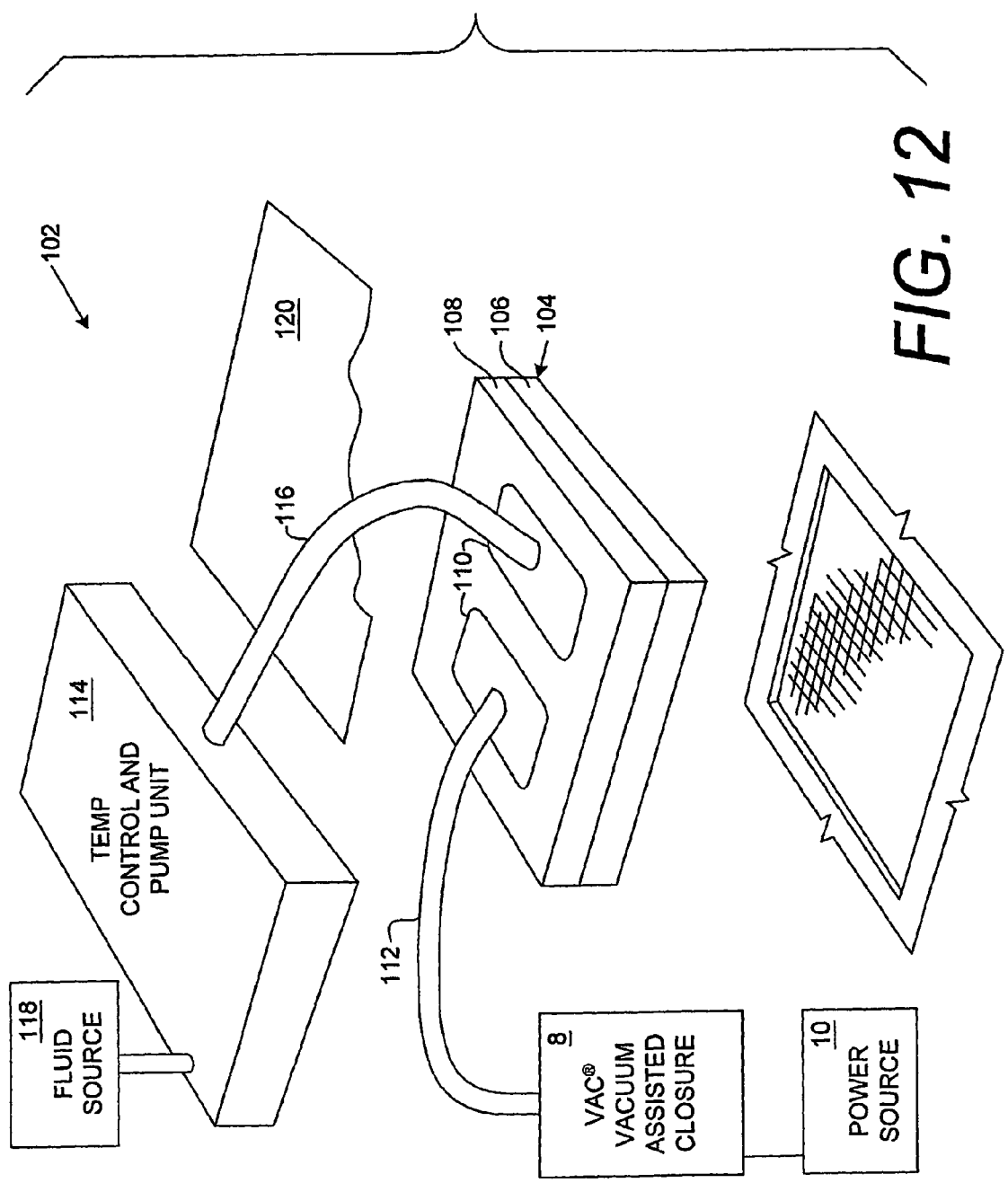
FIG. 12 is an exploded view of another wound treatment system with vacuum, heat and fluid assistance.

FIG. 12 shows a wound therapy and tissue management system 502 comprising a sixth modified embodiment of the present invention. The system 502 is similar to the system 402 described above. A composite dressing 504 is comprised of first and second layers 506, 508. A fluid source 518 communicates with a temperature control and pump unit 514 and provides influx to the system 502.

X. Seventh Modified Embodiment Wound Therapy and Tissue Management System 602.

FIG. 13 shows a wound therapy and tissue management system 602 comprising a seventh modified embodiment of the present invention. The system 602 is similar to the systems 402 and 502 described above. A transfer element 604 is covered by a drape 620, which mounts a film 616 adapted for receiving a warming card 618.

XI. Test Data

Figure 14B:
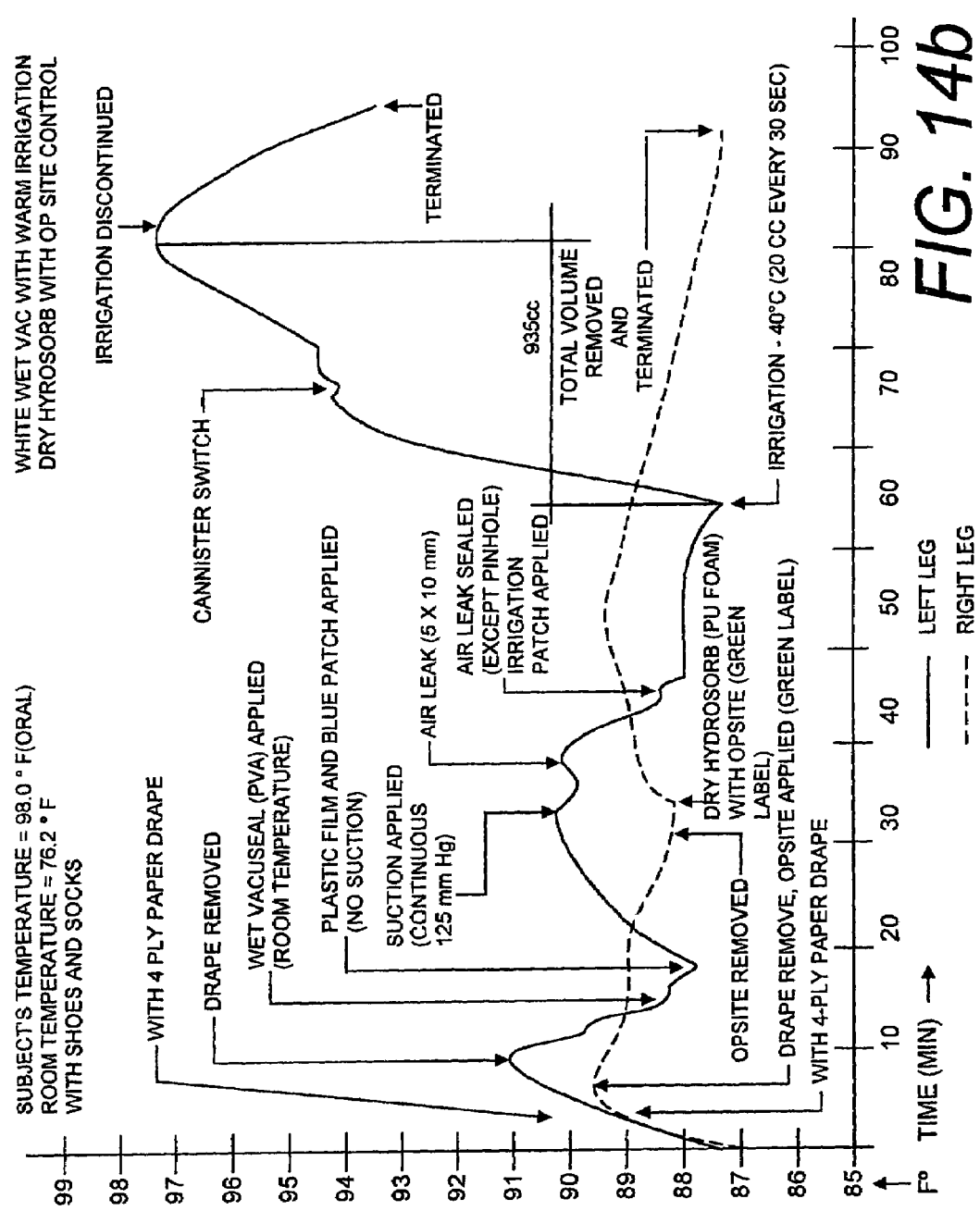
Figure 14C:
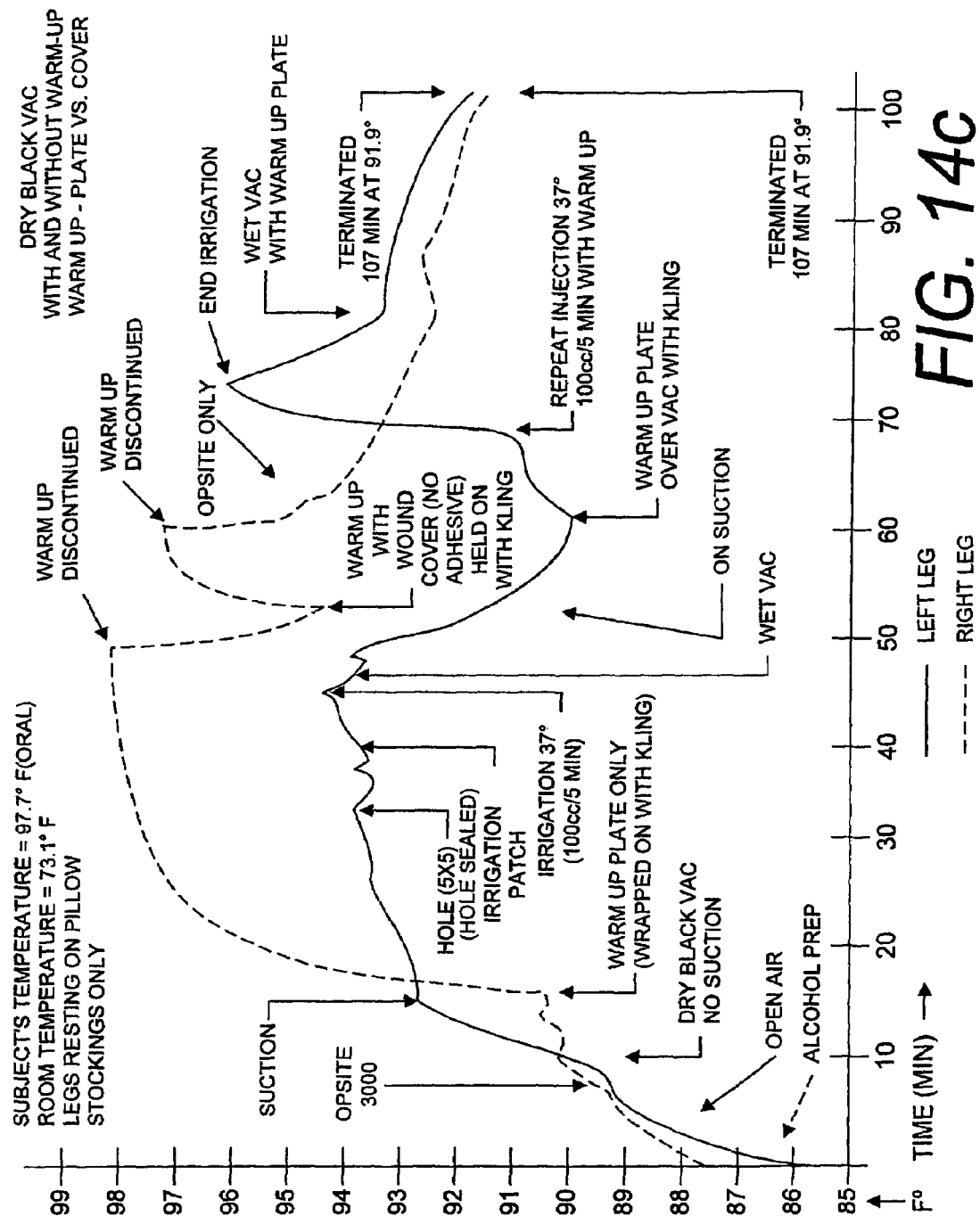
Figure 14D:
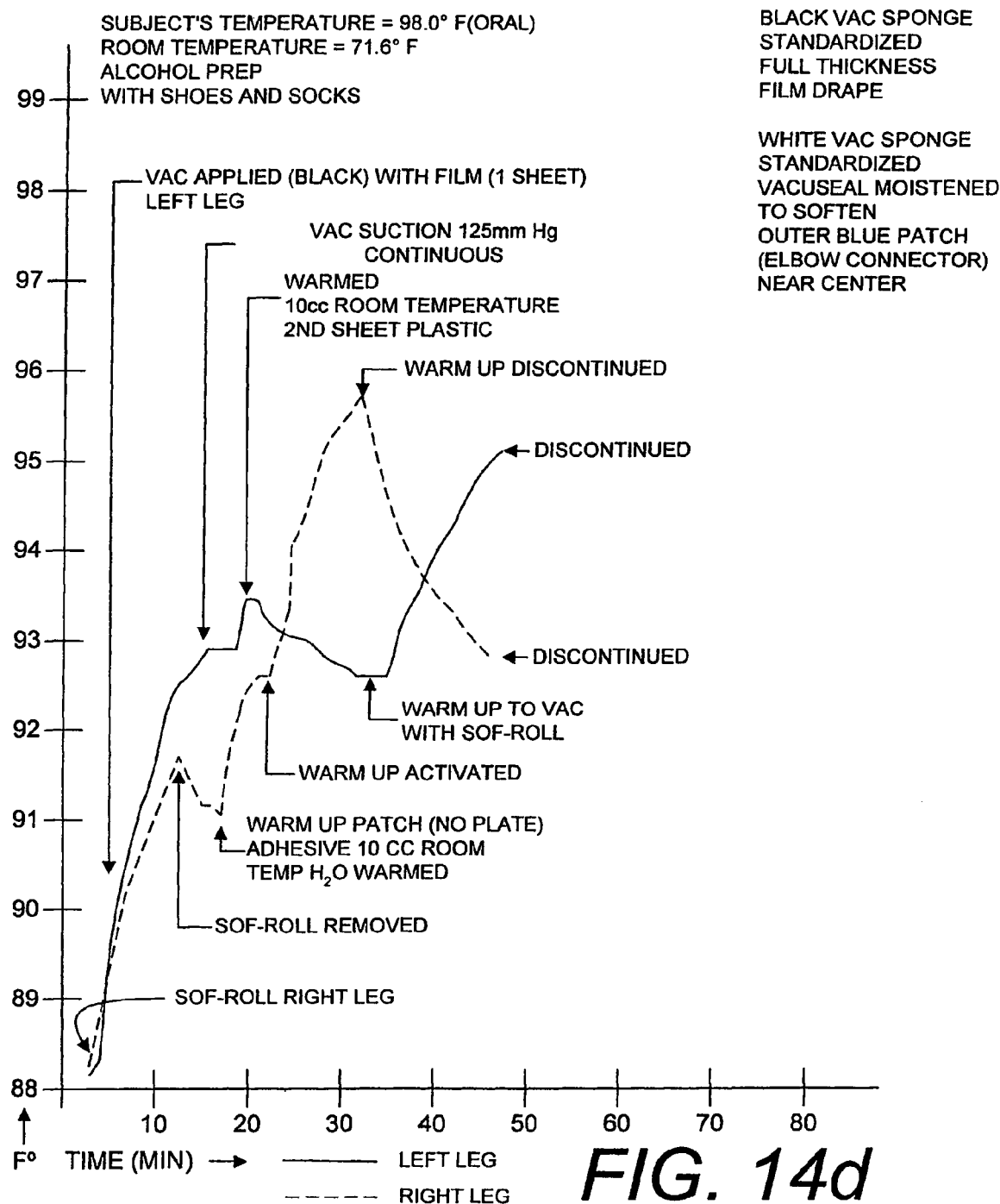

FIGS. 14a-14d shows the results of tests performed with the dressing systems and methodologies discussed above and variations thereon. FIG. 14a shows system performance (time and temperature) with a dry PUE hydrophobic sponge material. FIG. 14b shows system performance with a wet PVA hydrophilic sponge material. FIG. 14c shows performance with an irrigated PUE hydrophobic sponge material with a warm-up plate (heating card) and a cover. FIG. 14d shows system performance with both PUE hydrophobic sponge material and PVA hydrophilic sponge material.

XII. Wound Therapy and Tissue Management System 702

Figure 15:
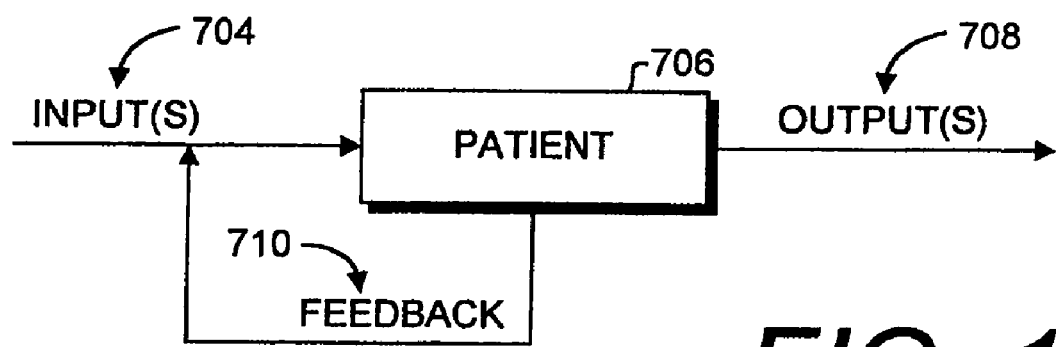
FIG. 15 is a block diagram of a wound therapy and tissue management system comprising an eighth alternative embodiment of the present invention.
Figure 16:
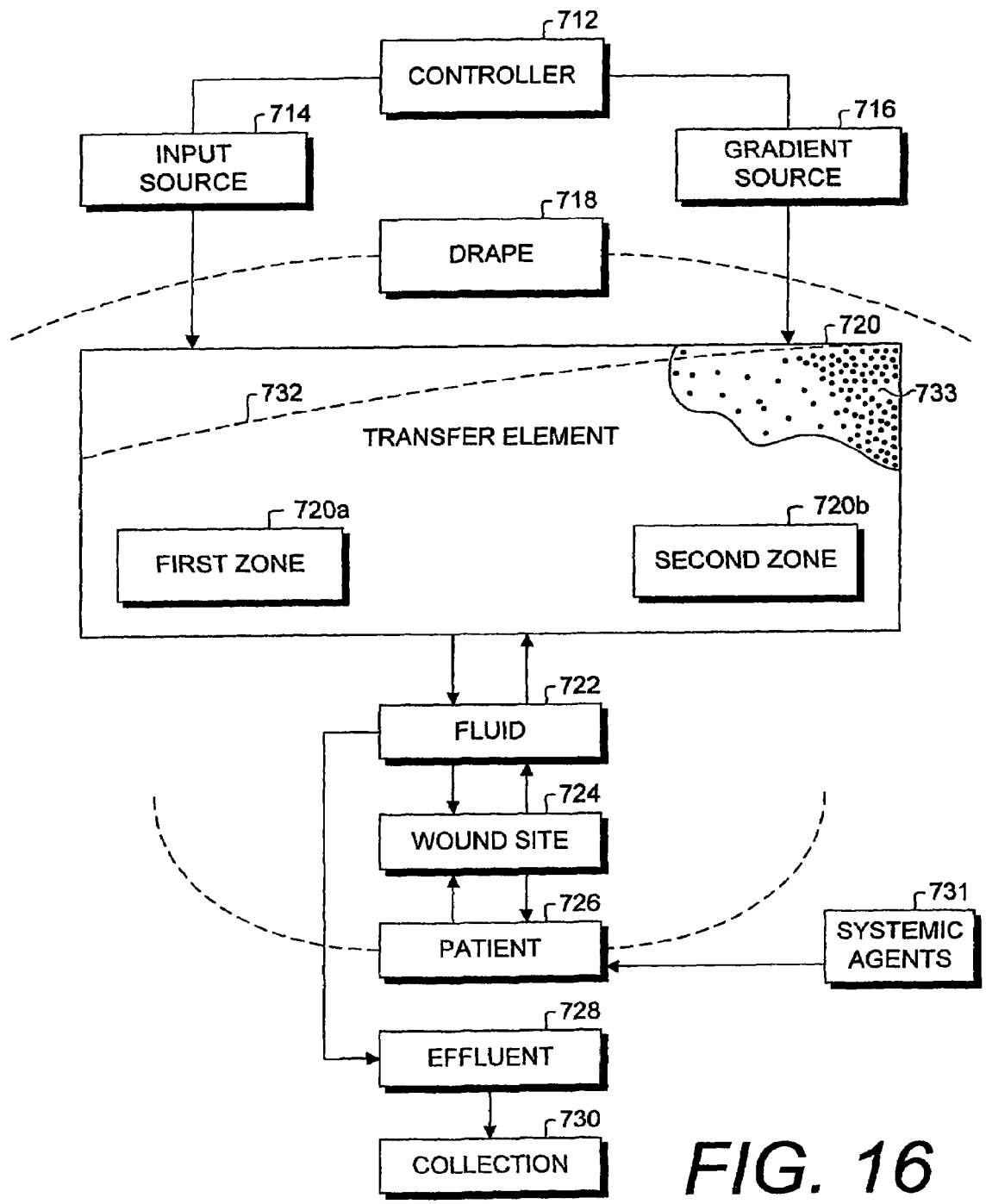
FIG. 16 is a schematic diagram of the eighth alternative embodiment wound therapy and tissue management system.

FIGS. 15 and 16 show a wound therapy and tissue management system 702 comprising an eighth modified embodiment of the present invention. The system 702 is shown schematically in FIG. 15 and consists of inputs 704, the patient 706, outputs 708 and a feedback loop 710. The inputs 704 can comprise virtually any matter or energy deemed appropriate for the treatment protocol by the health-care practitioner. For example, various irrigation fluids, growth factors, antibiotics, anesthetics, etc. can be input to the patient 706. Still further, the inputs can comprise various forces and energy forms whereby a matter/energy gradient is established with respect to the patient 706.

For example, negative pressure from a suitable vacuum source (such as a VAC unit available from Kinetic Concepts, Inc. of San Antonio, Tex.) can be an input for creating a negative pressure gradient across the system. Likewise, positive pressure from a suitable fluid pump can be input to establish a positive pressure gradient across the system. Other forces can provide electromagnetic, electrical, mechanical and thermal gradients.

The system 702 monitors performance of the patient 706 and controls the inputs 704 interactively in response thereto. Parameters which could be monitored for feedback purposes included moisture levels, temperature, bacteria levels, fluid pressure, etc. The presence or absence of particular elements and compounds can also be sensed, monitored and acted upon. For example, is widely known that oxygen is an important factor in wound healing. Studies have shown that reepithelialization and collagen production are best achieved by varying the oxygen supply. Thus, the oxygen level within the enclosed, wound site environment can be monitored and the oxygen levels therein either increased or decreased as necessary to promote healing. Other controllable parameters include the pH factor and the moisture concentration of the wound environment. Various suitable monitoring means can be employed, including electronic sensors, visual indicators, color-change substances, etc.

The output from the patient can consist of fluid, such as effluent from the wound site, irrigation fluid removed in the process of flushing the wound site, and other matter and energy. An important function of the system is the removal of toxins and bacteria, which can be flushed from the wound site in a liquid or fluid solution.

FIG. 16 is a block diagram of the system 702, showing the components thereof in greater detail. A programmable controller 712 can be preprogrammed to operate the system according to predetermined protocols. The controller 712 is connected to and controls the operation of the input source 714 and the gradient source 716. The input source 714 can comprise any suitable matter or energy for input to the system 702, including various fluids, medications, thermal energy, mechanical forces, temperature, etc., as discussed above. The gradient source is likewise unlimited. For example, pressure gradients (both positive and negative) are particularly suitable for controlling the operation of the system 702 for draining wounds. Other types of gradients include temperature, osmotic, oncotic, pH, oxygen demand, bacteria concentrations, etc., as discussed above.

A gradient source 716 can comprise any suitable device for establishing a gradient. For example, a vacuum source can be utilized for creating a negative pressure gradient. A pump can be utilized for creating a positive pressure gradient. A drape 718 is placed in covering relation over a transfer element 720. The drape 718 can comprise any of the film materials discussed above and can be permeable, semi-permeable or impervious.

The transfer element 720 includes a first zone 720a with a first set of fluid flow characteristics and a second zone 720b with a second set of fluid flow characteristics. Such fluid flow characteristics can be a function of material, thickness, porosity, permeability, and sponge material attraction to proteins, fat cells and other substances. The zones 720*a,b* can be formed by providing layers of the material, by providing varying thicknesses, by interspersing a first material within a second material in predetermined configurations, etc. Still further, the first and second zones can be formed by subjecting the transfer element 720 to an electromagnetic field.

The first and second zones 720*a,b* can also be formed by varying the density of the transfer element 720, as indicated by the dashed line 732 (FIG. 16). Line 732 represents compressed material (e.g., foam) along one edge and expanded material in the second zone 720*b*. Such density gradients can be achieved by compressing the material or by heat-setting same in a manufacturing process. Transfer element 720 edges can also be compressed when the dressing is applied to achieve a desired density gradient. Material thickness can also be utilized to provide a flow coefficient gradient. In this case line 732 could represent a tapering of the transfer element 720 across the first and second zones 720*a*, 720*b*. A marbling effect with a material concentration gradient is shown at 733, with greater concentration along an edge and decreasing concentration towards interior portions of the transfer element 720, or vice-versa. Constructing the first and second zones 720*a*, 720*b* of different materials with different respective flow coefficients could also achieve a desired flow gradient.

Medications and other substances can be applied to the transfer element materials to alter the flow characteristics thereof. Systemic agents 731 can be administered to the patient 726.

Fluid 722 can be introduced into the wound site 724 from the inputs 714 and its flow pathways can be controlled by the gradient source 716. For example, sponge materials with different flow characteristics can be configured to direct fluid (either gas or liquid) in predetermined flow patterns through the transfer element 720. Effluent 728 from the patient 726 is withdrawn from the wound site 724 and evacuated to a collection receptacle 730.

XIII. Wound Therapy and Tissue Management Methodology

Figure 17:
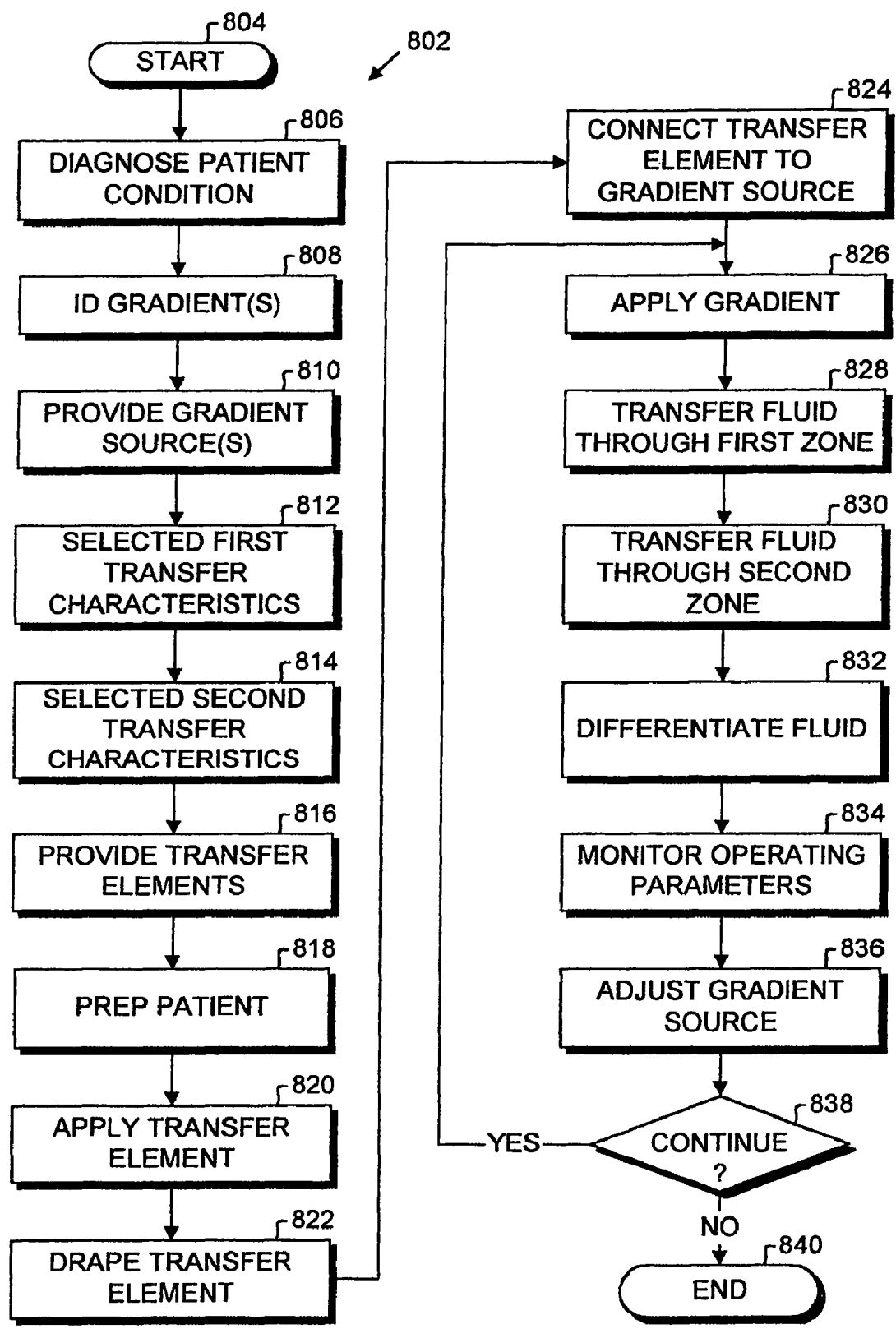
FIG. 17 is a flowchart of a wound and therapy and tissue management methodology embodying the present invention.
Figure 18:
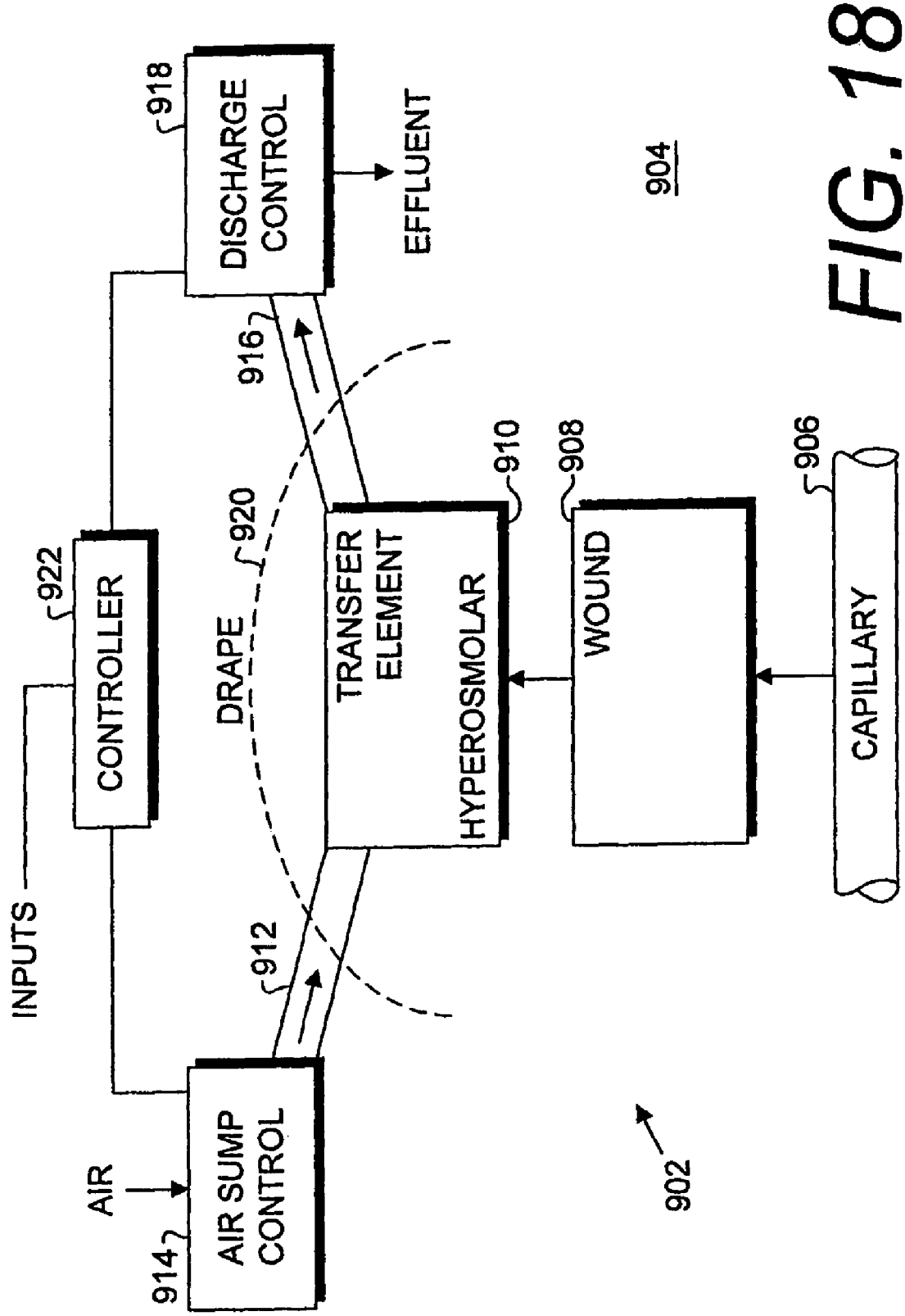
FIG. 18 is a block diagram of a wound therapy and tissue management system comprising a ninth alternative by the present invention.

FIG. 17 shows a flowchart for a wound therapy and tissue management methodology embodying the president mentioned. From Start 804, the method proceeds to Diagnose Patient Condition 806. Based on the diagnosis, a treatment protocols selected. The protocol includes an identification of a gradients to be controlled by the methodology. For example, protocols involving vacuum-assisted wound drainage will generally include a negative pressure gradient. Additional possible gradients are discussed above. It will be appreciated that virtually unlimited combinations of gradients can be formed in the system 702. Moreover, the timing of the gradient control can be varied as needed to achieve desired treatment results. For example, collagen production and reepithelialization can be promoted by hyperbaric oxygen treatment procedures, such as alternating elevated and reduced oxygen concentrations. Suction/compressive pressures can also be alternated to stimulate tissue growth.

Gradient sources are provided at 810 and can comprise vacuum/suction, fluids, medications, oxygen and various other matter and energy. Gradients can also be formed utilizing energy sources, such as thermal, mechanical force, etc. First and second transfer characteristics are selected at 812, 814 respectively. A transfer element(s) is provided at 816 and includes the transfer characteristics selected at 812, 814. The patient is prepared at 818. Patient preparations can include any suitable medical procedures, such as debriding the wound, etc.

The transfer element is applied at 820 and draped at 822. The transfer element is connected to a gradient source at 824 and the gradient is applied at 826. Fluid is transferred through the first transfer element zone at 828 and through the second transfer element zone at 830. It will be appreciated that such transfer zones can be adapted for directing the fluid along certain pathways to achieve desired results, such as evacuation of exudates. The fluid is differentiated (e.g., liquids, gases or liquids and gases are separated) at 832.

The operating parameters are monitored at 834 and the gradient source(s) are adjusted accordingly add 836. Thereafter a "Continue?" decision box 838 is reached. If affirmative, the method returns to Apply Gradient 826 and operation continues with the adjusted gradient parameters. A negative decision at 838 leads to a termination of the procedure (i.e., "End") at 840.

XIV. Osmotic Gradient Wound Therapy and Tissue Management System 902 and Methodology FIGS. 18-21 show a wound therapy and tissue management system 902 and methodology utilizing a controlled osmotic gradient. A patient 904 includes capillaries 906 which provide fluid, such as serum and blood, to a wound 908. Such fluid passes to the transfer element 910. An air sump control 914 communicates with the transfer element 910 through an air sump conduit 912. A discharge control 918 communicates with the transfer element 910 through a discharge conduit 916. The controls 914, 918 are interactively controlled by a controller 922, which is adapted to receive control input signals. Such input signals can comprise, for example, preprogrammed inputs, feedback signals (FIG. 15), etc. The input signals can originate at sensors associated with the system 902 and with the patient 904. Such inputs can effectively control the osmotic gradient to achieve desired fluid, solvent and solute (e.g., toxin) transfers. For example, the primary external substance input can comprise relatively dry ambient air. Air movement through the system 902 tends to collect moisture for discharge as water vapor.

The system 902 is covered by a drape 920, which can comprise various semi-permeable and impervious materials as required by fluid flow considerations and various applications. For example, an impervious drape 920 tends to block air from the system 902 and permit entry of same only through the air sump control 914.

Figure 19:
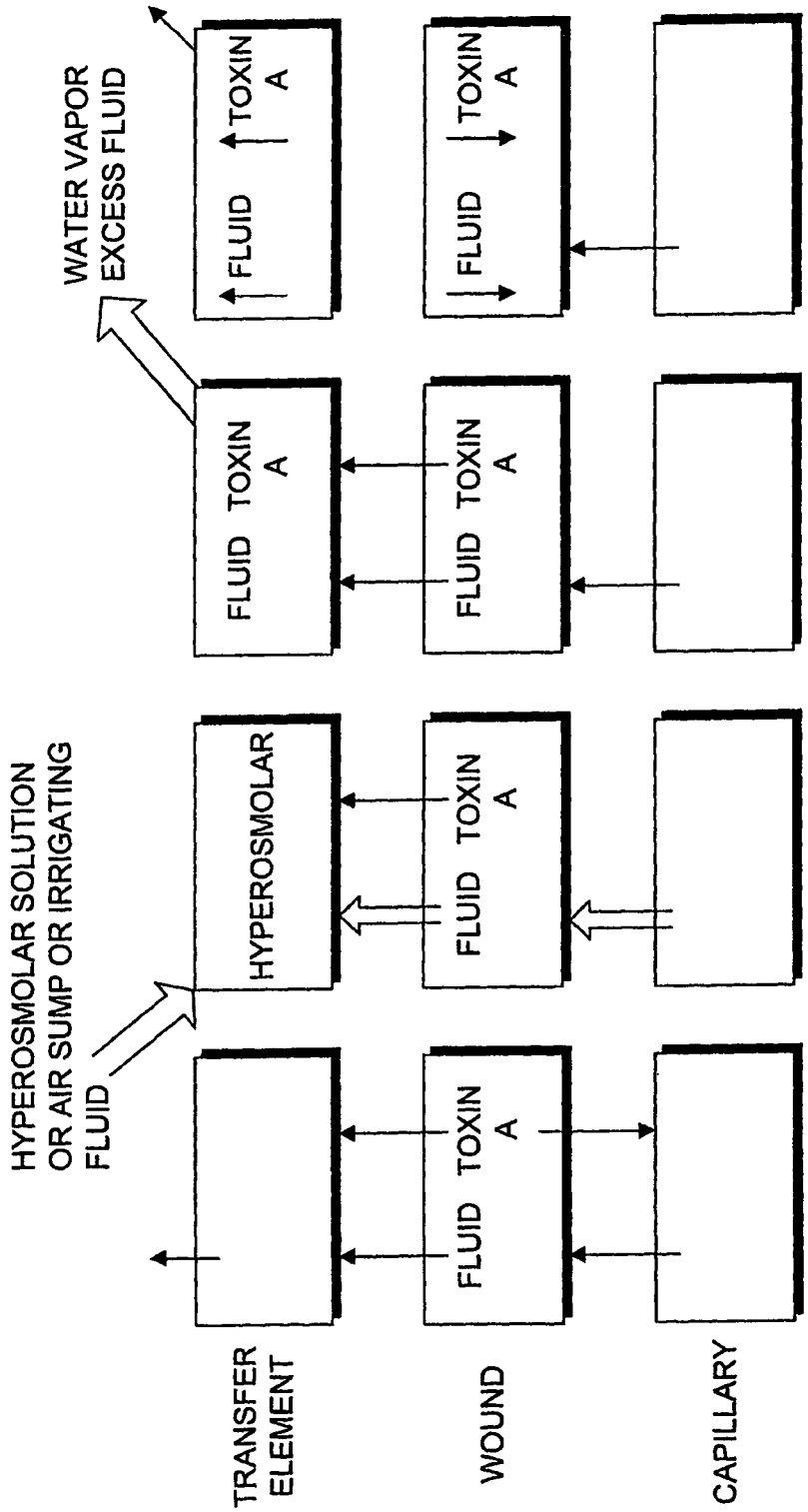
FIG. 19 is a diagram showing various phases in a hyperosmolar or air-sump system embodying the present invention.

FIG. 19 shows a hyperosmolar or air-sump system. Phase 1 represents a steady-state or increasing-toxin A condition and a concomitant increasing movement of toxin A back into the patient. In phase 2 a hyperosmolar solution or air sump is introduced. This gradient draws fluid from the capillaries to replace the fluid moved out of the wound into the transfer element carrying toxin A with it and decreasing movement of toxin A into the patient. Alternatively or in addition, warmed irrigating fluid can be introduced into the transfer element in phase 2. The advantages of warming the transfer element and wound site in this manner include vasodilation, increase in cell motility and an increase in phagocytosis. For example, irrigating fluid warmed to approximately 40 degrees centigrade has been shown to remove the inhibitory effect of chronic wound fluid on cell culture motility and proliferation.

In phase 3, ongoing administration of this gradient continues these fluxes as water vapor is removed and dry air is sumped. In phase 4 is results in a new steady-state condition with lower levels of toxin A in the wound (and the patient) and increased fluid and toxin A in the transfer element that is continuously evacuated.

Figure 20:
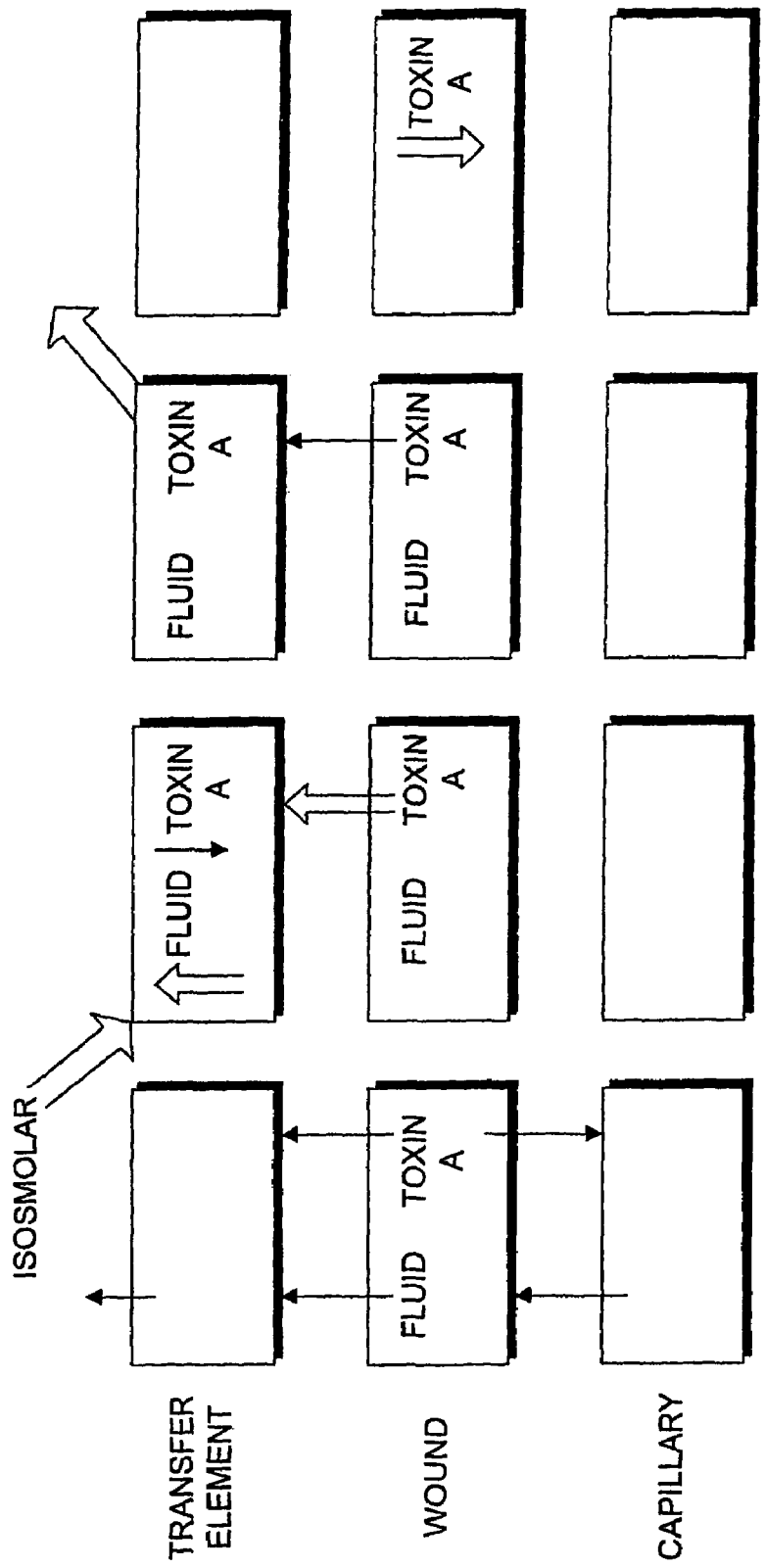
FIG. 20 is a diagram showing various phases in an osmolar or isotonic flush or rinse system embodying the present invention.

FIG. 20 shows an isomotic or isotonic flush or rinse methodology. In phase 1 there is a steady-state (or increasing toxin A level) condition with fluid (liquids) moving out from the wound to the transfer element being replaced by serum exudate from the capillary. Evaporative loss from the transfer element is kept to a minimum by application of a drape material.

In phase 2, an isomotic rinse is introduced, increasing the fluid content of the transfer element and decreasing the concentration of toxin A, enabling a diffusion of toxin A from the wound into the transfer element. In phase 3, as this fluid is withdrawn, it also removes toxin A, enabling a continued diffusion of toxin A out of the wound. In phase 4, the resulting condition is fluid equilibrium and decreased concentration of toxin A in the wound. As this situation reverts to phase 1, the flush or rinse is repeated at intervals.

FIG. 21 shows a hypo-osmolar or heavy drape system. In phase 1 steady-state conditions generally exist with some evaporative loss of fluid (water vapor). In phase 2, small amounts of hypo-osmolar fluid are introduced, or a cover/drape is placed over the transfer element with a heavy drape completely blocking evaporative loss, thus adding "free water" to the system. This reverses the outward flow of fluid from the wound.

In phase 3 this increased fluid in the wound allows the total amount of toxin A to also accumulate in the wound. In phase 4 this increase of fluid and toxin A in the wound without any egress produces movement of fluid (edema) and toxins (cellulitis) back into the patient and into the lymphatics.

XV. Generic Model and Additional Modified Embodiments

Figure 22:
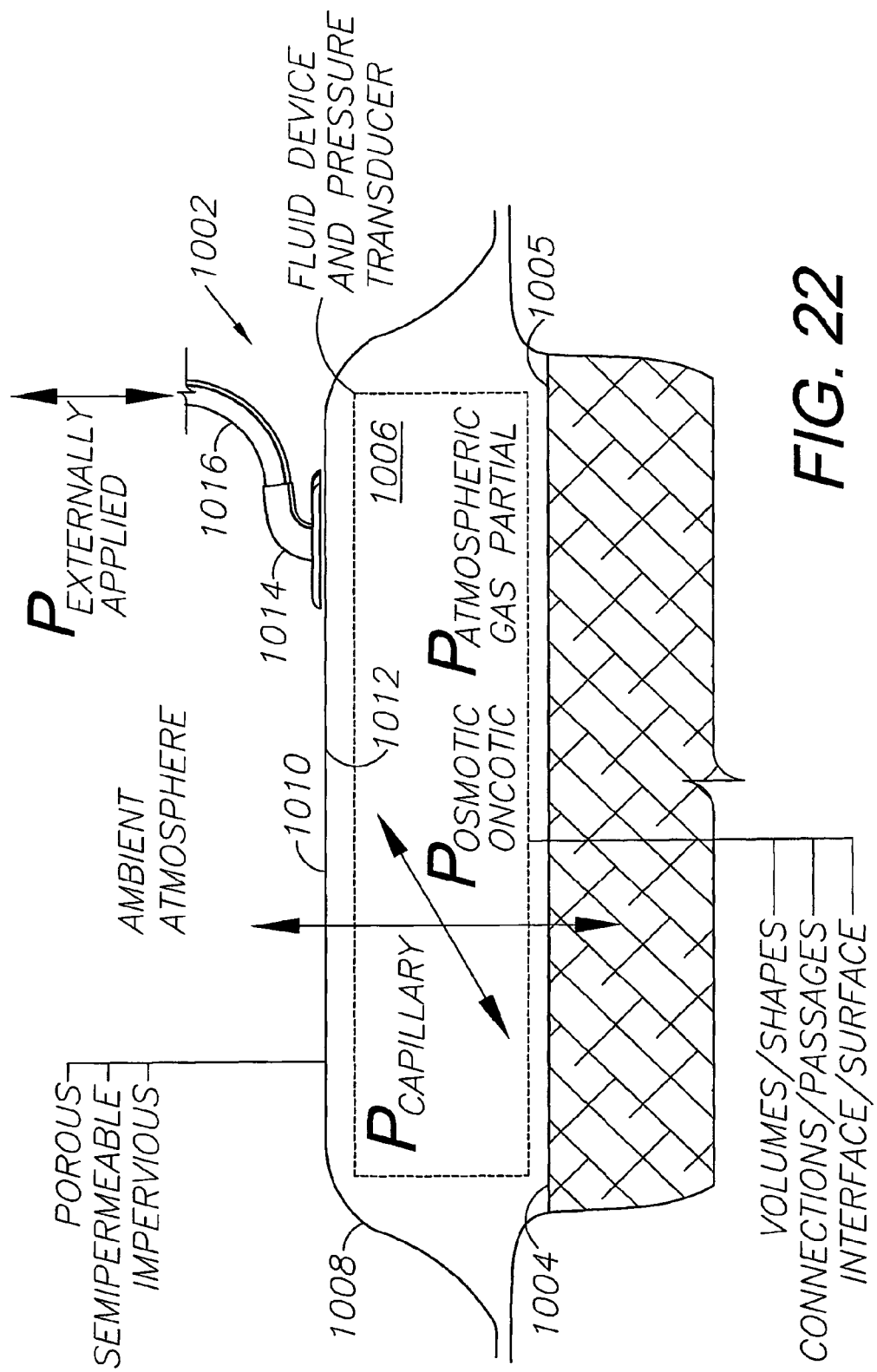
FIG. 22 is a diagram showing a generic model of a gradient wound treatment system.

FIG. 22 shows a generic model of an osmotic transducer system 1002 for treating a wound 1004 by manipulating the gaseous, liquid and solid components in such a way as to create pressure gradients in fluid elements that produce useful fluid flow. The system 1002 is shown applied to an exposed tissue layer 1005. A pressure transducer component 1006 can comprise a porous hydrophobic material, such as polyurethane ether (PUE) foam, or a hydrophilic material, such as polyvinyl alcohol (PVA) foam. Alternatively, various other materials with suitable fluid mechanics and handling properties can be utilized, including naturally-occurring or man-made materials, or both.

The pressure transducing function of the component 1006 involves several different kinds of pressures from different sources, which are generally designated P in FIG. 22. For example, gas components can be changed or gas pressure relative to ambient air can be changed, producing gradients. Osmotic and/or oncotic liquid pressures can be involved in causing patient fluid to flow through the system 1002. Capillary pressure is a function of the spaces in the solids or materials comprising the transducer component 1006. Moreover, the tissue layer 1005 also functions as a transducer for pressure P. Externally-applied pressure P can originate at a negative pressure source, such as a vacuum pump, or at a positive pressure source, such as a fluid pump.

In its simplest form (e.g., the generic model shown in FIG. 22) the transducer system 1002 includes a base element 1008 generally comprising the transducer component 1006 partly surrounded by a cover 1010. The fluids acted on can be gaseous or liquid. Many applications will involve both. The base element 1008 communicates and interacts with its environment. Gradients are actively established by the containment and manipulation of the base element 1008. Gradients can also be established passively with the base element in a static or ambient mode or condition.

The cover or membrane 1010 modulates fluid pressure or flow by its physical properties of rigidity and flexibility, which can resist movement associated with a pressure gradient across the two sides of the cover or membrane 1010 and, conversely, the ability to collapse or change shape as a result of this gradient. Changing fluid pressure and volume modulates osmotic, capillary and atmosphere pressures, thereby changing the shape of the cover 1010. For example, changing the size and/or shape of the cover 1010 can produce fluid gradients by changing solvent volume for osmotic pressure, tube radius for capillary pressure and fluid volume/container volume for atmospheric pressure.

The porosity of the cover 1010 to fluids and solutes is another physical property, which affects fluid pressure and/or flow modulation by the cover 1010. For example, cover 1010 porosity can range from porous to semi-permeable to impervious. Semi-permeable covers 1010 are generally selectively capable of passing certain gaseous (vapor) phase elements and are impervious to certain liquid phase substances. Such selective permeability for various sizes of solutes, which can be a function of pore size, can be used for selectively creating fluid flow conduits for certain substances with the cover 1010.

The transducer component 1006 is located in a central or contained space 1012 generally defined by the cover 1010 and the tissue layer 1005, and can also be designed to manipulate fluid pressure and flow. Selective permeability for various sizes of solutes, which can be a function of pore size, can be used for selectively creating fluid flow conduits for certain substances with the transducer component 1006. The space 1012 can contain fluid alone, with or without solutes, or fluid and an engineered solid (e.g. bioengineered cells, beads, etc.). Fluid gradients for directing flow can be created, controlled and manipulated as a function of osmotic, capillary and atmospheric pressures.

Osmotic pressure control can be utilized with gas, liquid (with or without solutes) or both. By adjusting the concentrations of dissolved elements, a gradient can be established across the cover 1010 between the transducer component 1006 and the external environment. Capillary pressure control can involve transducer component 1006 configurations such as screens and three-dimensional meshwork providing channels and passages with predetermined sizes. A gradient can thereby be produced across the cover 1010, and can be engineered to modulate in response to the amount of fluid that is flowing. The transducer component 1006 can comprise, for example, an absorbable meshwork, which swells with liquid absorption whereby the spaces and passages change with exposure to liquid and cause corresponding changes in the capillary pressure gradients. The transducer component 1006 meshwork can be configured to hold more fluid at increased pressures (e.g., changing volume under osmotic pressure), thereby stretching the cover 1010, physically changing the conduit and passage sizes and modulating the pressure gradients and corresponding fluid flow.

Atmospheric pressure can remain constant through volume changes if the cover 1010 is sufficiently flexible to accommodate such changes. Differential fluid pressures and other gradients can be created and manipulated by selective permeability and rigidity of the cover membrane 1010. Strong osmotic/oncotic pressures can be established across the cover 1010 in order to cause liquid to selectively cross into the transducer 1012. On the other hand, if the cover 1010 is less flexible or stretchable, pressures tend to change within the central space 1012. For example, dissolved oxygen may be present in the central space 1012 and may be forced out through the cover 1010 by an increase in pressure. A water removal/oxygen delivery system is thus created. Alternatively, a specific connector conduit portion can be established in the cover 1010 for allowing active (mechanical or otherwise) modulation of atmospheric pressure (both positive and negative) inside the transducer component 1006, with the resultant gradient and fluid flow changes that will result to the other phases and elements in the central space 1012.

The effects of the aforementioned pressures on the gradients and functions of the transducer system 1002 are interrelated, whereby changing one or more design variables can affect others and thereby provide a relatively high level of control.

The ambient atmosphere and environment external to the transducer system 1002 can also be part of the system and controlled in order to achieve various desired performance objectives. The external environment can be ambient, or it may be contained within a larger, secondary enclosure. Connectors or patches, such as the cover connector 1014, can be utilized for fluid and pressure communication to the system 1002 from external sources, e.g. through tubing 1016.

For example, it may be desirable to control and manipulate certain atmospheric characteristics, such as oxygen content, humidity, etc. Such characteristics could remain relatively constant as elements are exchanged with the environment. Ambient liquids of various constitutions, concentrations and pressures can also comprise the ambient environment, and can be manipulated in order to achieve desired performance. Liquid volumes and concentrations can be sufficiently large for pressures and other characteristics to remain relatively constant contemporaneously with pressure gradient control and manipulation.

The tissue layer 1005 also has an interface relationship with the base element 1008. The system 1002 is medically useful in part because of its ability to control fluid flows involving solutes that are medicinal, nutritional and metabolically active. Biological tissue inherently functions as a cover membrane. Therefore, sealing the edges of the cover 1010 to healthy skin around the wound 1004 configures the system with the tissue layer 1005 comprising the lower enclosure, which cooperates with the cover 1010 to enclose the transducer component 1006. By way of example, steep gradients and rapid fluid flows can be achieved by constructing the layers of the system 1002 in such a way as to move accumulated concentrations of elements away from the base layer interface between the tissue 1005 and the transducer component 1006. Conversely, relatively high concentrations or pressures of desired elements can be achieved in a delivery mode of operation in order to affect high delivery rates to the tissue 1005. Tissue interaction can take the form of fluid absorption, exudation/transudation, exchange (solute/solvent), cellular response, and other physiological interactions.

Interconnecting base elements 1008 together inside of an interconnected second space environment attached to tissue can provide a device capable of expansion or contraction to fit multiple fluid flow needs for removal and delivery requirements for medical treatment of tissue of all sizes. The base element 1008 can range in size from gross macroscopic to molecular and nanometer, and tubule passage sizes can correspondingly cover a wide range for achieving desired fluid, pressure, gradient, biologic and other effects. Without limitation on the generality of useful applications of the present invention, it is anticipated that most of the desired fluid effects will occur utilizing passages and matrices in the micron to millimeter range.

Gradients can be formed with various forces and interactions at different locations within the system 1002. For example, within the connector and tubing 1014, 1016 positive and negative pressures associated with external fluid and pressure sources can be formed. The outer surface of the cover 1010 forms an interface with the atmosphere or other environment external to the base element 1008. The inner surface of the cover 1010 forms an interface between the cover and the transducer component 1006. Within the transducer component 1006 pressure, osmotic, oncotic, chemical, biological, thermal and other gradients are formed. A transducer/tissue interface is formed between the transducer component 1006 and the tissue layer 1005. Finally, gradients are formed within the tissue layer 1005.

Figure 23:
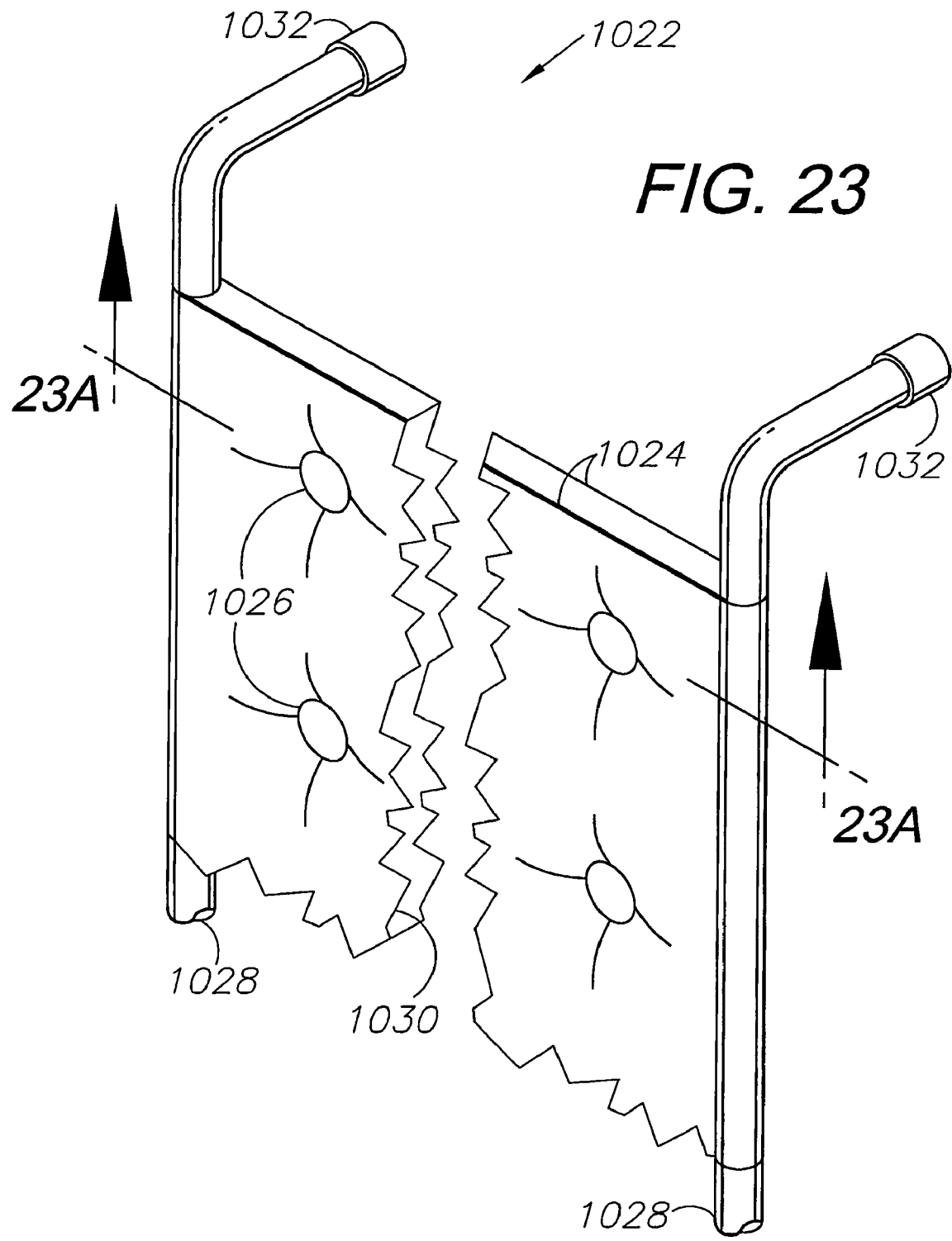
FIG. 23 is a perspective view of an alternative embodiment composite sheet panel system.

Another modified embodiment composite sheet panel system 1022 is shown in FIGS. 23 and 23A and generally comprises a pair of perforated or semi-permeable sheets 1024 positioned in generally parallel, overlying relation with spot interconnections (e.g., spot welds) 1026, which can be suitably spaced for optimal performance. A pair of manifolds 1028 is provided along edges of the sheets 1024 for fluid introduction into or extraction out of an interstitial space 1030 comprising multiple, interconnected fluid passage pockets. Port assemblies 1032 for inflow and outflow are connected to the manifolds 1028 and can comprise Luer lock connectors, drain cocks, vents, sealing plugs, etc. for connection to the atmosphere or suitable sources of pressure and/or fluids, which can be chosen for particular patient indications. As shown in FIG. 23A, the central space 1030 can expand under positive pressure whereby multiple chambers and passages are formed between the sheets 1024 and the spot interconnections 1026. For example, fluid content to one of the ports 1032 can be dissipated throughout the wound, and fluid drainage can be accomplished through the other port 1032.

The spot interconnections 1026 can restrain separation of the sheets 1024, which may be desirable when the central space 1030 is filled with larger volumes of pressurized fluid. The panel system 1022 can comprise various thin, flexible and durable materials, including polyurethane, cellulose, cellophane or rayon. Such materials are preferably chosen for their properties of permeability, i.e. membrane-like behavior for separating types of fluid on each side, and liquid adhesion involving their abilities to adhere to various liquids presented to the sheet 1024 surfaces and surface tension properties. The surfaces can optionally be coated with proteins and other materials affecting liquid adhesion. Hydrophobic and hydrophilic properties are also applicable to membrane-like performance. Additional performance-affecting construction material variables include the thickness and permeability of the sheets 1024. Still further, the size and spacing of the spot interconnections 1026 can vary considerably among systems embodying the present invention. For example, micro-systems with sub-centimeter spacing may be indicated for certain closure procedures, whereas macro systems with interconnections spaced several centimeters apart may be indicated for others.

The manifolds 1028 and the ports 1032 can likewise have various sizes, configurations and locations. For example, the manifolds 1028 can be located on opposite edges, over-and-under along the same edge or along adjacent edges. The panel system 1022 can be provided as an elongated strip, which can be cut-to-length transversely for custom-fit installations. The cut edges can be taped over or otherwise suitably closed. The ports 1032 can be fabricated with flexible tubing or other suitable materials, and can be fitted with various suitable connectors and terminations, including selectively closable sealing plugs at 1032.

Another modified embodiment composite sheet panel system 1042 is shown in FIGS. 24 and 24A and includes a spacer matrix 1044 comprising multiple, individual spacers 1046 with generally flat, rectangular configurations extending between and providing a predetermined spacing between sheets 1048, thus defining a central space 1050. The spacers 1046 can be arranged to direct, restrict and otherwise control fluid flow under various conditions of pressure and flow rate. For example, by providing a sufficient number of spacers 1046 with sufficient rigidity, the sheets 1048 can be separated under negative pressure, thereby avoiding a flap-valve closure effect resulting from the application of negative pressure.

Figure 25:
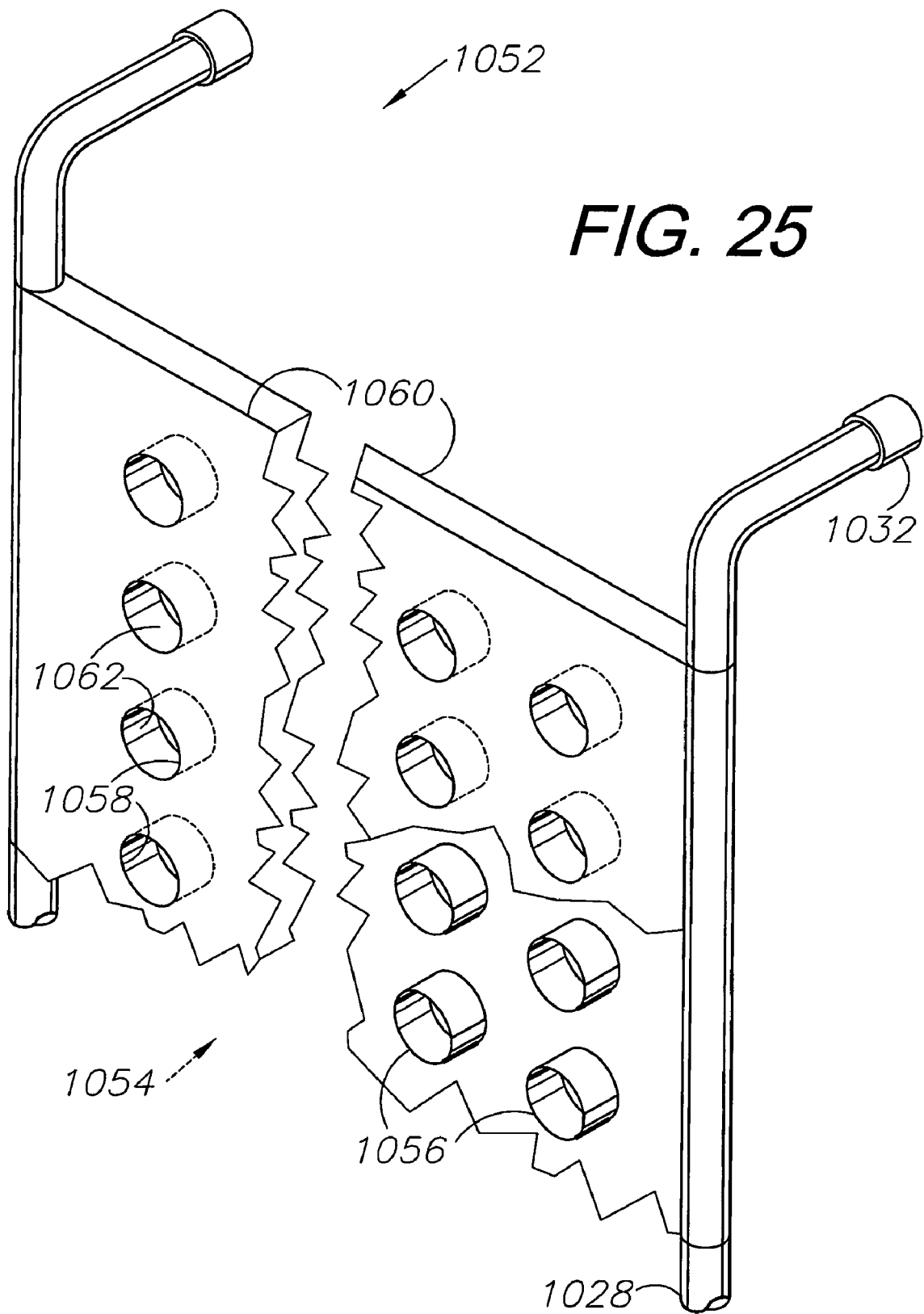
FIG. 25 is a perspective view of another alternative embodiment composite sheet panel system.
Figure 26:
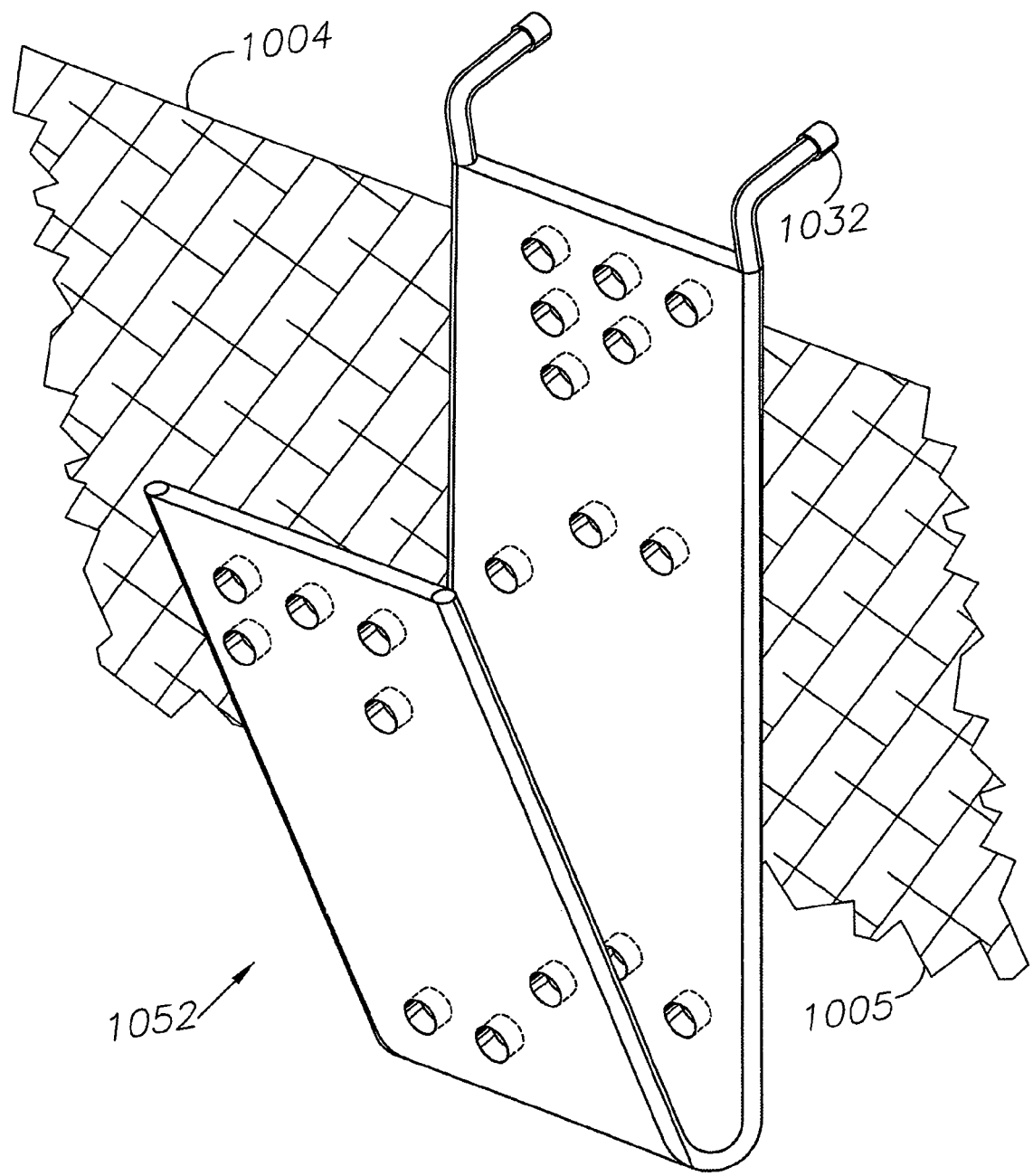
FIG. 26 is a perspective view thereof, shown installed in a wound for closing same.

Another modified embodiment composite sheet panel system 1052 is shown in FIGS. 25 and 26 and includes a spacer matrix 1054 generally comprising multiple cylindrical spacers or tubules 1056 with opposite ends 1058 open at respective sheets 1060 whereby tubule passages 1062 provide additional surface area, which is exposed to fluid from both sides of the panel system 1052. This embodiment provides a relatively large exposed surface area, which facilitates pressure and fluid exchange between the system 1052 and the patient. The tubules 1056 can comprise similar materials to the sheets 1060, e.g. perforated or semi-permeable, or they can comprise different materials chosen for appropriate permeability and other characteristics. FIG. 26 shows the sheet panel system 1052 folded double and inserted into a wound for drawing the separated tissue portions together and for controlling fluid flow and pressure application in order to facilitate wound closure. The ports 1032 can apply positive or negative pressure and can inject or extract fluid. The operation of the closure system 1052 can be sequenced as appropriate, with predetermined durations for different phases of the wound treatment procedure. For example, positive and negative pressures can be alternately applied. Fluids, such as antibiotics, analgesics, anesthetics and growth factors can be applied in predetermined dosage levels for predetermined durations.

If the system is provided with a manifold, the added fluids or concentrations can be sequentially changed and varied as the changing environment of healing requires without changing the device or dressing. Oxygen can be applied intermittently for maximizing the benefits of topical hyperbaric therapy. Negative pressure can be utilized for extracting wound exudate and closing the wound edges.

Figure 27:
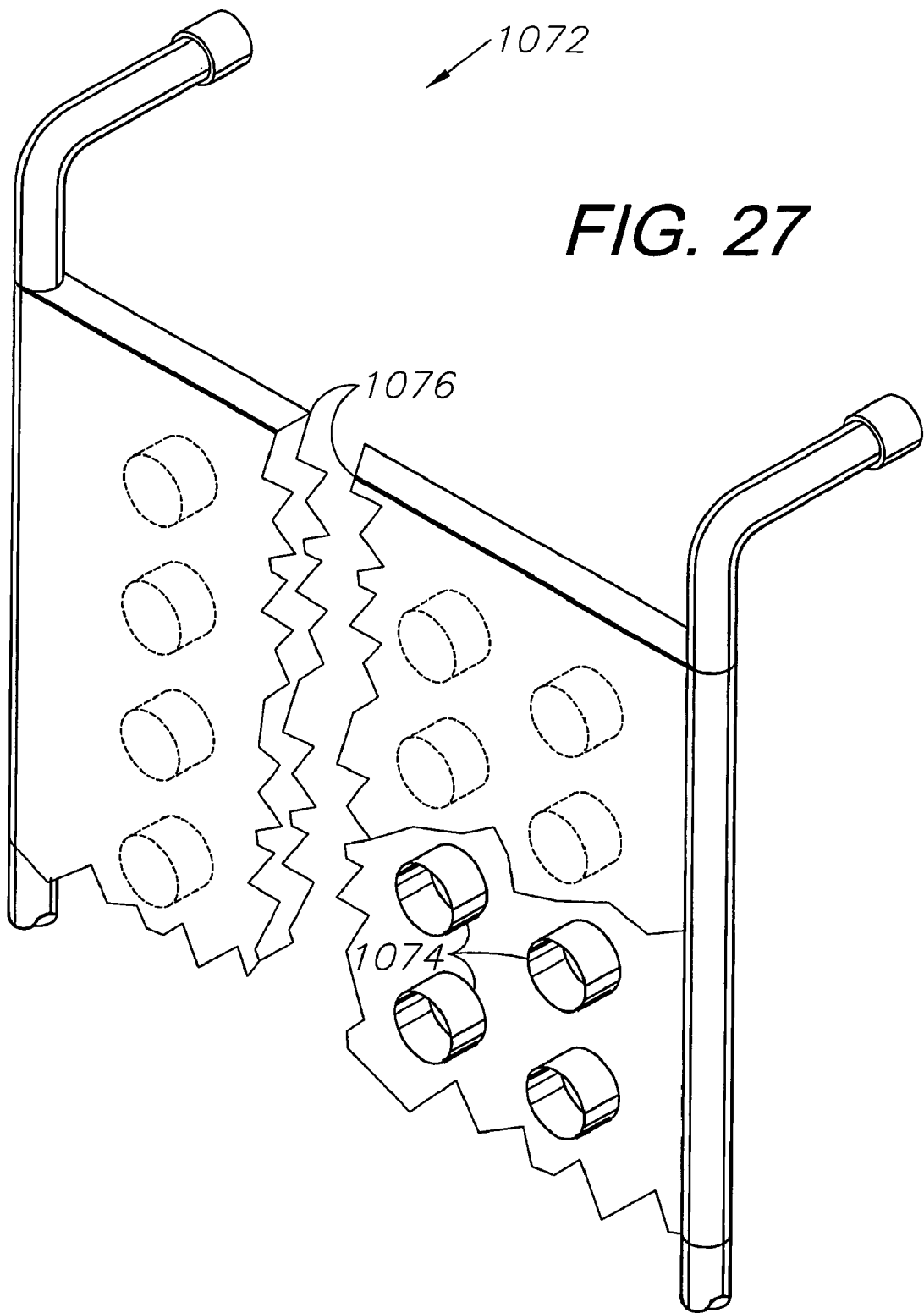
FIG. 27 is a perspective view of another alternative embodiment composite sheet panel system.
Figure 28:
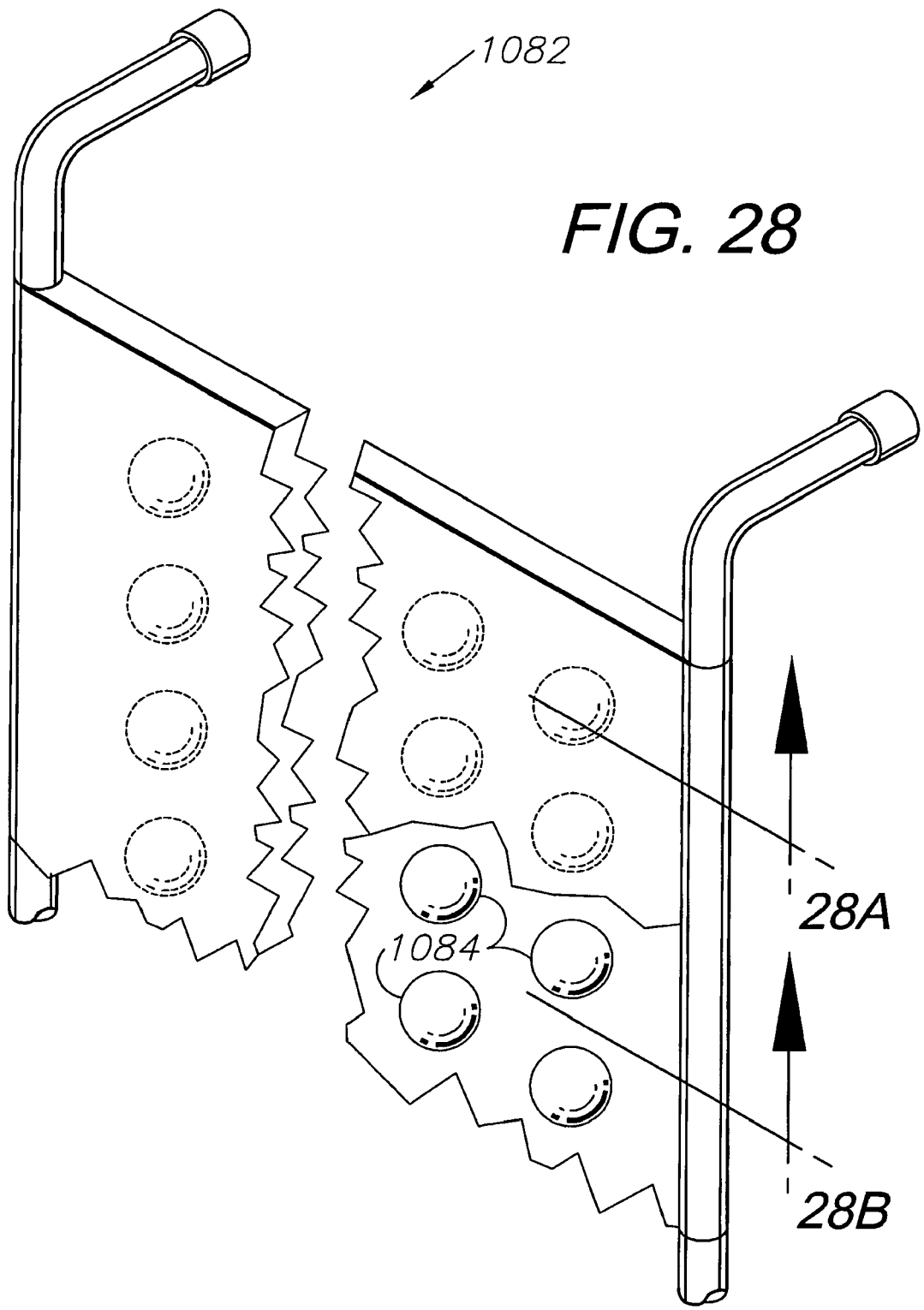
FIG. 28 is a perspective view of another alternative embodiment composite sheet panel system.

Another modified embodiment composite sheet panel system 1072 is shown in FIG. 27 and is similar to the panel system 1052, except that cylindrical spacers or tubules 1074 thereof are closed at their respective ends by sheets 1076. FIGS. 28, 28A and 28B show yet another modified embodiment composite sheet panel system 1082, which is similar to the system 1072 except that the cylindrical spacers 1074 are replaced with spheres 1084. The panel systems 1002, 1022, 1042, 1052, 1072 and 1082 are flexible and scalable and therefore can be formed in various configurations with different sizes and shapes. They can be premanufactured or trimmed-to-fit, as needed.

Figure 32:
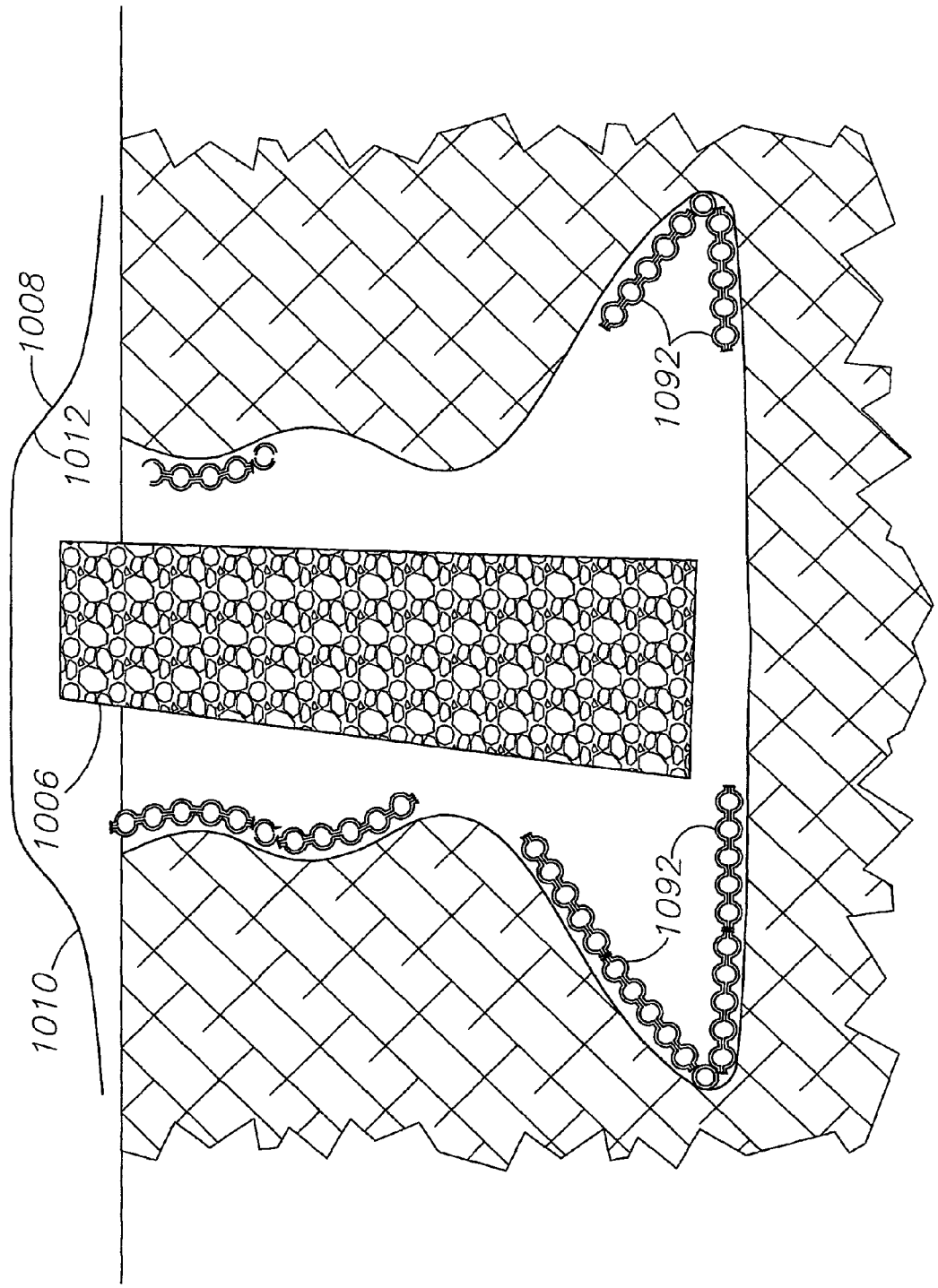
FIG. 32 is another cross-sectional view thereof, shown in another wound for closing same

FIGS. 29 and 29A show another alternative embodiment construction of a composite sheet panel system 1092 with a pair of sheets 1094, each of which includes multiple hemispherical protrusions 1096, which are aligned with the sheets 1094 placed together to form multiple pockets 1097, which can be accessed by suitable manifolds and ports. As shown in FIG. 29A, the protrusions can be perforated with passages 1098 for communicating fluid with the pockets 1097. FIG. 30 shows another alternative embodiment composite sheet panel system 1102 with a sheet 1104, which can be similar to the sheets 1094, covered by a membrane 1106. FIG. 31 shows the composite sheet panel system 1092 in a wound with a transducer component 1006 placed in communication with the composite sheet panel system 1092 and located adjacent the skin surface. A membrane cover 1010 is placed over the transducer component 1006 and can be attached to a pressure source via a connector 1014 as described above. Another application of the composite sheet panel system 1092 is shown in FIG. 32 and includes a transducer component 1006 placed in the wound and partially surrounded by the composite sheet panel system 1092, with a cover 1010 placed thereover.

Figure 34:
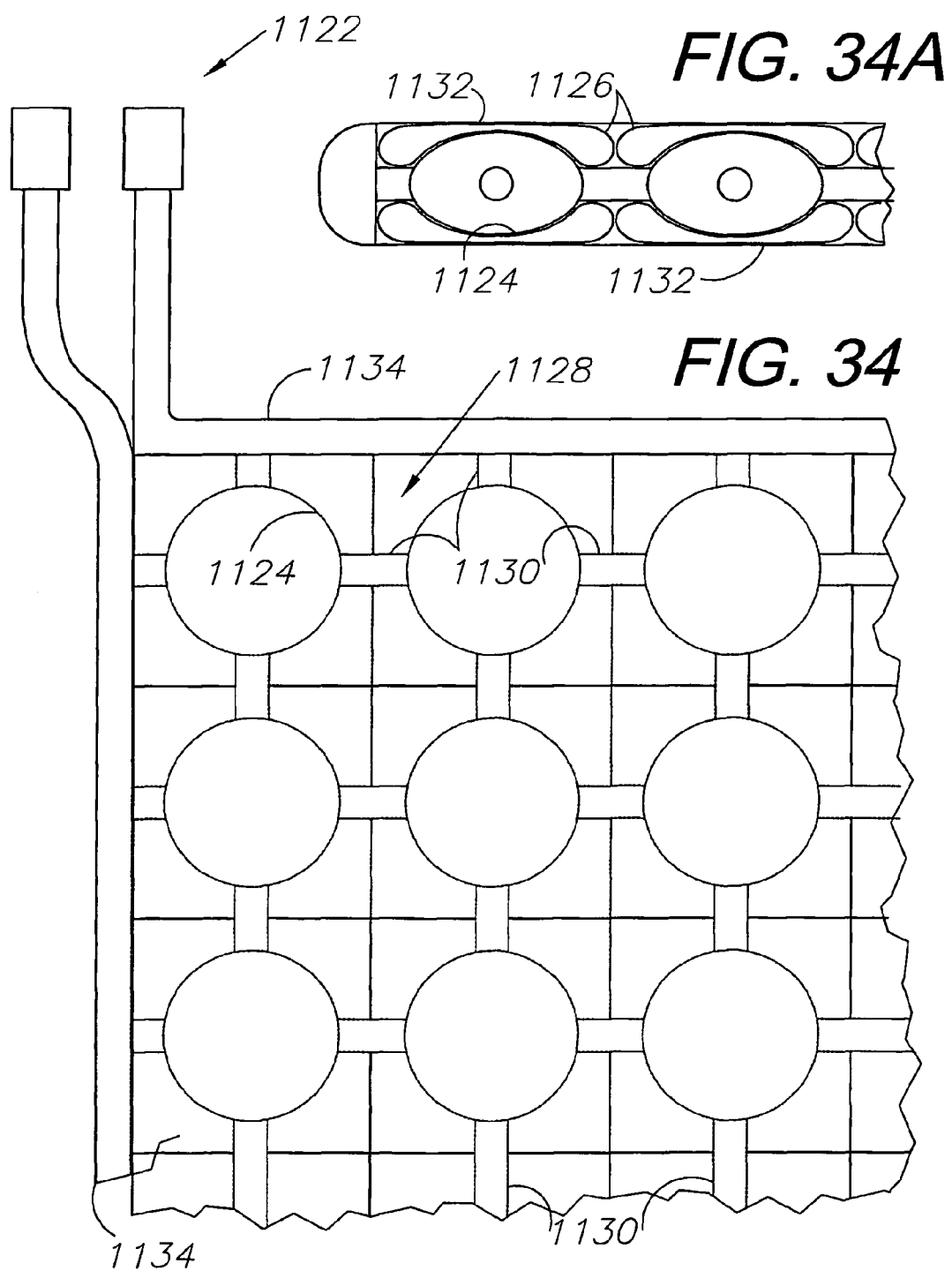
FIG. 34 is a plan view of another alternative embodiment composite sheet panel system.

FIGS. 33 and 33A show a composite sheet panel system 1112 comprising another alternative embodiment of the invention with multiple, spherical pockets 1114 interconnected by a matrix of tubes 1116 for fluidic communication with external sources. FIGS. 34 and 34A show another modified embodiment composite sheet panel system 1122 with disk-shaped pockets 1124 and passages 1126 positioned on both sides of a pocket matrix 1128 including interconnecting tubes 1130. Sheets 1132 are placed on both sides of the system 1122 and manifolds 1134 are located along respective edges in communication with the tubes 1130.

Figure 35:
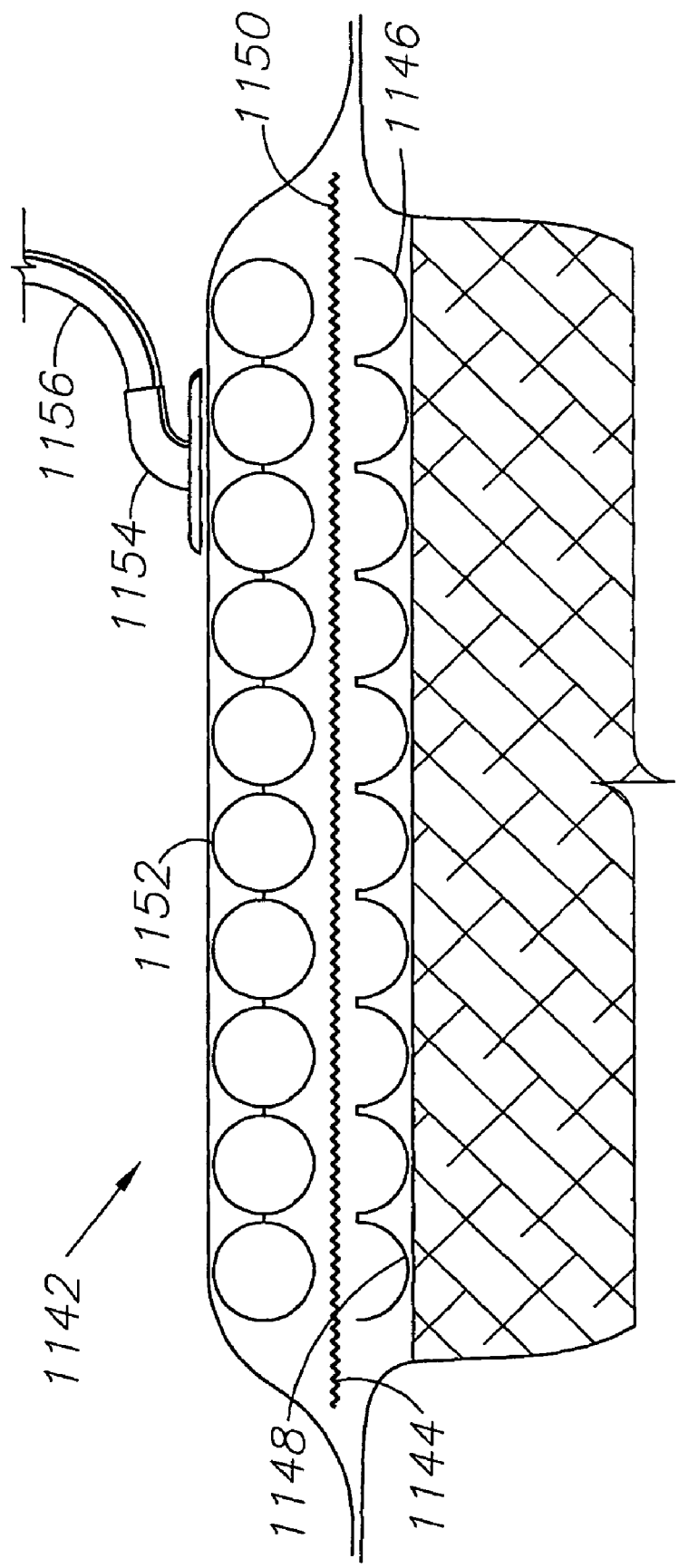
FIG. 35 is a cross-sectional view of another alternative embodiment composite sheet panel system.
Figure 36:
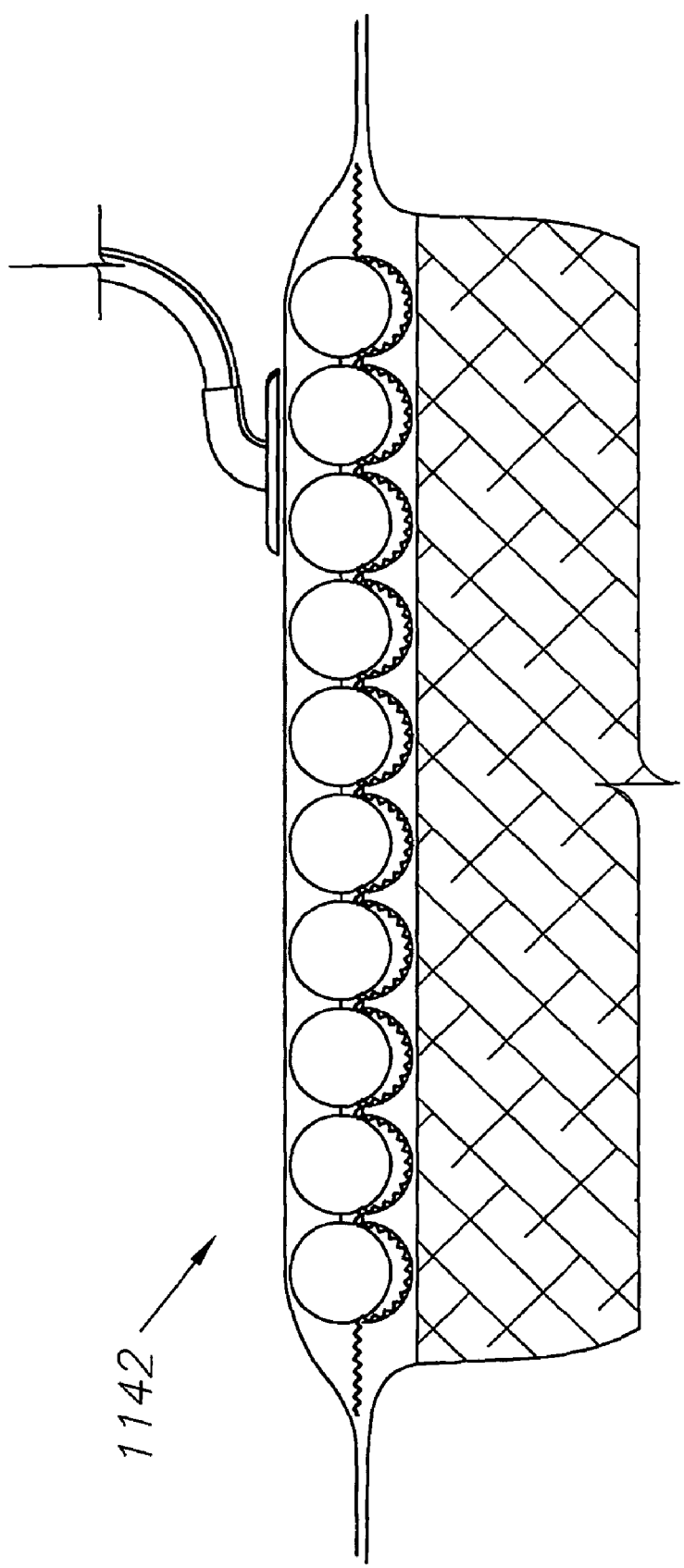
FIG. 36 is another cross-sectional view thereof, shown in a compressed, compacted configuration.
Figure 37:
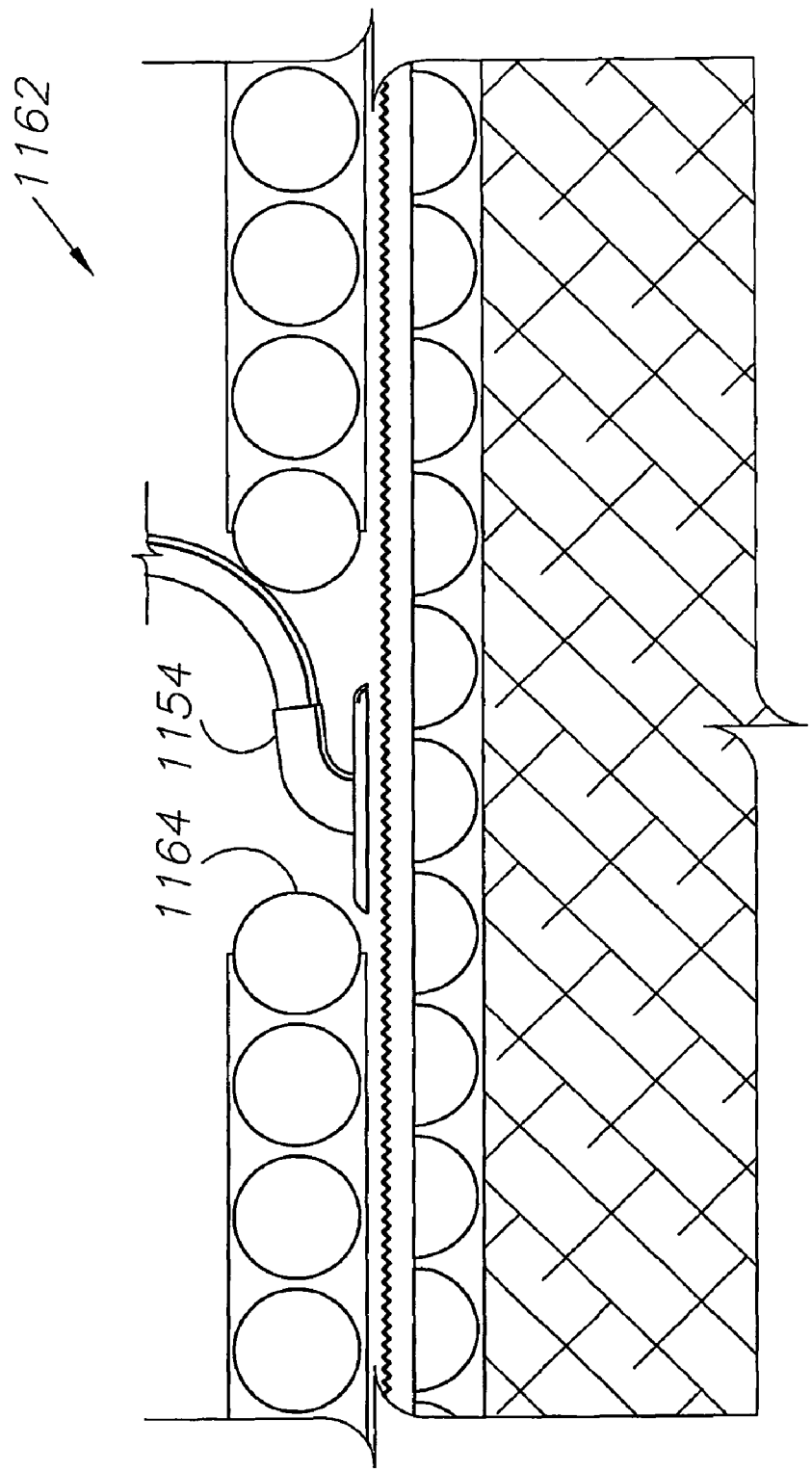
FIG. 37 is a cross-sectional view of another alternative embodiment composite sheet panel system.

FIGS. 35-36 show another alternative embodiment composite sheet panel system 1142 with an inner transducer component comprising a sheet 1144 with spherical protrusions 1146 defining outwardly-open pockets 1148. An intermediate transducer component 1150 is placed over the first transducer component 1144 and an outer transducer component 1152 with spherical elements 1153 is placed over the intermediate transducer component 1150. A cover 1110 is placed over the transducer components 1144, 1150, 1152 and can be connected to an external pressure source by a connector 1154 via tubing 1156. As shown in FIG. 36, the application of negative pressure tends to push the spherical elements 1153 of the outer transducer component 1152 into the pockets 1148 with the lateral transfer sheets 1150 therebetween whereby the fluids are dispersed through capillary and surface tension action. FIG. 37 shows a composite sheet panel system 1162 comprising a modified embodiment of the system 1142 with an opening 1164 formed in the outer transducer component 1152 for receiving a connector 1114 in contact with the lateral transfer sheet intermediate transducer component 1150. Juxtaposition of these shapes creates a controlled capillary space, which allows faster, more distal movement of fluid.

Figure 38:
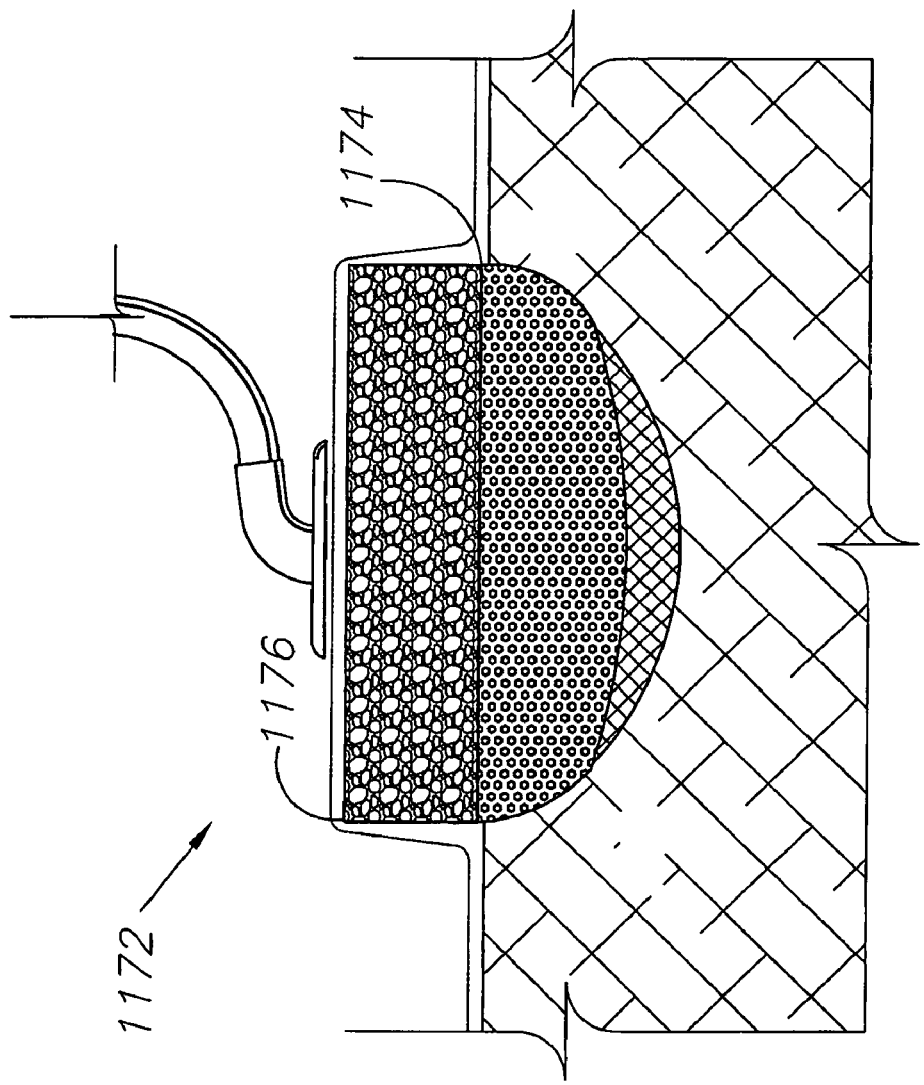
FIG. 38 is a cross-sectional view of another alternative embodiment gradient wound treatment system.

FIG. 38 shows another alternative embodiment wound treatment system 1172 with an inner transducer component comprising a layer of beads 1174 located generally under an outer transducer component 1176. The beads 1174 can comprise living cells, various pharmacological agents or a matrix for facilitating fluid and pressure transfer.

Figure 39:
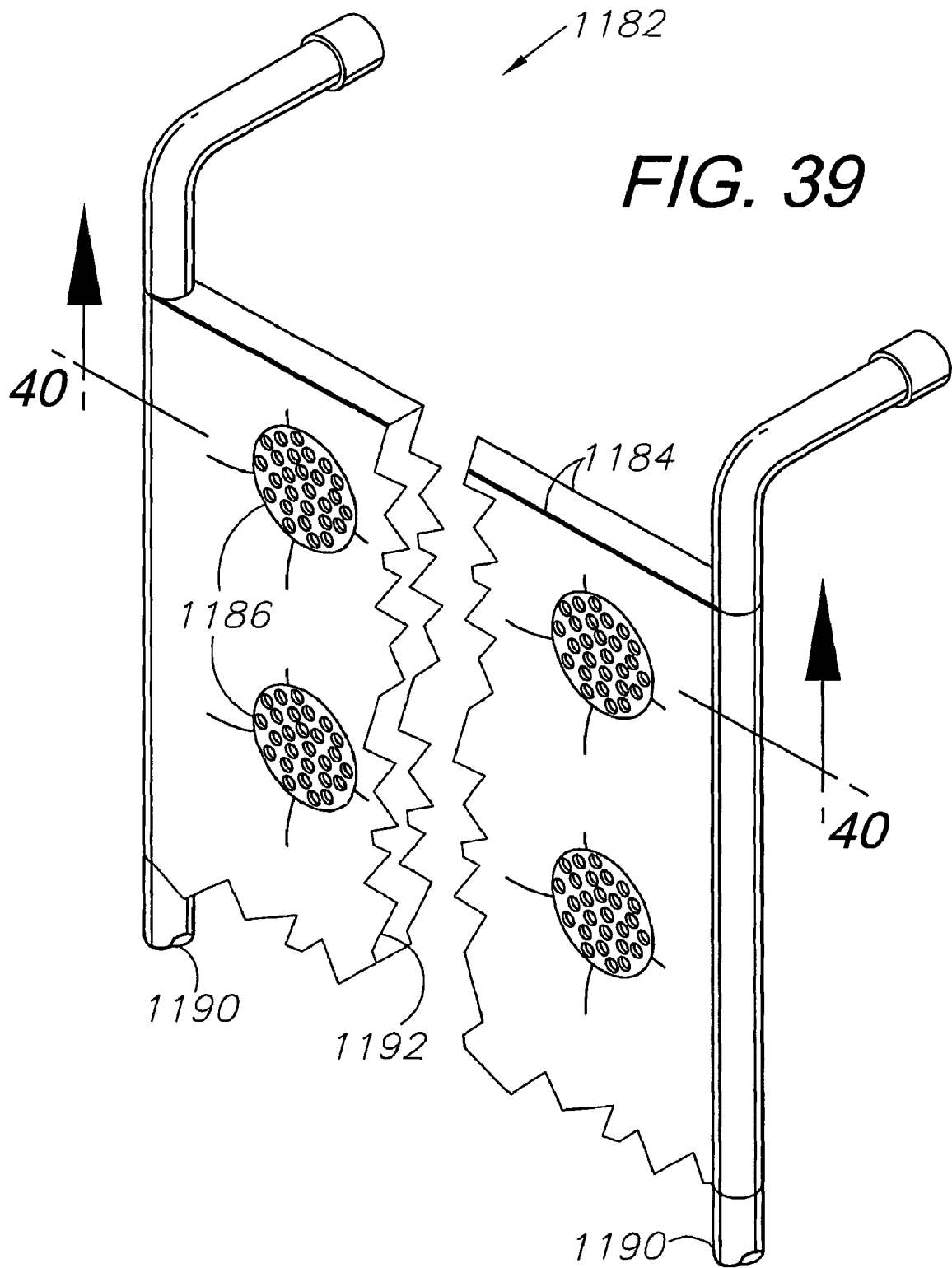
FIG. 39 is a perspective view of another alternative embodiment composite sheet panel system.
Figure 40:
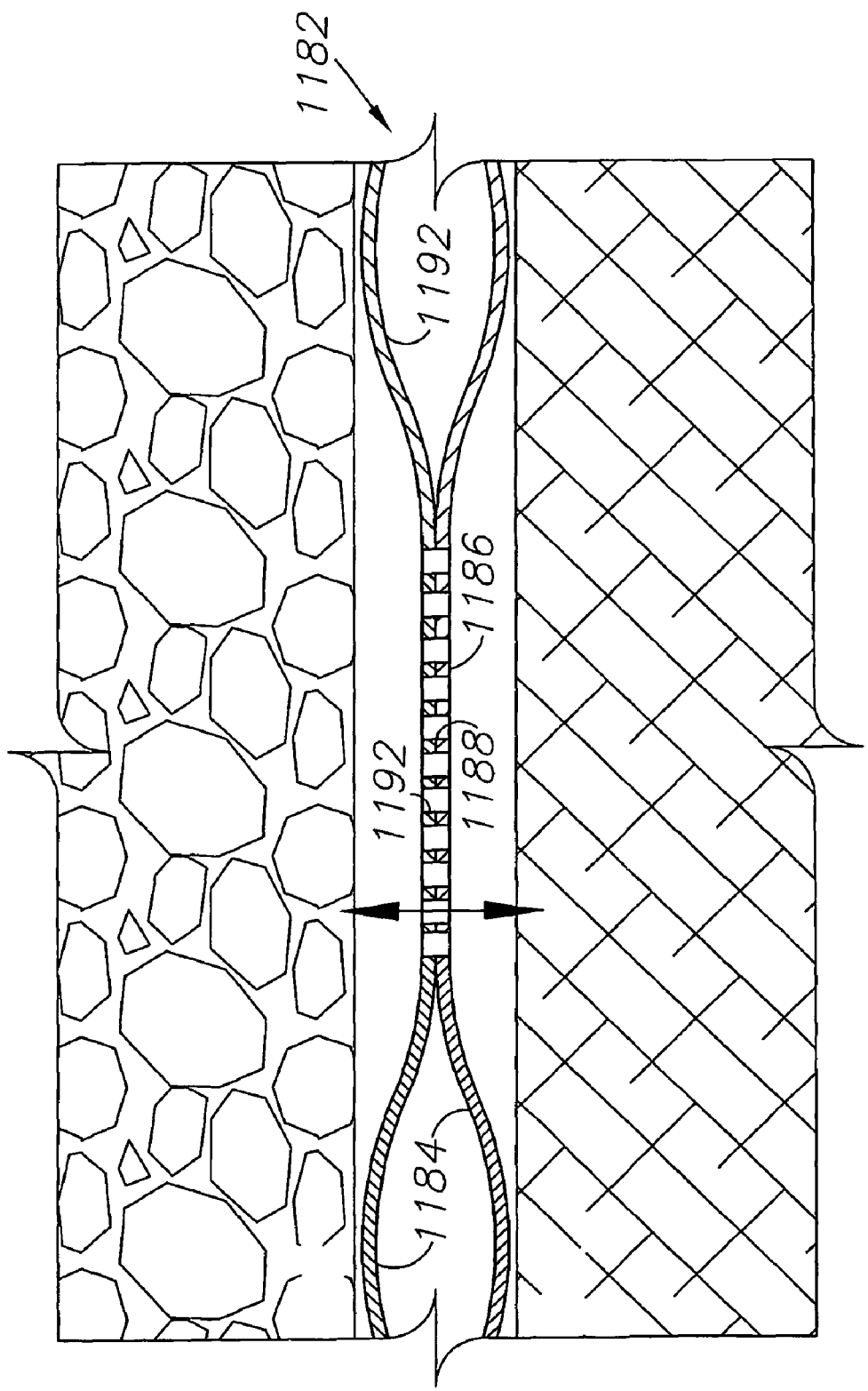
FIG. 40 is a cross-sectional view thereof, taken generally along line 40-40 in FIG. 39.

FIGS. 39 and 40 show another alternative embodiment wound treatment system 1182 with first and second sheets 1184 attached at disk-shaped connections 1186, which are similar to the spot welds 1026 described above, except with perforations 1188. In lieu of the multiple perforations 1188 shown, various sizes of single openings could be provided or the disk-shaped connections 1186 could be porous material. Manifolds 1190 can be placed along the longitudinal and/or transverse edges of the sheets 1184 and connected to an external fluid and pressure sources as described above. The system 1182 can be placed between a transducer component 1006 and tissue 1005 whereby fluidic communication can occur through the perforations 1188. The sheets form pockets interconnected to form a fluid passage interstitial space 1192, which can be maintained with positive pressure, for example, to provide a smooth, uniform surface for clinical applications such as reepithelialization.

XVI. Conclusion

It is to be understood that while certain forms of the present invention have been illustrated and described herein, it is not to be limited to the specific forms or arrangement of parts described and shown.

Furthermore, it should be appreciated that continuations, divisionals, and continuations-in-part applications depending from this specification may be pending at the time this patent issues, the claims of which may encompass embodiments and applications that are broader than the claims appended herein. Accordingly, embodiments or elements disclosed in the specification but not literally claimed in the appended claims, if any, should not be presumed to be dedicated to the public.

The invention claimed is:

1. An osmotic transducer system, which includes:
   a base element including a transducer component adapted for fluidic communication with a wound and a semi-permeable cover adapted for placement over the transducer component;
   a central space formed by the cover and patient tissue structure, said transducer component being located in said central space;
   an osmotic gradient formed with said base element and adapted for manipulating fluid elements whereby a pressure gradient is formed to produce useful fluid flow; and
   said gradient being formed by the manipulation of osmotic, capillary, atmospheric and gas partial pressures with externally-applied fluid pressure comprising either vacuum (negative) pressure or applied (positive) pressure.

2. The system according to claim 1 wherein said cover has a configuration chosen from among the group comprising: impervious, semi-permeable and permeable.

3. The system according to claim 1, which includes:
   a vacuum source connected to said base element and forming a pressure gradient in said transducer component.

4. A gradient system for treating a wound, which system includes:
   an inner pressure transducer including first and second flexible sheets positioned in generally overlying relation and forming longitudinal and transverse inner pressure transducer edges;
   multiple spot connections fixedly interconnecting said first and second sheets and each including multiple perforations extending through said first and second sheets;
   said sheets forming multiple, interconnected pockets therebetween whereat said sheets are adapted for separation under positive fluid pressure and said pockets define a fluid passage interstitial space between said sheets;
   first and second manifolds attached to said first and second sheets along respective inner pressure transducer edges, said manifolds fluidically communicating with said pockets along respective said inner pressure transducer edges and each including an inlet/outlet port;
   an outer pressure transducer comprising a porous foam material forming capillary, osmotic and atmospheric pressure gradients;
   said outer pressure transducer being located over said inner pressure transducer in fluidic communication therewith;
   a flexible cover placed over said outer pressure transducer and including a perimeter adapted for a adhesively securing to a patient around said wound;
   said inner and outer pressure transducers and said cover forming a base element with a central space generally enclosed by said cover and patient tissue;
   said manifolds extending through said central space and terminating externally of said cover; and
   an external pressure source connected to said manifolds and adapted for providing positive and negative pressure to said base element through said manifolds.

5. A wound treatment and closure method, which comprises the steps of:
   providing a base element with a transducer component and a semi-permeable cover;
   placing said transducer component in communication with tissue in said wound;
   placing said cover over said transducer component in contact with skin surface around said wound;
   establishing a gradient with respect to said wound, said transducer component and said cover;
   directing fluid flow to or from said tissue by controlling pressures associated with said gradient;
   establishing osmotic, capillary, atmospheric and gas partial gradients with respect to said wound said transducer component and said cover; and
   externally applying fluid pressure comprising either vacuum (negative) pressure or applied (positive) pressure from an external fluid pressure source.

6. The method according to claim 5, which includes the additional steps of:
   providing said pressure transducer with a manifold; and
   connecting said manifold to said external fluid pressure source.

7. The method according to claim 5, which includes the additional steps of:
   providing a second cover; and
   placing said second cover in overlying relation over said first cover.

8. An osmotic transducer system, which includes:
   a base element including a transducer component adapted for fluidic communication with a wound and a cover adapted for placement over the transducer component;
   a central space formed by the cover and patient tissue structure, said transducer component being located in said central space;
   an osmotic gradient formed with said base element and adapted for manipulating fluid elements whereby a pressure gradient is formed to produce useful fluid flow;
   said gradient being formed by the manipulation of osmotic, capillary, atmospheric and gas partial pressures;
   a pair of sheets positioned in generally parallel relation and including multiple spot connections whereat said sheets are fixedly attached to each other, said spot connections having configurations chosen from among the group comprising: impervious; semi-permeable; porous; and perforated;
   multiple, interconnected pockets formed between said sheets;
   said pockets forming a fluid passage interstitial space between said sheets; and
   a manifold connected to said sheets in communication with said interstitial space and an external pressure source.

9. The system according to claim 8, which includes:
   said connections being chosen from among the group comprising: sheet-to-sheet spot connections; spacers; tubules open at said sheet surfaces; tubules closed at said sheet surfaces; and spheres.

10. The system according to claim 8, which includes:
said connections comprising multiple spheres connected to said sheets; and
a matrix of tubes fluidically connecting said spheres and said manifold.

11. The system according to claim 8, which includes:
a plurality of hollow disks;
a matrix of tubes interconnecting said disks and said manifold; and
a plurality of conduits placed over said disks and communicating with said manifold.

12. An osmotic transducer system, which includes:
a base element including a transducer component adapted for fluidic communication with a wound and a cover adapted for placement over the transducer component;
a central space formed by the cover and patient tissue structure, said transducer component being located in said central space;
an osmotic gradient formed with said base element and adapted for manipulating fluid elements whereby a pressure gradient is formed to produce useful fluid flow;
said gradient being formed by the manipulation of osmotic, capillary, atmospheric and gas partial pressures; and
said transducer component comprising: a first transducer component including multiple, hemispherical protrusions forming outwardly-open pockets; an intermediate porous material layer placed over said first transducer component; and a second transducer component comprising a plurality of spherical elements interconnected to form a sheet.

13. The system according to claim 12, which includes:
at least one of said hemispherical protrusions and said spherical elements being perforated.

14. The system according to claim 13, which includes:
an opening formed in said second transducer component; and
an external connector attached to said intermediate layer within said opening and adapted for connection to an external pressure source.

15. An osmotic transducer system, which includes:
a base element including a transducer component adapted for fluidic communication with a wound and a cover adapted for placement over the transducer component;
a central space formed by the cover and patient tissue structure, said transducer component being located in said central space;
an osmotic gradient formed with said base element and adapted for manipulating fluid elements whereby a pressure gradient is formed to produce useful fluid flow;
said gradient being formed by the manipulation of osmotic, capillary, atmospheric and gas partial pressures; and
said transducer component comprising: an inner transducer component including multiple, discrete beads chosen from among the group comprising pharmacologicals, growth factors, living cells and inert materials; and an outer pressure transducer comprising a foam material with hydrophobic or hydrophilic properties.

16. A wound treatment and closure method, which comprises the steps of:
providing a base element with a transducer component and a cover;
placing said transducer component in communication with tissue in said wound;
placing said cover over said transducer component in contact with skin surface around said wound;
establishing a gradient with respect to said wound, said transducer component and said cover;
directing fluid flow to or from said tissue by controlling pressures associated with said gradient;
externally applying fluid pressure comprising either vacuum (negative) pressure or applied (positive) pressure from an external fluid pressure source;
providing said pressure transducer with a manifold;
connecting said manifold to said external fluid pressure source;
forming said pressure transducer with first and second sheets;
connecting said sheets in overlying relation at multiple spot connections; and
forming multiple pockets between said sheets and interconnecting said pockets to form a fluid passage interstitial space between said sheets.

17. The method according to claim 16, which includes the additional step of:
forming said spot connections with configurations chosen from the group comprising: sheet-to-sheet spot connections; spacers; tubules open at said sheet surfaces; tubules closed at said sheet surfaces; and spheres.

18. The method according to claim 16, which includes the additional step of:
fixedly attaching said sheets to each other at said spot connections;
forming said spot connections with configurations chosen from among the group comprising: impervious; semi-permeable; porous; and perforated.

19. The method according to claim 18, which includes the additional steps of:
providing first and second manifolds;
connecting said manifolds to said sheets in communication with said interstitial space;
providing an external pressure source; and
providing negative (vacuum) and positive (applied) pressures to said interstitial space from said external pressure source.

20. A wound treatment and closure method, which comprises the steps of:
providing a base element with a transducer component and a cover;
placing said transducer component in communication with tissue in said wound;
placing said cover over said transducer component in contact with skin surface around said wound;
establishing a gradient with respect to said wound, said transducer component and said cover;
directing fluid flow to or from said tissue by controlling pressures associated with said gradient;
forming said pressure transducer with a hydrophilic or hydrophobic foam material;
forming a first pressure transducer component with said foam material;
providing a second pressure transducer component including multiple, discrete beads chosen from among the group comprising pharmacologicals, growth factors, living cells and inert materials; and
forming a pressure gradient between said first and second pressure transducers.

* * * * *

UNITED STATES PATENT AND TRADEMARK OFFICE
CERTIFICATE OF CORRECTION

PATENT NO. : 7,645,269 B2
APPLICATION NO. : 11/523672
DATED : January 12, 2010
INVENTOR(S) : David S. Zamierowski It is certified that error appears in the above-identified patent and that said Letters Patent is hereby corrected as shown below:

Column 19, line 66, strike out "and including a perimeter adapted for a adhesively" and insert instead --and including a perimeter adapted for adhesively--.

Signed and Sealed this

Fourteenth Day of December, 2010

David J. Kappos
*Director of the United States Patent and Trademark Office*